(12) United States Patent
Plettenburg et al.

(10) Patent No.: US 8,710,228 B2
(45) Date of Patent: Apr. 29, 2014

(54) CYCLOALKYLAMINE SUBSTITUTED ISOQUINOLINE DERIVATIVES

(75) Inventors: Oliver Plettenburg, Frankfurt am Main (DE); Armin Hofmeister, Frankfurt am Main (DE); Dieter Kadereit, Frankfurt am Main (DE); Stefan Peukert, Arlington, MA (US); Sven Ruf, Frankfurt am Main (DE); Matthias Löhn, Frankfurt am Main (DE); Peter Monecke, Frankfurt am Main (DE); Alexander Schiffer, Frankfurt am Main (DE); Aimo Kannt, Frankfurt am Main (DE); Markus Kohlmann, Frankfurt am Main (DE)

(73) Assignee: Sanofi, Paris (FR)

( * ) Notice: Subject to any disclaimer, the term of this patent is extended or adjusted under 35 U.S.C. 154(b) by 810 days.

(21) Appl. No.: 12/487,386

(22) Filed: Jun. 18, 2009

(65) Prior Publication Data

US 2010/0081671 A1 Apr. 1, 2010

Related U.S. Application Data

(63) Continuation of application No. PCT/EP2007/011167, filed on Dec. 19, 2007.

(30) Foreign Application Priority Data

Dec. 27, 2006 (EP) .................... 06026894

(51) Int. Cl.
*A61K 31/47* (2006.01)
*C07D 217/00* (2006.01)

(52) U.S. Cl.
USPC .......................... 546/139; 514/309

(58) Field of Classification Search
None
See application file for complete search history.

(56) References Cited

U.S. PATENT DOCUMENTS

| 5,480,883 | A | 1/1996 | Spada et al. |
| 6,903,107 | B1 | 6/2005 | Timmers et al. |
| 7,217,722 | B2 | 5/2007 | Takami et al. |
| 7,618,985 | B2 | 11/2009 | Ray et al. |
| 2003/0220368 | A1 | 11/2003 | Ozaki et al. |
| 2004/0138286 | A1 | 7/2004 | Imazaki et al. |
| 2006/0079556 | A1 | 4/2006 | Sher et al. |
| 2007/0060595 | A1 | 3/2007 | Yoshizawa et al. |
| 2008/0045566 | A1 | 2/2008 | Ray et al. |

FOREIGN PATENT DOCUMENTS

| EP | 1403255 | 3/2004 |
| EP | 1541559 | 6/2005 |
| EP | 1550660 | 7/2005 |
| FR | 2485537 | 6/1980 |
| JP | 10087629 | 4/1998 |
| WO | WO 92/02476 | 2/1992 |
| WO | 9706802 | 2/1997 |
| WO | 9723214 | 7/1997 |
| WO | WO 98/06433 | 2/1998 |
| WO | 9911642 | 3/1999 |
| WO | 0024718 | 5/2000 |
| WO | 0073299 | 12/2000 |
| WO | WO 01/39726 | 6/2001 |
| WO | 0153288 | 7/2001 |
| WO | 0156988 | 8/2001 |
| WO | 0164656 | 9/2001 |
| WO | WO 01/64238 | 9/2001 |
| WO | 0177101 | 10/2001 |
| WO | 0192227 | 12/2001 |
| WO | 0234712 | 5/2002 |
| WO | 02055496 | 7/2002 |
| WO | 02076457 | 10/2002 |
| WO | 02088101 | 11/2002 |
| WO | 03018556 | 3/2003 |
| WO | 03024450 | 3/2003 |
| WO | WO 03/053330 | 7/2003 |
| WO | 2004113297 | 12/2004 |
| WO | WO 2004/106325 | 12/2004 |
| WO | 2005035933 | 2/2005 |
| WO | 2005035516 | 4/2005 |
| WO | WO 2005/030791 | 4/2005 |
| WO | WO 2005/303130 | 4/2005 |
| WO | 2005054202 | 6/2005 |
| WO | 2005074535 | 8/2005 |
| WO | 2005087226 | 9/2005 |

(Continued)

OTHER PUBLICATIONS

Silverman, R. "The Organic Chemistry of Drug Design and Drug Action," 2004, Elsevier, pp. 29-32.*

(Continued)

*Primary Examiner* — Heidi Reese
(74) *Attorney, Agent, or Firm* — Scully, Scott, Murphy & Presser, P.C.

(57) ABSTRACT

The invention relates to 6-substituted isoquinoline derivatives of the formula (I)

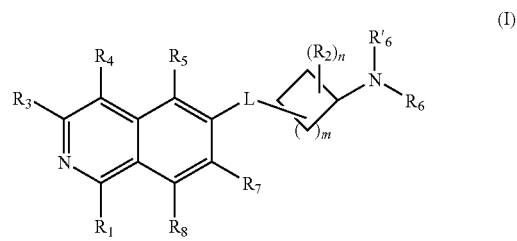

useful for the treatment and/or prevention of diseases associated with Rho-kinase and/or Rho-kinase mediated phosphorylation of myosin light chain phosphatase, and compositions containing such compounds.

46 Claims, No Drawings

(56) References Cited

FOREIGN PATENT DOCUMENTS

| WO | 2005095362 | | 10/2005 |
|---|---|---|---|
| WO | WO 2007/000240 | | 1/2007 |
| WO | 2007012421 | A1 | 2/2007 |
| WO | WO 2007/012422 | | 2/2007 |
| WO | WO 2007012422 | A1 * | 2/2007 |
| WO | 2007039563 | A1 | 4/2007 |
| WO | WO 2007/065916 | | 6/2007 |
| WO | 2008020081 | A1 | 2/2008 |
| WO | WO 2008/020081 | | 2/2008 |
| WO | WO 2008020081 | A1 * | 2/2008 |
| WO | 2008077555 | A2 | 7/2008 |
| WO | 2008077556 | A1 | 7/2008 |

OTHER PUBLICATIONS

U.S. Appl. No. 11/961,193, filed Dec. 20, 2007, Plettenburg, et al.
U.S. Appl. No. 12/019,866, filed Jan. 25, 2008, Plettenburg, et al.
U.S. Appl. No. 12/019,799, filed Jan. 25, 2008, Plettenburg, et al.
U.S. Appl. No. 12/487,479, filed Jun. 18, 2009, Plettenburg, et al.
U.S. Appl. No. 12/487,455, filed Jun. 18, 2009, Plettenburg, et al.
U.S. Appl. No. 12/487,525, filed Jun. 18, 2009, Plettenburg, et al.
U.S. Appl. No. 12/487,403, filed Jun. 18, 2009, Plettenburg, et al.
U.S. Appl. No. 12/487,409, filed Jun. 18, 2009, Plettenburg, et al.
U.S. Appl. No. 12/487,503, filed Jun. 18, 2009, Plettenburg, et al.
Ai, S., et. al., Rho-Rho Kinase Is Involved in Smooth Muscle Cell Migration Through Myosin Light Chain Phosphorylation-Dependent and Independent Pathways, Atherosclerosis, vol. 155, pp. 321-327, (2001).
Amano, M., et. al., Formation of Actin Stress Fibers and Focal Adhesions Enhanced by Rho-Kinase, Science, vol. 275, pp. 1308-1311, (1997).
Bauer, M., et. al., Dichotomous Regulation of Myosin Phosphorylation and Shape Change by Rho-Kinase and Calcium in Intact Human Platelets, Blood, vol. 94, No. 5, (1999), pp. 1665-1672.
Chellaiah, M., et. al., Rho-Dependent Rho Kinase Activation Increases CD44 Surface Expression and Bone Resorption in Osteoclasts, The Journal of Biological Chemistry. vol. 278, No. 31, (2003), pp. 29086-29097.
Chitaley, K., et. al., Antagonism of Rho-Kinase Stimualates Rat Penile Erection Via a Nitric Oxide-Independent Pathway, Nature Medicine, vol. 7, No. 1, (2001), pp. 119-122.
Demiryurek, S., et. al., Effects of Fasudil, a Rho-Kinase Inhibitor, On Myocardial Preconditioning in Anesthetized Rats, European Journal of Pharmacology, vol. 527, (2005), pp. 129-140.
Fukumoto, Y., et. al., Acute Vasodilator Effects of a Rho-Kinase Inhibitor, Fasudil, in Patelents With Severe Pulmonary Hypertension, Heart, (2005), vol. 91, pp. 391-392.
Furukawa, N., et. al., Role of Rho-Kinase in Regulation of Insulin Action and Glucose Homeostasis, Cell Metabolism, vol. 2, pp. 119-129, (2005).
Gingras, D., et. al., Tyrosine Phosphorylation of the Vascular Endothelial-Growth-Factor Receptor-2 (VEGFR-2) is Modulated by Rho Proteins, Biochem. J., (2000), vol. 348, pp. 273-280.
Gokina, N. I., et. al., Effects of Rho Kinase Inhibition on Cerebral Artery Myogenic Tone and Reactivity, J. Appl. Physiol. vol. 98, pp. 1940-1948, (2005).
Hara, M., et. al., Protein Kinase Inhibition by Fasudil Hydrochloride Promotes Neurological Recovery After Spinal Cord Injury in Rats, J Neurosurg. (Spine 1), vol. 93, pp. 94-101, (2000).
Hattori, T., et. al., Long-Term Inhibition of Rho-Kinase Suppresses Left Ventricular Remodeling After Myocardial Infarction in Mice, Circulation, (2004), vol. 109, pp. 2234-2239.
Okada, H., et. al., Synthesis and Antitumor Activities of Prodrugs of Benzoylphenylureas. Chem. Pharm. Bull (1994), pp. 57-61, vol. 42, No. 1.
Hitomi, A., et. al., Hemorheological Abnormalities in Experimental Cerebral Ischemia and Effects of Protein Kinase Inhibitor on Blood Fluidity, Life Sciences, vol. 67, (2000), pp. 1929-1939.
Honjo, M., et. al., Effects of Rho-Associated Protein Kinase Inhibitors Y-27632 on Intraocular Pressure and Outflow Facitlity, Investigative Ophthalmology & Visual Science, (2001), vol. 42, No. 1, pp. 137-144.
Inoue, M., et. al., Initiation of Neuropathic Pain Requires Lysophospatidic Acid Receptor Signaling, Nature Medicine, vol. 10, No. 7, pp. 712-718, (2004).
Itoh, et. al., An Essential Part for Rho-Associated Kinase in the Transcellular Invasion of Tumor Cells, Nature Medicine, vol. 5, No. 2, pp. 221-225, (1999).
Kawaguchi, A., et. al., The Effect of a Rho Kinase Inhibitor Y-27632 on Superoxide Production, Aggregation and Adhesion in Human Polymorphonuclear Leukocytes, European Journal of Pharmacology, vol. 403, (2000), pp. 203-208.
Kim, I., et. al., Thin and Thick Filament Regulation of Contractility in Experimental Cerebral Vasospasm, Neurosurgery, vol. 46, No. 2, (2000), pp. 440-447.
Kimura, K., et. al., Regulation of the Association of Adducin With Actin Filaments by Rho-Associated Kinase (Rho-Kinase) and Myosin Phosphatase, The Journal of Biological Chemistry, vol. 273, No. 10, pp. 5542-5548, (1998).
Kishi, T., et. al., Rho-Kinase Inhibitor Improves Increased Vascular Resistance and Imparied Vasodiation of the Forearm in Patients With Heart Failure. Circulation, (2005), vol. 111, pp. 2741-2747.
Klages, B., et. al., Activation of G12/G13 Results in Shape Change and Rho/Rho-Kinase-Mediated Myosin Light Chain Phosphorylation in Mouse Platelets, The Journal of Cell Biology, vol. 144, No. 4, (1999), pp. 745-754.
Lin, T., et. al., Rho-ROCK-LIMK-Cofilin Pathway Regulates Shear Stress Activation of Sterol Regulatory Element Binding Proteins, Circulation Research, (2003), vol. 92, pp. 1296-1304.
Maruoka, S., et. al., Elastase Anti-Elastase Imbalance in the Pathogenesis of COPD, Nippon Rinsho. (1999), vol. 57, pp. 1982-1987.
Masumoto, A. et. al., Suppression of Coronary Artery Spasm by the Rho-Kinase Inhibitor Fasudil in Patients With Vasospastic Angina, Circulation, (2002), vol. 105, pp. 1545-1547.
Nakahara, T., et. al., Y-27632 Potentiates Relaxant Effects of B2-Adrenoceptor Agonists in Bovine Tracheal Smooth Muscle, European Journal of Pharmacology, vol. 389, (2000), pp. 103-106.
Negoro, N., et. al., The Kinase Inhibitor Fasudil (HA-1077) Reduces Intimal Hyperplasia through Inhibiting Migration and Enhancing Cell Loss of Vascular Smooth Muscle Cells, Biochemical and Biophysical Research Communications, vol. 262, pp. 211-215, (1999).
Noma, K., et. al., Physiological Role of ROCKS in the Cardiovascular System, Am. J. Physiol. Cell Physiol., vol. 290, pp. C661-C668, (2006).
Pacaud, P., et. al., Rho Proteins and Vascular Diseases, Archives Des Maladies Du CCeur Et Des Vaisseaux, vol. 98, pp. 249-254, (2005).
Tamura, M., et. al., Development of Specific Rho-Kinase Inhibitors and Their Clinical Application, Biochimica et Biophysica Acta, (2005), vol. 1754, pp. 245-252.
Retzer, M., et. al., Lysophosphatidic Acid-Induced Platelet Shape Change Proceeds Via Rho/Rho Kinase-Mediated Myosin Light-Chain and Moesin Phosphorylation, Cellular Signalling, vol. 12, pp. 645-648, (2000).
Retzer, M., et. al., Mildly Oxidised Low Density Lipoprotein Induces Platelet Shape Change Via Rho-Kinase-Dependent Phosphorylation of Myosin Light Chain and Moesin, FEBS Letters, vol. 466, pp. 70-74, (2000).
Sandu, O. A., et. al., Diabetes in the Goto-Kakizaki Rat Is Accompanied by Impaired Insulin-Mediated Myosin-Bound Phosphatase Activation and Vascular Smooth Muscle Cell Relaxation, Diabetes, vol. 49, (2000), pp. 2178-2189.
Sato, M., et. al., Involvement of Rho-Kinase-Mediated Phosphorylation of Myosin Light Chain in Enhancement of Cereberal Vasospasm, Circulation Research, (2000), vol. 87, pp. 195-200.
Satoh, S.-I., et. al., Pharmacological Profile of Hydroxy Fasudil as a Selective Rho Kinase Inhitor on Ischemic Brain Damage, Life Sciences, vol. 69, (2001), pp. 1441-1453.
Seasholtz, T. M., et. al., Rho and Rho Kinase Mediate Thrombin-Stimulated Vascular Smooth Muscle Cell DNA Synthesis and Migration, Circulation Research, (1999), vol. 84, pp. 1186-1193.

(56) References Cited

OTHER PUBLICATIONS

Setoguchi, H., et. al., Leukotriene C4 Enhances the Contraction of Porcine Tracheal Smooth Muscle Through the Activation of Y-27632, a Rho Kinase Inhibitor, Sensitive Pathway, British Journal of Pharmacology, (2001), vol. 132, pp. 111-118.
Shimokawa, H., et. al., Anti-Anginal Effect of Fasudil, a Rho-Kinase Inhibitor, In Patients With Stable Effort Angina: A Multicenter Study, Journal of Cardiovascular Pharmacology, (2002), vol. 40, pp. 751-761.
Somlyo, A. V., et. al., Rho-Kinase Inhibitor Retards Migration and In Vivo Dissemination of Human Prostate Cancer Cells, Biochemical and Biophysical Research Communications, vol. 269, pp. 652-659, (2000).
Steioff, K., et. al., Long Term Rho-Kinase Inhibition Ameliorates Dysfunction in LDL-Receptor Deficient Mice, European Journal of Pharmacology, vol. 512, (2005), pp. 247-249.
Tatsumi, S., et. al., Involvement of Rho-Kinase in Inflammatory and Neuropathic Pain Through Phosphorylation of Myristoylated Alainine-Rich C-Kinase Substrate (MARCKS), Neuroscience, vol. 131, pp. 491-498, (2005).
Totsukawa, G., et. al., Distinct Roles of ROCK (Rho-Kinase) and MLCK in Spatial Regulation of MLC Phosphorylation for Assembly of Stress Fibers and Focal Adhesions in 3T3 Fibroblasts, The Journal of Cell Biology, vol. 150, No. 4, pp. 797-806, (2000).
Uchida, S., et. al., The Suppression of Small GTPase Rho Signal Transduction Pathway Inhibits Angiogenesis in Vitro and in Vivo, Biochemical and Biophysical Research Communications, vol. 269, pp. 633-640, (2000).
Uehata, M., et. al., Calcium Sensitization of Smooth Muscle Mediated by a Rho-Associated Protein Kinase in Hypertension, Nature, vol. 389, pp. 990-994, (1997).
Vicente-Manzanares, M., et. al., A Role for the Rho-p160 Rho Coiled-Coil Kinase Axis in the Chemokine Stromal Cell-Derived Factor-1a-Induced Lymphocyte Actomyosin and Microtubular Organization and Chemotaxis, The Journal of Immunology, (2002), vol. 168, pp. 400-410.
Vicente-Manzanares, M., et. al., The RhoA Effector MDia Is Induced During T Cell Activation and Regulates Actin Polymerization and Cell Migration in T Lymphocytes, The Journal of Immunology, (2003), vol. 171, pp. 1023-1034.
Wakino, S., et. al., Rho/Rho Kinase as a Potential Target for the Treatment of Renal Disease, Drug News Perspective, (2005), vol. 18, pp. 639-643.
Yamakawa, T., et. al., Involvement of Rho-Kinase in Angiotensin II-Induced Hypertrophy of Rat Vascular Smooth Muscle Cells, Hypertension, (2000), vol. 35, pp. 313-318.
Yamamoto, Y., et. al., The Protein Kinase Inhibitor Fasudil Protects Against Ischemic Myocardial Injury Induced by Endothelin-1 in the Rabbit, Journal of Cardiovascular Pharmacology, vol. 35, pp. 203-211, (2000).
Yoshida, Y., et. al., Studies on Anti-Helicobacter pylori Agents. Part 1: Benzyloxyisoquinoline Derivatives, Bioorg. & Med. Chem., vol. 7 (1999), pp. 2647-2666.
Yoshii, A., et. al., Relaxation of Contracted Rabbit Tracheal and Human Bronchial Smooth Muscle by Y-27632 Through Inhibition of Ca2+ Sensitization, Am. J. Resp. Cell Mol. Biol., vol. 20, pp. 1190-1200, (1999).
Zhou, Y., et. al., Nonsteroidal Anti-Inflammatory Drugs Can Lower Amyloidogenic AB42 by Inhibiting Rho, Science, vol. 302, pp. 1215-1217, (2003).
Pommereau, A., et. al., Two Simple and Generic Antibody-Independent Kinase Assays: Comparison of a Bioluminescent and a Microfluidic Assay Format, J. Biomol. Screen, (2004), vol. 9, pp. 409-416.
Alvarez, M. et al., "Product Class 5: Isoquinolines" Science of Synthesis (2005) pp. 661-838, vol. 15.
Alvarez, M. et al., "Product Class 6: Isoquinolines" Science of Synthesis (2005) pp. 839-890, vol. 15.
Remington's Pharmaceutical Sciences 17th Edition (1985), p. 1418.
Forzato, C. et al., "Baker's yeast reduction of 4-hetero-2-(2-nitroethyl)cyclohexanones" Tetrahedron: Asymmetry (1997) pp. 1811-1820, vol. 8.
U.S. Appl. No. 12/970,376, filed Dec. 16, 2010, Inventor: Plettenburg, et al, entitled: "6-Substituted Isoquinolines and Isoquinolinones".
U.S. Appl. No. 13/000,754, filed Apr. 20, 2011, Inventor: Plettenburg et al., entitled: "Substituted Isoquinolines and Isoquinolinones as Rho Kinase Inhibitors".
U.S. Appl. No. 13/000,202, filed Dec. 20, 2010, Inventor: Plettenburg et al., entitled: "Bi- and Polycyclic Substituted Isoquinoline and Isoquinolinone Derivatives".
Bonjoch, J. et al., "A New Synthetic Entry to the Tricyclic Skeleton of FR901483 by Palladium-Catalyzed Cyclization of Vinyl Bromides with Ketone Enolates" Tetrahedron Letters (2003) pp. 8387-8390, vol. 44.
Takami, A. et al., "Design and Synthesis of Rho Kinase Inhibitors (I)" Bioorganic & Medicinal Chemistry (2004) pp. 2115-2137, vol. 12.
Iwakubo, M. et al., "Design and Synthesis of Rho Kinase Inhibitors (III)" Bioorganic & Medicinal Chemistry (2007) pp. 1022-1033, vol. 15.
Iwakubo, M. et al., "Design and Synthesis of Rho Kinase Inhibitors (II)" Bioorganic & Medicinal Chemistry (2007) pp. 350-364, vol. 15.
Becker, D.P. et al., "A Short Synthesis of 1-Azaadamantan-4-one and the 4r and 4s Isomers of 4-Amino-1-azaadamantane" Synthesis (1992) pp. 1080-1082, vol. 11.
Degraffenreid, M.R. et al., "An Efficient and Scalable One-Pot Double Michael Addition-Dieckmann Condensation for the Synthesis of 4,4-Disubstituted Cyclohexane β-Keto Esters" Journal of Organic Chemistry (2007) pp. 7455-7458, vol. 72.
Lednicer, D. et al., "4-Amino-4-arylcyclohexanones and Their Derivatives, a Novel Class of Analgesics. 1. Modification of the Aryl Ring" Journal of Medicinal Chemistry (1980) pp. 424-430, vol. 23.
Caron, S. et al., "The Synthesis of a Selective PDE4/TNFα Inhibitor" Organic Process Research and Development (2001) pp. 587-592, vol. 5.
Curran, T. T., et al., "The Preparation of Optically Active 2-Cyclopentan-1, 4-Diol Derivatives from Furfurl Alcohol", Tetrahedron, pp. 1983-2004, vol. 53(6), Feb. 10, 1997.

\* cited by examiner

CYCLOALKYLAMINE SUBSTITUTED ISOQUINOLINE DERIVATIVES

FIELD OF THE INVENTION

The present invention relates to novel isoquinoline derivatives as described in the claims, their preparation and their use in the treatment and/or prevention of diseases related to the inhibition of Rho-kinase and/or of Rho-kinase mediated phosphorylation of myosin light chain phosphatase.

BACKGROUND OF THE INVENTION

Activation of a small GTPase RhoA upon agonist stimulation results in conversion of RhoA from the inactive GDP-bound form to the active GTP-bound form with a subsequent binding to and activation of Rho-kinase. Two isoforms, Rho-kinase 1 and Rho-kinase 2, are known. Rho-kinase 2 is expressed in vascular smooth muscle cells and endothelial cells. Activation of Rho-kinase 2 by the active GTP-bound RhoA leads to calcium sensitization of smooth muscle cells through phosphorylation-mediated inhibition of the myosin light chain phosphatase activity and thereby up-regulation of the activity of myosin regulatory light chain (Uehata et al., Nature 1997, 389, 990-994).

It is known that Rho-kinase is involved in vasoconstriction, including the development of myogenic tone and smooth muscle hypercontractility (Gokina et al. J. Appl. Physiol. 2005, 98, 1940-8), bronchial smooth muscle contraction (Yoshii et al. Am. J. Resp. Cell Mol. Biol. 20, 1190-1200), asthma (Setoguchi et al. Br J Pharmacol. 2001, 132, 111-8; Nakahara, et al. Eur J 2000, 389, 103) and chronic obstructive pulmonary disease (COPD, Maruoka, Nippon Rinsho, 1999, 57, 1982-7), hypertension, pulmonary hypertension (Fukumoto et al. Heart, 91, 391-2, 2005, Mukai et al. Nature 1997, 389, 990-4) and ocular hypertension and regulation of intraocular pressure (Honjo et al. Invest. Opthalmol. Visual Sci. 2001, 42, 137-144), endothelial dysfunction (Steioff et al. Eur. J. Pharmacol. 2005, 512, 247-249), angina (Masumoto et al. Circ 2002, 105, 1545-47, Shimokawa et al. JCP, 2002, 40, 751-761), nephropathy, including hypertension-induced, non-hypertension-induced, and diabetic nephropathies, renal failure and peripheral arterial occlusive disease (PAOD) (Wakino et al. Drug News Perspect. 2005, 18, 639-43), myocardial infarction (Demiryurek et al. Eur J. Pharmacol. 2005, 527, 129-40, Hattori et al. Circulation, 2004, 109, 2234-9), cardiac hypertrophy and failure (Yamakawa, et al. Hypertension 2000, 35, 313-318, Liao et al. Am J Physiol Cell Physiol. 2006, 290, C661-8, Kishi et al. Circ 2005, 111, 2741-2747), coronary heart disease, atherosclerosis, restenosis (Pacaud et al. Arch. Mal. Coeur 2005, 98, 249-254, Retzer, et al. FEBS Lett 2000, 466, 70, Negoro, et al. Biochem Biophys Res Commun 1999, 262, 211), diabetes, diabetic complications, glucose utilization and metabolic syndrome (Sandu, et al. Diabetes 2000, 49, 2178, Maeda et al. Cell Metab. 2005, 2, 119-29), sexual dysfunction, e.g., penile erectile dysfunction (Chitaley et al. Nature Medicine 2001, 7, 119-122), retinopathy, inflammation, immune diseases, AIDS, osteoporosis, endocrine dysfunctions, e.g. hyperaldosteronism, central nervous system disorders such as neuronal degeneration and spinal cord injury (Nara, et al. J Neurosurg 2000, 93, 94), cerebral ischemia (Uehata, et al. Nature 1997, 389, 990; Satoh et al. Life Sci. 2001, 69, 1441-53; Hitomi, et al. Life Sci 2000, 67, 1929; Yamamoto, et al. J Cardiovasc Pharmacol. 2000, 35, 203-11), cerebral vasospasm (Sato, et al. Circ Res 2000, 87, 195; Kim, et al. Neurosurgery 2000, 46, 440), pain, e.g. neuropathic pain (Tatsumi, et al. Neuroscience 2005, 131, 491, Inoue, et al. Nature medicine 2004, 10, 712), infection of digestive tracts with bacteria (WO 98/06433), cancer development and progression, neoplasia where inhibition of Rho kinase has been shown to inhibit tumor cell growth and metastasis (Itoh, et al. Nature Medicine 1999, 5, 221; Somlyo, et al. Res Commun 2000, 269, 652), angiogenesis (Uchida, et al. Biochem Biophys Res 2000, 269, 633-40; Gingras, et al. Biochem J 2000, 348, 273), vascular smooth muscle cell proliferation and motility (Tammy et al. Circ. Res. 1999, 84, 1186-1193; Tangkijvanich et al. Atherosclerosis 2001, 155, 321-327), endothelial cell proliferation, endothelial cell retraction and motility (Oikawa et al. Biochem. Biophys. Res. Commun. 2000, 269, 633-640), stress fiber formation (Kimura et al. Science 1997, 275, 1308-1311; Yamashiro et al. J. Cell Biol. 2000, 150, 797-806), thrombotic disorders (Kikkawa, et al. FEBS Lett. 2000, 466, 70-74; Bauer et al. Blood 1999, 94, 1665-1672, Klages, et al. J Cell Biol 1999, 144, 745; Retzer, et al. Cell Signal 2000, 12, 645) and leukocyte aggregation (Kawaguchi, et al. Eur J. Pharmacol. 2000, 403:203-8; Sanchez-Madrid, et al. J. Immunol. 2003, 171:1023-34, Sanchez-Madrid, et al. J. Immunol. 2002, 168:400-10), and bone resorption (Chellaiah, et al. J Biol. Chem. 2003, 278:29086-97). Na/H exchange transport system activation (Kawaguchi, et al. Eur J. Pharmacol. 2000, 403:203-8), Alzheimer's disease (Zhou et al. Science 2003, 302, 1215-1217), adducin activation (Fukata et al. J. Biol. Chem., 1998, 273, 5542-5548), and in SREB (Sterol response binding element) signalling and its effects on lipid metabolism (Lin et al. Circ. Res., 92, 1296-304, 2003).

Therefore, a compound having inhibitory effect on Rho-kinase and/or on Rho-kinase mediated phosphorylation of myosin light chain phosphatase is useful for the treatment and/or prevention of cardiovascular and non-cardiovascular diseases involving Rho-kinase as the primary or secondary disease cause, like hypertension, pulmonary hypertension, ocular hypertension, retinopathy, and glaucoma, peripheral circulatory disorder, peripheral arterial occlusive disease (PAOD), coronary heart disease, angina pectoris, heart hypertrophy, heart failure, ischemic diseases, ischemic organ failure (end organ damage), fibroid lung, fibroid liver, liver failure, nephropathy, including hypertension-induced, non-hypertension-induced, and diabetic nephropathies, renal failure, fibroid kidney, renal glomerulosclerosis, organ hypertrophy, asthma, chronic obstructive pulmonary disease (COPD), adult respiratory distress syndrome, thrombotic disorders, stroke, cerebral vasospasm, cerebral ischemia, pain, e.g. neuropathic pain, neuronal degeneration, spinal cord injury, Alzheimer's disease, premature birth, erectile dysfunction, endocrine dysfunctions, arteriosclerosis, prostatic hypertrophy, diabetes and complications of diabetes, metabolic syndrome, blood vessel restenosis, atherosclerosis, inflammation, autoimmune diseases, AIDS, osteopathy such as osteoporosis, infection of digestive tracts with bacteria, sepsis, cancer development and progression, e.g. cancers of the breast, colon, prostate, ovaries, brain and lung and their metastases.

WO 01/64238 describes isoquinoline-5-sulfonamide derivatives optionally substituted by a —$(CH_2)_{1-6}$—O—$(CH_2)_{0-6}$—, a —$(CH_2)_{0-6}$—S—$(CH_2)_{0-6}$— or a —$(CH_2)_{0-6}$-linked heterocyclic group useful as neuroprotective agents.

WO 2004/106325 (Schering AG) describes prodrugs of the Rho-kinase inhibitor fasudil carrying an ether or ester group in the 1-position of the isoquinoline ring.

WO 2001/039726 generically describes —O—($C_0$-$C_{10}$) alkyl-heteroaryl substituted cyclohexyl derivatives useful for the treatment of microbial infections.

JP 10087629 A describes isoquinoline derivatives useful for the treatment of diseases caused by *Heliobacter pylori* such as for example gastritis cancer or ulcer. The isoquinoline derivatives may be substituted by OH in the 1-position and are preferably 5-substituted by X—[($C_1$-$C_6$)alkylene)]$_{0-1}$—Y wherein X may be oxygen and Y may be an aryl or a heterocyclic group.

Hagihara et al. (Bioorg. Med. Chem. 1999, 7, 2647-2666) disclose 6-benzyloxy-isoquinoline for the treatment of infections caused by *Heliobacter pylori*.

U.S. Pat. No. 5,480,883 generically discloses as EGF and/or PDGF receptor inhibitors useful for inhibiting cell proliferation compounds of the formula "Ar I—X—Ar II" wherein X may be $(CHR_1)_m$—Z—$(CHR_1)_n$, e.g. Z—$CH_2$, wherein Z may be O, $R_1$ is hydrogen or alkyl, Ar I may be among others an optionally substituted isoquinolone and Ar II may be among others an optionally substituted $C_{3-7}$ monocyclic saturated heterocyclic system.

WO 2005/030791 (Merck & Co.) generically describes as potassium channel inhibitors for the treatment of cardiac arrhythmias, stroke, congestive heart failure etc. isoquinolone derivatives which are optionally substituted in 6-position by a group $(CR^eR^f)_pOR^{43}$ wherein p may be zero, and $R^{43}$ is e.g. a ($C_3$-$C_{10}$)cycloalkyl residue optionally substituted by $NR^{51}R^{52}$, wherein $R^{51}$ and $R^{52}$ may be hydrogen, ($C_1$-$C_6$) alkyl etc.; or $R^{43}$ is a group $R^{81}$ defined as a 4-6 membered unsaturated or saturated monocyclic heterocylic ring with 1, 2, 3 or 4 heteroatoms; and are substituted by a directly bound optionally substituted aryl or heteroaryl ring in the 4-position.

WO 2005/030130 (Merck & Co.) generically describes as potassium channel inhibitors for the treatment of cardiac arrhythmias, stroke, congestive heart failure etc. isoquinoline derivatives which may be substituted by hydroxyl in the 1-position and are optionally substituted in 6-position by a group $(CR^eR^f)_pOR^{43}$ wherein p may be zero, and $R^{43}$ is e.g. a ($C_3$-$C_{10}$)cycloalkyl residue optionally substituted by $NR^{51}R^{52}$, wherein $R^{51}$ and $R^{52}$ may be hydrogen, ($C_1$-$C_6$)alkyl etc.; or $R^{43}$ is a group $R^{81}$ defined as a 4-6 membered unsaturated or saturated monocyclic heterocyclic ring with 1, 2, 3 or 4 heteroatoms; and are substituted by a directly bound optionally substituted aryl or heteroaryl ring in the 4-position.

WO 03/053330 (Ube) generically describes isoquinolone derivatives of the formula

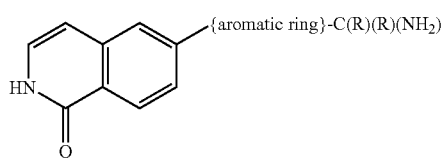

as Rho-kinase inhibitors.

SUMMARY OF THE INVENTION

An embodiment of the present invention is a compound of the formula (I)

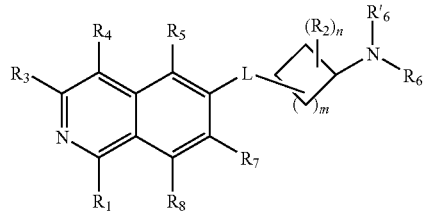

wherein
$R_1$ is
H,
($C_1$-$C_6$)alkyl,
R',
NH—($C_1$-$C_6$)alkyl,
NHR', or
N[($C_1$-$C_6$)alkyl]$_2$;
$R_2$ is H, halogen or ($C_1$-$C_6$)alkyl;
$R_3$ is
H,
halogen,
($C_1$-$C_6$)alkyl,
($C_1$-$C_6$)alkylene-R',
OH,
O—R",
$NH_2$,
NHR",
NR"R" or
NH—C(O)—R",
$R_4$ is
H,
halogen,
hydroxy,
CN,
($C_1$-$C_6$)alkyl,
R',
($C_1$-$C_6$)alkylene-R';
$R_5$ is
H,
halogen,
CN,
$NO_2$,
($C_1$-$C_6$)alkyl,
($C_2$-$C_6$)alkenyl,
R',
($C_1$-$C_6$)alkylene-($C_6$-$C_{10}$)aryl,
($C_2$-$C_6$)alkenylene-($C_6$-$C_{10}$)aryl,
($C_1$-$C_6$)alkylene-($C_5$-$C_{10}$)heterocyclyl,
CH(OH)—($C_1$-$C_6$)alkyl,
$NH_2$,
NH—R',
NH—$SO_2$H,
NH—$SO_2$—($C_1$-$C_6$)alkyl,
NH—$SO_2$—R',
NH—C(O)—($C_1$-$C_6$)alkyl,
NH—C(O)—R',
C(O)N[($C_1$-$C_6$)alkyl]$_2$,
C(O)OH, or
C(O)O—($C_1$-$C_6$)alkyl;
$R_6$ and $R_6$' are independently of each other
H,
R',
($C_1$-$C_8$)alkyl,
($C_1$-$C_6$)alkylene-R', $(C_1-C_6)$alkylene-O—$(C_1-C_6)$alkyl,
$(C_1-C_6)$alkylene-O—R',
$(C_1-C_6)$alkylene-CH[R']$_2$,
$(C_1-C_6)$alkylene-C(O)—R',
$(C_1-C_6)$alkylene-C(O)NH$_2$,
$(C_1-C_6)$alkylene-C(O)NH—R',
$(C_1-C_6)$alkylene-C(O)NH—$(C_1-C_6)$alkyl,
$(C_1-C_6)$alkylene-C(O)N[$(C_1-C_6)$alkyl]$_2$,
$(C_1-C_6)$alkylene-C(O)N[R']$_2$;
$(C_1-C_6)$alkylene-C(O)O—$(C_1-C_6)$alkyl,
C(O)O—$(C_1-C_6)$alkyl,
C(O)OR'
C(O)($C_1-C_6$)alkyl,
C(O)R',
C(O)NH—$(C_1-C_6)$alkyl,
C(O)NHR',
C(O)N[$(C_1-C_6)$alkyl]R'
C(O)N[$(C_1-C_6)$alkyl]$_2$,
C(O)—$(C_1-C_6)$alkylene-R',
C(O)O($C_1-C_6$)alkylene-R',
or R$_6$ and R$_6$', together with the N-atom to which they are attached, form a $(C_5-C_{10})$ heterocyclyl group;
R$_7$ is
H,
halogen,
CN,
NO$_2$,
$(C_1-C_6)$alkyl,
O—$(C_1-C_6)$alkyl,
$(C_2-C_6)$alkenyl,
R',
$(C_2-C_6)$alkenylene-$(C_6-C_{10})$aryl,
$(C_1-C_6)$alkylene-R',
CH(OH)—$(C_1-C_6)$alkyl,
NH$_2$,
NH—R',
NH—SO$_2$H,
NH—SO$_2$—$(C_1-C_6)$alkyl,
NH—SO$_2$—R',
SO$_2$—NH$_2$,
SO$_2$—NHR',
NH—C(O)—$(C_1-C_6)$alkyl,
NH—C(O)—R',
C(O)N[$(C_1-C_6)$alkyl]$_2$,
C(O)OH, or
C(O)O—$(C_1-C_6)$alkyl;
R$_8$ is H, halogen or $(C_1-C_6)$alkyl;
n is 1, 2, 3 or 4;
m is 1, 2, 3, 4 or 5, and
L is O or O—$(C_1-C_6)$alkylene;
R' is
$(C_3-C_8)$cycloalkyl,
$(C_5-C_{10})$heterocyclyl,
$(C_6-C_{10})$aryl; and
R" is
$(C_3-C_8)$cycloalkyl,
$(C_5-C_{10})$heterocyclyl,
$(C_6-C_{10})$aryl,
$(C_1-C_6)$alkyl,
$(C_1-C_6)$alkylene-R',
$(C_1-C_6)$alkylene-O—$(C_1-C_6)$alkyl,
$(C_1-C_6)$alkylene-O—R', or
$(C_1-C_6)$alkylene-NR$_x$R$_y$; and
R$_x$ and R$_y$ are independently of each other
$(C_1-C_6)$alkyl,
$(C_5-C_{10})$heterocyclyl,
$(C_6-C_{10})$aryl,
$(C_1-C_4)$alkylene-$(C_5-C_{10})$heterocyclyl,
$(C_1-C_4)$alkylene-$(C_6-C_{10})$aryl,
$(C_1-C_4)$alkylene-NH$(C_1-C_6)$alkyl,
$(C_1-C_4)$alkylene-N[$(C_1-C_6)$alkyl]$_2$,
$(C_1-C_4)$alkylene-N[$(C_6-C_{10})$aryl]$_2$, or
$(C_1-C_4)$alkylene-N[$(C_5-C_{10})$heterocyclyl]$_2$;
wherein in residues R$_4$, R$_5$, R$_6$, R$_6$', R$_7$ and R$_8$ as alkyl, alkylene or cycloalkyl can optionally be substituted one or more times by OH, OCH$_3$, COOH, COOCH$_3$, NH$_2$, NHCH$_3$, N(CH$_3$)$_2$, CONH$_2$, CONHCH$_3$ or CON(CH$_3$)$_2$;
wherein in residues R$_1$ to R$_8$ as alkyl or alkylene can optionally be substituted one or more times by halogen;
wherein in residues R$_1$ and R$_3$ to R$_8$ as $(C_6-C_{10})$aryl and $(C_5-C_{10})$heterocyclyl are unsubstituted or substituted one or more times by a suitable group independently selected from halogen, OH, NO$_2$, N$_3$, CN, C(O)—$(C_1-C_6)$alkyl, C(O)—$(C_6-C_{10})$aryl, COOH, COO$(C_1-C_6)$alkyl, CONH$_2$, CONH$(C_1-C_6)$alkyl, CON[$(C_1-C_6)$alkyl]$_2$, $(C_3-C_8)$cycloalkyl, $(C_1-C_6)$alkyl, $(C_1-C_6)$alkylene-OH, $(C_1-C_6)$alkylene-NH$_2$, $(C_1-C_6)$alkylene-NH$(C_1-C_6)$alkyl, $(C_1-C_6)$alkylene-N[$(C_1-C_6)$alkyl]$_2$, $(C_2-C_6)$alkenyl, $(C_2-C_6)$alkynyl, O—$(C_1-C_6)$alkyl, O—C(O)—$(C_1-C_6)$alkyl, PO$_3$H$_2$, SO$_3$H, SO$_2$—NH$_2$, SO$_2$NH$(C_1-C_6)$alkyl, SO$_2$N[$(C_1-C_6)$alkyl]$_2$, S—$(C_1-C_6)$alkyl, SO—$(C_1-C_6)$alkyl, SO$_2$—$(C_1-C_6)$alkyl, SO$_2$—N=CH—N[$(C_1-C_6)$alkyl]$_2$, C(NH)(NH$_2$), NH$_2$, NH—$(C_1-C_6)$alkyl, N[$(C_1-C_6)$alkyl]$_2$, NH—C(O)—$(C_1-C_6)$alkyl, NH—C(O)O—$(C_1-C_6)$alkyl, NH—SO$_2$—$(C_1-C_6)$alkyl, NH—SO$_2$—$(C_6-C_{10})$aryl, NH—SO$_2$—$(C_5-C_{10})$heterocyclyl, N$(C_1-C_6)$alkyl-C(O)—$(C_1-C_6)$alkyl, N$(C_1-C_6)$alkyl-C(O)O—$(C_1-C_6)$alkyl, N$(C_1-C_6)$alkyl-C(O)—NH—$(C_1-C_6)$alkyl], $(C_6-C_{10})$aryl, $(C_1-C_6)$alkylene-$(C_6-C_{10})$aryl, O—$(C_6-C_{10})$aryl, O—$(C_1-C_6)$alkylene-$(C_6-C_{10})$aryl, $(C_5-C_{10})$heterocyclyl, $(C_1-C_6)$alkylene-$(C_5-C_{10})$heterocyclyl, and O—$(C_1-C_6)$alkylene-$(C_5-C_{10})$heterocyclyl, wherein the $(C_6-C_{10})$aryl or $(C_5-C_{10})$heterocyclyl in the substituent may be substituted one to three times by a group independently selected from halogen, OH, NO$_2$, CN, O—$(C_1-C_6)$alkyl, $(C_1-C_6)$alkyl, NH$_2$, NH$(C_1-C_6)$alkyl, N[$(C_1-C_6)$alkyl]$_2$, SO$_2$CH$_3$, COOH, C(O)O—$(C_1-C_6)$alkyl, CONH$_2$, $(C_1-C_6)$alkylene-O—$(C_1-C_6)$alkyl, $(C_1-C_6)$alkylene-O—$(C_6-C_{10})$aryl, and O—$(C_1-C_6)$alkylene-$(C_6-C_{10})$aryl; or wherein $(C_6-C_{10})$aryl is vicinally substituted by a O—$(C_1-C_4)$alkylene-O group whereby a 5-8-membered ring is formed together with the carbon atoms the oxygen atoms are attached to; and wherein aryl substituent of $(C_6-C_{10})$aryl and $(C_6-C_{10})$heterocyclyl substituent groups may not be further substituted by an aryl or heterocyclyl containing group; or
pharmaceutically acceptable salt thereof.

DETAILED DESCRIPTION OF THE INVENTION

Definitions

The terms $(C_1-C_2)$alkyl, $(C_1-C_4)$alkyl, $(C_1-C_6)$alkyl, $(C_1-C_8)$alkyl and the corresponding alkylene substituents are understood as a hydrocarbon residue which can be linear, i.e. straight-chain, or branched and has 1, 2, 3, 4, 5, 6, 7 or 8 carbon atoms, respectively. This also applies if an alkyl group occurs as a substituent on another group, for example in an alkoxy group (O-alkyl), S-alkyl or a —O$(C_1-C_6)$alkylene-O—, an alkoxycarbonyl group or an arylalkyl group. Examples of alkyl groups are methyl, ethyl, propyl, butyl, pentyl or hexyl, the n-isomers of all these groups, isopropyl, isobutyl, 1-methylbutyl, isopentyl, neopentyl, 2,2-dimethylbutyl, 2-methylpentyl, 3-methylpentyl, isohexyl, sec-butyl, tert-butyl or tert-pentyl. Alkyl or alkylene groups may—if not otherwise stated— be halogenated once or more, e.g. alkyl groups may be fluorinated, e.g. perfluorinated. Examples of halogenated alkyl groups are $CF_3$ and $CH_2CF_3$, $OCF_3$, $SCF_3$, or —O—$(CF_2)_2$—O—.

Alkenyl are, for example, vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl.

Alkynyl are, for example, ethynyl, 1-propynyl, 2-propynyl (=propargyl) or 2-butynyl.

Halogen means fluoro, chloro, bromo or iodo.

$(C_3-C_8)$cycloalkyl groups are cyclic alkyl groups containing 3, 4, 5, 6, 7 or 8 ring carbon atoms like cyclopropyl, cyclobutyl, cyclopentyl, cyclohexyl or cyclooctyl, which can also be substituted and/or contain 1 or 2 double bounds (unsaturated cycloalkyl groups) like, for example, cyclopentenyl or cyclohexenyl can be bonded via any carbon atom.

A $(C_6-C_{10})$aryl group means an aromatic ring or a ring system which comprises two aromatic rings which are fused or otherwise linked, for example a phenyl, naphthyl, biphenyl, tetrahydronaphthyl, alpha- or beta-tetralon-, indanyl- or indan-1-on-yl group. A preferred $(C_6-C_{10})$aryl group is phenyl.

A $(C_5-C_{10})$heterocyclyl group means a mono- or bicyclic ring system in which one or more carbon atoms can be replaced by one or more heteroatoms such as, for example, 1, 2 or 3 nitrogen atoms, 1 or 2 oxygen atoms, 1 or 2 sulfur atoms or combinations of different hetero atoms. The heterocyclyl residues can be bound at any positions, for example on the 1-position, 2-position, 3-position, 4-position, 5-position, 6-position, 7-position or 8-position. $(C_5-C_{10})$heterocyclyl groups may be (1) aromatic [=heteroaryl groups] or (2) saturated or (3) mixed aromatic/saturated.

Suitable $(C_5-C_{10})$heterocyclyl group include acridinyl, azocinyl, benzimidazolyl, benzofuryl, benzomorpholinyl, benzothienyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, furanyl, quinazolinyl, quinolinyl, 4H-quinolizinyl, quinoxalinyl, quinuclidinyl, chromanyl, chromenyl, chromen-2-onyl, cinnolinyl, decahydroquinolinyl, 2H,6H-1,5,2-dithiazinyl, dihydrofuro[2,3-b]-tetrahydrofuran, furyl, furazanyl, homomorpholinyl, homopiperazinyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, benzimidazolyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathinyl, phenoxazinyl, phthalazinyl, piperazinyl, piperidinyl, prolinyl, pteridinyl, purynyl, pyranyl, pyrazinyl, pyroazolidinyl, pyrazolinyl, pyrazolyl, pyridazinyl, pyridonyl, pyridooxazoles, pyridoimidazoles, pyridothiazoles, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadiazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl and xanthenyl. Pyridyl stands both for 2-, 3- and 4-pyridyl. Thienyl stands both for 2- and 3-thienyl. Furyl stands both for 2- and 3-furyl. Also included are the corresponding N-oxides of these compounds, for example, 1-oxy-2-, 3- or 4-pyridyl.

Substitutions in $(C_5-C_{10})$heterocyclyl residues can occur on free carbon atoms or on nitrogen atoms.

Preferred examples of $(C_5-C_{10})$heterocyclyl residues are pyrazinyl, pyridyl, pyrimidinyl, pyrazolyl, morpholinyl, pyrrolidinyl, piperazinyl, piperidinyl, thienyl, benzofuryl, quinolinyl, tetrazolyl and triazolyl.

$(C_6-C_{10})$aryl and $(C_5-C_{10})$heterocyclyl groups are unsubstituted or, if not stated otherwise, substituted one or more times, preferably one to three times, by suitable groups independently selected from halogen, OH, $NO_2$, $N_3$, CN, C(O)—$(C_1-C_6)$alkyl, C(O)—$(C_6-C_{10})$aryl, COOH, COO$(C_1-C_6)$alkyl, $CONH_2$, CONH$(C_1-C_6)$alkyl, CON$[(C_1-C_6)$alkyl$]_2$, $(C_3-C_8)$cycloalkyl, $(C_1-C_6)$alkyl, $(C_1-C_6)$alkylene-OH, $(C_1-C_6)$alkylene-$NH_2$, $(C_1-C_6)$alkylene-NH$(C_1-C_6)$alkyl, $(C_1-C_6)$alkylene-N$[(C_1-C_6)$alkyl$]_2$, $(C_2-C_6)$alkenyl, $(C_2-C_6)$alkynyl, O—$(C_1-C_6)$alkyl, O—C(O)—$(C_1-C_6)$alkyl, $PO_3H_2$, $SO_3H$, $SO_2$—$NH_2$, $SO_2$NH$(C_1-C_6)$alkyl, $SO_2$N$[(C_1-C_6)$alkyl$]_2$, S—$(C_1-C_6)$alkyl; SO—$(C_1-C_6)$alkyl, $SO_2$—$(C_1-C_6)$alkyl, $SO_2$—N═CH—N$[(C_1-C_6)$alkyl$]_2$, C(NH)($NH_2$), $NH_2$, NH—$(C_1-C_6)$alkyl, N$[(C_1-C_6)$alkyl$]_2$, NH—C(O)—$(C_1-C_6)$alkyl, NH—C(O)O—$(C_1-C_6)$alkyl, NH—$SO_2$—$(C_1-C_6)$alkyl, NH—$SO_2$—$(C_6-C_{10})$aryl, NH—$SO_2$—$(C_5-C_{10})$heterocyclyl, N$(C_1-C_6)$alkyl-C(O)—$(C_1-C_6)$alkyl, N$(C_1-C_6)$alkyl-C(O)O—$(C_1-C_6)$alkyl, N$(C_1-C_6)$alkyl-C(O)—NH—$(C_1-C_6)$alkyl], $(C_6-C_{10})$aryl, $(C_1-C_6)$alkylene-$(C_6-C_{10})$aryl, O—$(C_6-C_{10})$aryl, O—$(C_1-C_6)$alkylene-$(C_6-C_{10})$aryl, $(C_5-C_{10})$heterocyclyl, $(C_1-C_6)$alkylene-$(C_5-C_{10})$heterocyclyl, O—$(C_1-C_6)$alkylene-$(C_5-C_{10})$heterocyclyl, wherein the $(C_6-C_{10})$aryl or $(C_5-C_{10})$heterocyclyl may be substituted one to 3 times by a group independently selected from halogen, OH, $NO_2$, CN, O—$(C_1-C_6)$alkyl, $(C_1-C_6)$alkyl, $NH_2$, NH$(C_1-C_6)$alkyl, N$[(C_1-C_6)$alkyl$]_2$, $SO_2CH_3$, COOH, C(O)O—$(C_1-C_6)$alkyl, $CONH_2$, $(C_1-C_6)$alkylene-O—$(C_1-C_6)$alkyl, $(C_1-C_6)$alkylene-O—$(C_6-C_{10})$aryl, O—$(C_1-C_6)$alkylene-$(C_6-C_{10})$aryl; or wherein $(C_6-C_{10})$aryl is vicinally substituted by a O—$(C_1-C_4)$alkylene-O group whereby a 5-8-membered ring is formed together with the carbon atoms the oxygen atoms are attached to. Aryl or heterocyclyl substituents of $(C_6-C_{10})$aryl and $(C_5-C_{10})$heterocyclyl groups may not be further substituted by an aryl or heterocyclyl containing group.

Preferred substituents for $(C_6-C_{10})$aryl groups are $(C_1-C_4)$alkyl, O—$(C_1-C_4)$alkyl, O-phenyl, phenyl, C(O)O—$(C_1-C_6)$alkyl, C(O)OH, C(O)—$(C_1-C_4)$alkyl, halogen, $NO_2$, $SO_2NH_2$, CN, $SO_2$—$(C_1-C_4)$alkyl, $SO_2$—N═CH—N$[(C_1-C_6)$alkyl$]_2$, NH—$SO_2$—$(C_1-C_4)$alkyl, $NH_2$, NH—C(O)—$(C_1-C_4)$alkyl, $(C_3-C_8)$cycloalkyl, $(C_1-C_4)$alkyl-OH, C(O)N$[(C_1-C_4)$alkyl$]_2$, CONH$(C_1-C_6)$alkyl, C(O)$NH_2$, N$[(C_1-C_4)$alkyl$]_2$, $(C_1-C_4)$alkylene-$(C_6-C_{10})$aryl, wherein the $(C_6-C_{10})$aryl may be further substituted one to three times, preferably once, by $(C_1-C_4)$alkyl, $(C_1-C_4)$alkylene-O—$(C_1-C_6)$alkyl, $(C_6-C_{10})$aryl, O—$(C_1-C_6)$alkyl-$(C_6-C_{10})$aryl, or may be vicinally substituted by a O—$(C_1-C_4)$alkylene-O group whereby a 5-8-membered ring is formed together with the carbon atoms the oxygen atoms are attached to. More preferred substituents for $(C_6-C_{10})$aryl are halogen, CN, phenyl, O-phenyl, NH—C(O)—$(C_1-C_4)$alkyl especially NH—C(O)—$CH_3$, C(O)—$(C_1-C_4)$alkyl especially C(O)—$CH_3$, C(O)—O$(C_1-C_4)$alkyl especially C(O)—$OCH_3$, $(C_1-C_4)$alkyl especially $CH_3$ or $CF_3$, O—$(C_1-C_4)$alkyl especially O—$CH_3$, $SO_2$—$NH_2$, $SO_2$—$(C_1-C_4)$alkyl especially $SO_2$—$CH_3$ or $SO_2$—$CF_3$; or $SO_2$—N═CH—N$[(C_1-C_4)$alkyl$]_2$ especially $SO_2$—N═CH—N$[(CH_3)_2$.

In monosubstituted phenyl groups the substituent can be located in the 2-position, the 3-position or the 4-position, with the 3-position and the 4-position being preferred. If a phenyl group carries two substituents, they can be located in 2,3-position, 2,4-position, 2,5-position, 2,6-position, 3,4-position or 3,5-position. In phenyl groups carrying three substituents the substituents can be located in 2,3,4-position, 2,3,5-position, 2,3,6-position, 2,4,5-position, 2,4,6-position, or 3,4,5-position.

The above statements relating to phenyl groups correspondingly apply to divalent groups derived from phenyl groups, i.e. phenylene which can be unsubstituted or substituted 1,2-phenylene, 1,3-phenylene or 1,4-phenylene. The above statements also correspondingly apply to the aryl subgroup in arylalkylene groups. Examples of arylalkylene groups which can also be unsubstituted or substituted in the aryl subgroup as well as in the alkylene subgroup, are benzyl, 1-phenylethylene, 2-phenylethylene, 3-phenylpropylene, 4-phenylbutylene, 1-methyl-3-phenyl-propylene.

Preferred substituents for $(C_5-C_{10})$heterocyclyl groups are $(C_1-C_4)$alkyl, O—$(C_1-C_4)$alkyl, $(C_1-C_4)$alkylene-phenyl, halogen, $(C_1-C_4)$alkylene-O—$(C_1-C_4)$alkyl, $(C_5-C_{10})$heterocyclyl, $(C_1-C_4)$alkylene-N[$(C_1-C_4)$alkyl]$_2$, or $(C_6-C_{10})$aryl, wherein the $(C_6-C_{10})$aryl may be further substituted by halogen, $(C_1-C_4)$alkyl, O—$(C_1-C_4)$alkyl, $(C_1-C_4)$alkylene-O—$(C_1-C_6)$alkyl, O—$(C_1-C_6)$alkyl-$(C_6-C_{10})$aryl, or may be vicinally substituted by a O—$(C_1-C_4)$alkylene-O group whereby a 5-8-membered ring is formed together with the carbon atoms the oxygen atoms are attached to. More preferred substituents for $(C_5-C_{10})$heterocyclyl groups are $(C_1-C_4)$alkyl, O—$(C_1-C_4)$alkyl, halogen or phenyl, wherein the phenyl may be further substituted one to three times, preferably once, by halogen, $(C_1-C_4)$alkyl or O—$(C_1-C_4)$alkyl.

The general and preferred substituents of $(C_6-C_{10})$aryl and $(C_5-C_{10})$heterocyclyl groups may be combined with the general and preferred definitions of $R_1$, $R_2$, $R_3$, $R_4$, $R_5$, $R_6$, $R_6'$, $R_7$, $R_8$, n, m and L as described above.

Embodiments

Preferably, $R_1$ is H, $(C_1-C_6)$alkyl, $(C_6-C_{10})$aryl, NH—$(C_1-C_6)$alkyl, NH—$(C_6-C_{10})$aryl or N[$(C_1-C_6)$alkyl]$_2$. More preferably, $R_1$ is H, halogen, $(C_1-C_4)$alkyl, NH—$(C_1-C_4)$alkyl, N[$(C_1-C_4)$alkyl]$_2$ or NH-phenyl. Most preferably, $R_1$ is H, $(C_1-C_2)$alkyl or NH—$(C_1-C_2)$alkyl, especially preferred $R_1$ is H.

$R_3$ is preferably H, halogen, $(C_1-C_4)$alkylene-R', O—R" or NHR". More preferred, $R_3$ is H or NHR". Most preferred, $R_3$ is H, NH—$(C_5-C_6)$heterocyclyl or NH-phenyl, especially preferred are H, NH—$(C_5-C_6)$heteroaryl containing one or more N atoms or NH-phenyl. Most preferred, $R_3$ is H.

Examples of $R_3$ substituents are

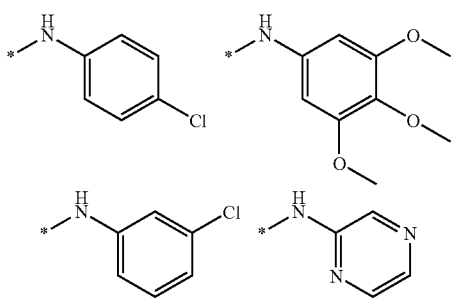

Preferably, $R_4$ is H, halogen or $(C_1-C_6)$alkyl. More preferred, $R_4$ is H, halogen or $(C_1-C_4)$alkyl. Most preferred, $R_4$ is H.

Preferably, $R_5$ is H, halogen, CN, $(C_1-C_6)$alkyl, $(C_2-C_6)$alkenyl, R', NH—$(C_6-C_{10})$aryl or $(C_1-C_6)$alkylene-R'. More preferably, $R_5$ is H, halogen, $(C_1-C_6)$alkyl, $(C_2-C_6)$alkenyl, R', NH—$(C_6-C_{10})$aryl or $(C_1-C_6)$alkylene-R'. Most preferably, $R_5$ is H, halogen, $(C_1-C_6)$alkyl, $(C_2-C_6)$alkenyl, $(C_6-C_{10})$aryl, NH—$(C_6-C_{10})$aryl, $(C_1-C_2)$alkyl-$(C_6-C_{10})$aryl or $(C_5-C_{10})$heteroaryl. Especially preferred, $R_5$ is H, halogen, phenyl, $(C_1-C_6)$alkyl, $(C_2-C_6)$alkenyl, $(C_6-C_{10})$aryl or $(C_5-C_6)$heteroaryl. Most especially preferred $R_5$ is H, halogen, methyl, ethyl, vinyl, phenyl, thienyl or pyridyl.

Examples of $R_5$ are hydrogen, fluoro, chloro, bromo, iodo, methyl, ethyl, vinyl, phenyl, thienyl or pyridyl, nitrile, nitro, (p-methoxy)-phenyl, N-aniline, benzyl, 2-propenyl, s-butenyl, cyclopropyl, tetrazol, amino, 4-methoxy-aniline or N-acetyl, preferably hydrogen, fluoro, chloro, bromo, iodo, methyl, ethyl, vinyl, phenyl, thienyl or pyridyl.

More preferred, $R_5$ is H, halogen, methyl, or ethyl, most preferred $R_5$ is H.

Preferably, $R_6$ and $R_6'$ are independently of each other
H,
$(C_1-C_6)$alkyl,
R',
$(C_1-C_4)$alkylene-$(C_3-C_8)$cycloalkyl,
$(C_1-C_4)$alkylene-$(C_5-C_{10})$heterocyclyl,
$(C_1-C_4)$alkylene-$(C_6-C_{10})$aryl,
$(C_1-C_6)$alkylene-O—$(C_1-C_6)$alkyl,
$(C_1-C_4)$alkylene-C(O)—$(C_5-C_{10})$heterocyclyl,
$(C_1-C_4)$alkylene-C(O)—$(C_6-C_{10})$aryl,
$(C_1-C_6)$alkylene-C(O)N[$(C_1-C_6)$alkyl]$_2$,
$(C_1-C_6)$alkylene-C(O)NH—$(C_1-C_6)$alkyl,
$(C_1-C_6)$alkylene-C(O)O—$(C_1-C_6)$alkyl,
C(O)R'
C(O)$(C_1-C_6)$alkyl,
C(O)O—$(C_1-C_6)$alkyl,
C(O)NH—$(C_1-C_6)$alkyl,
C(O)N[$(C_1-C_6)$alkyl]$_2$, or
C(O)$(C_1-C_6)$alkylene-R', or
$R_6$ and $R_6'$, together with the N-atom to which they are attached, form a $(C_5-C_{10})$heterocyclyl group.

In a further preferred embodiment, $R_6$ and $R_6'$ are independently of each other
H,
$(C_1-C_6)$alkyl,
$(C_5-C_{10})$heterocyclyl,
$(C_3-C_8)$cycloalkyl,
$(C_6-C_{10})$aryl
$(C_1-C_4)$alkylene-$(C_3-C_8)$cycloalkyl,
$(C_1-C_4)$alkylene-$(C_5-C_{10})$heterocyclyl,
$(C_1-C_4)$alkylene-$(C_6-C_{10})$aryl,
$(C_1-C_6)$alkylene-O—$(C_1-C_6)$alkyl,
$(C_1-C_6)$alkylene-C(O)N[$(C_1-C_6)$alkyl]$_2$,
$(C_1-C_6)$alkylene-C(O)NH—$(C_1-C_6)$alkyl,
$(C_1-C_6)$alkylene-C(O)O—$(C_1-C_6)$alkyl,
C(O)O—$(C_1-C_6)$alkyl,
C(O)$(C_1-C_6)$alkyl,
C(O)$(C_3-C_5)$cycloalkyl,
C(O)NH—$(C_1-C_6)$alkyl,
C(O)N[$(C_1-C_6)$alkyl]$_2$,
C(O)$(C_1-C_6)$alkylene-$(C_3-C_8)$cycloalkyl,
C(O)$(C_1-C_6)$alkylene-$(C_5-C_{10})$heterocyclyl,
C(O)$(C_1-C_6)$alkylene-$(C_6-C_{10})$aryl, or
$R_6$ and $R_6'$, together with the N-atom to which they are attached form a $(C_5-C_{10})$heterocyclyl group.

In a more preferred embodiment, $R_6$ is H, $(C_1-C_6)$alkyl, $(C_3-C_6)$cycloalkyl or $(C_1-C_4)$alkylene-$(C_3-C_6)$cycloalkyl, and
$R_6'$ is H,
$(C_1-C_6)$alkyl,
$(C_3-C_5)$cycloalkyl,
$(C_5-C_{10})$heterocyclyl,
$(C_6-C_{10})$aryl, ($C_1$-$C_4$)alkylene-($C_3$-$C_8$)cycloalkyl,
($C_1$-$C_4$)alkylene-($C_5$-$C_{10}$)heterocyclyl,
($C_1$-$C_4$)alkylene-($C_6$-$C_{10}$)aryl,
($C_1$-$C_6$)alkylene-O—($C_1$-$C_6$)alkyl,
($C_1$-$C_6$)alkylene-C(O)NH—($C_1$-$C_6$)alkyl,
($C_1$-$C_6$)alkylene-C(O)N[($C_1$-$C_6$)alkyl]$_2$,
($C_1$-$C_6$)alkylene-C(O)O—($C_1$-$C_6$)alkyl,
C(O)O—($C_1$-$C_6$)alkyl,
C(O)($C_1$-$C_6$)alkyl,
C(O)($C_3$-$C_8$)cycloalkyl,
C(O)NH—($C_1$-$C_6$)alkyl,
C(O)N[($C_1$-$C_6$)alkyl]$_2$,
C(O)($C_1$-$C_6$)alkylene-($C_3$-$C_6$)cycloalkyl,
C(O)($C_1$-$C_6$)alkylene-($C_5$-$C_{10}$)heterocyclyl,
C(O)($C_1$-$C_6$)alkylene-($C_6$-$C_{10}$)aryl, or
$R_6$ and $R_6'$, together with the N-atom to which they are attached, form a ($C_5$-$C_{10}$)heterocyclyl group.

In a further more preferred embodiment, $R_6$ is H, ($C_1$-$C_6$) alkyl and $R_6'$ is H,
($C_1$-$C_6$)alkyl,
($C_3$-$C_8$)cycloalkyl,
($C_6$-$C_{10}$)aryl,
($C_5$-$C_{10}$)heterocyclyl,
($C_1$-$C_4$)alkylene-($C_3$-$C_8$)cycloalkyl,
($C_1$-$C_4$)alkylene-($C_5$-$C_{10}$)heterocyclyl,
($C_1$-$C_6$)alkylene-($C_6$-$C_{10}$)aryl,
($C_1$-$C_4$)alkylene-O—($C_1$-$C_4$)alkyl,
C(O)($C_1$-$C_6$)alkyl,
($C_1$-$C_4$)alkylene-C(O)N[($C_1$-$C_4$)alkyl]$_2$,
($C_1$-$C_6$)alkylene-C(O)NH—($C_1$-$C_6$)alkyl, or
$R_6$ and $R_6'$, together with the N-atom to which they are attached, form a ($C_5$-$C_{10}$)heterocyclyl group.

In a further even more preferred embodiment, $R_6$ is H, ($C_1$-$C_6$)alkyl and $R_6'$ is
H,
($C_1$-$C_6$)alkyl;
($C_3$-$C_5$)cycloalkyl;
($C_1$-$C_4$)alkylene-($C_3$-$C_8$)cycloalkyl;
($C_1$-$C_4$)alkylene-O—($C_1$-$C_4$)alkyl;
C(O)($C_1$-$C_4$)alkyl;
($C_1$-$C_4$)alkylene-C(O)N[($C_1$-$C_4$)alkyl]$_2$;
($C_1$-$C_4$)alkylene-($C_5$-$C_{10}$)heterocyclyl wherein heterocyclyl is unsubstituted or substituted one or more times, preferably one to three times, more preferably one or two times, by a group independently selected from ($C_1$-$C_4$)alkyl, O—($C_1$-$C_4$)alkyl, halogen or phenyl, or is substituted once by ($C_5$-$C_6$)heterocyclyl;
wherein phenyl or ($C_5$-$C_6$)heterocyclyl are unsubstituted or substituted one to three times by halogen, ($C_1$-$C_4$)alkyl or O—($C_1$-$C_4$)alkyl; or
($C_1$-$C_4$)alkylene-($C_6$-$C_{10}$)aryl wherein aryl is unsubstituted or substituted one or more times, preferably one to three times, by a group independently selected from halogen; ($C_1$-$C_4$)alkyl, preferably CH$_3$ or CF$_3$; O—($C_1$-$C_4$)alkyl; CN, SO$_2$—NH$_2$; SO$_2$—($C_1$-$C_4$)alkyl preferably SO$_2$—CH$_3$ or SO$_2$—CF$_3$; SO$_2$—N=CH—N[($C_1$-$C_4$)alkyl]$_2$, preferably SO$_2$—N=N—N(CH$_3$)$_2$; NH—CO—($C_1$-$C_4$)alkyl, preferably NH—CO—CH$_3$; or CO—O—($C_1$-$C_4$) alkyl, or ($C_6$-$C_{10}$)aryl is substituted once by unsubstituted phenyl, unsubstituted O-phenyl or unsubstituted ($C_5$-$C_6$) heterocyclyl;
or $R_6$ and $R_6'$, together with the N-atom to which they are attached, form a ($C_5$-$C_6$)heterocyclyl group, which is unsubstituted or substituted one to three times, preferably once, by ($C_1$-$C_4$)alkyl or C(O)O($C_1$-$C_4$)alkyl;

wherein a ($C_1$-$C_4$)alkyl or ($C_1$-$C_6$)alkyl residue is unsubstituted or substituted one to three times by halogen, preferably by fluoro.

Preferably the formed heterocyclyl group is morpholino, piperidino, pyrrolidino or piperazino. More preferably the heterocyclyl group is morpholino or 4-(ethoxycarbonyl)-piperazinyl.

In a most preferred embodiment, $R_6$ is H, ($C_1$-$C_6$)alkyl and $R_6'$ is H, ($C_1$-$C_6$)alkyl, ($C_3$-$C_8$)cycloalkyl.

In a further most preferred embodiment, $R_6$ is H and $R_6'$ is H, unsubstituted ($C_1$-$C_6$)alkyl, or unsubstituted ($C_3$-$C_8$)cycloalkyl. Especially preferred, $R_6$ and $R_6'$ are H.

As examples for these embodiments, R6 or R6' are, independently from each other, hydrogen, methyl, ethyl, propyl, isopropyl, 3-methyl-butyl, 2-methyl-propyl, butyl, pentyl, 3,3,3-trifluoropropyl, 4,4,4-trifluorobutyl or a substituent selected from the group consisting of

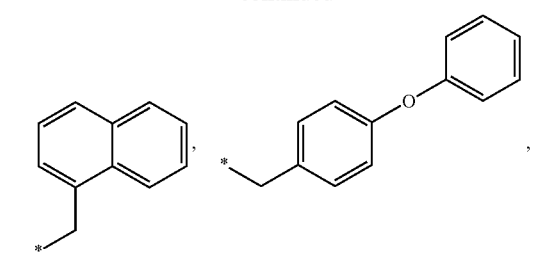
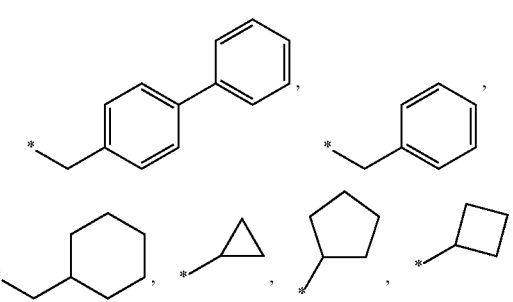
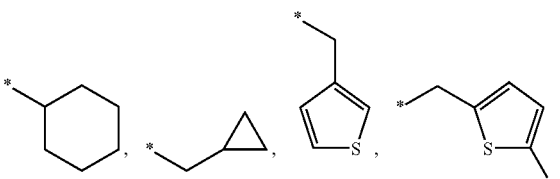
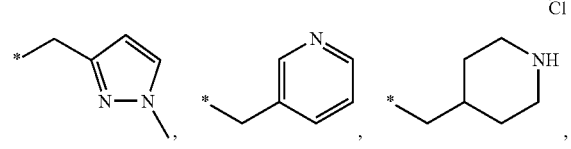
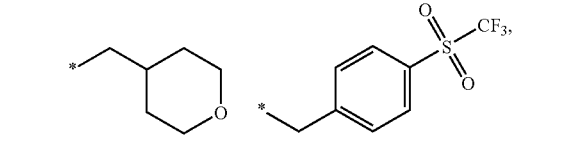
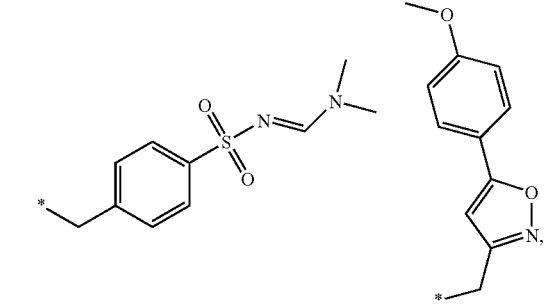
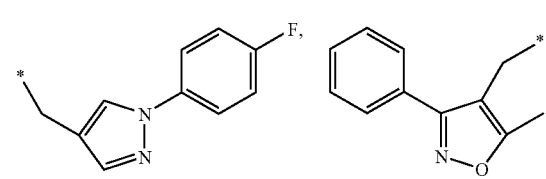
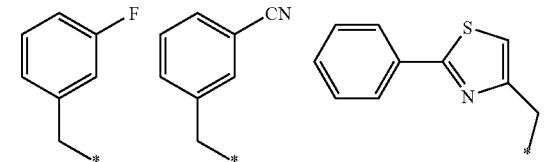
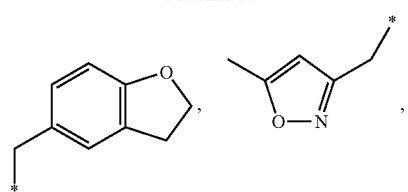
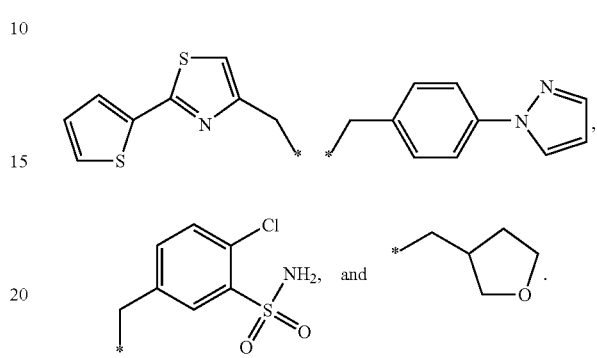
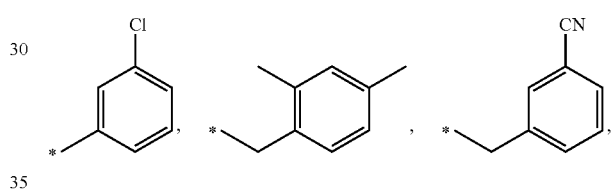
Other examples for these embodiments of $R_6$ or $R_6'$ are, independently from each other,
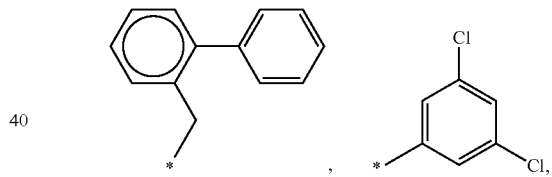
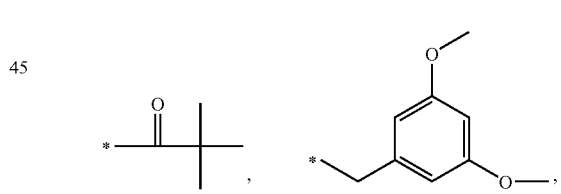
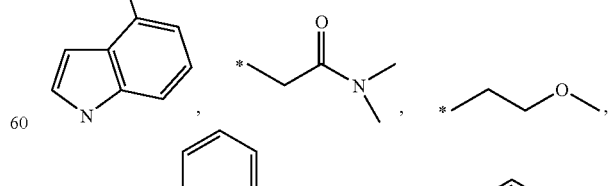
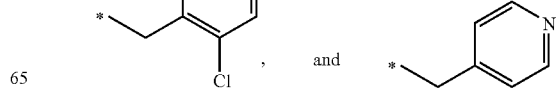

An example for $R_6$, $R_6'$ forming a $(C_5-C_{10})$heterocyclyl is

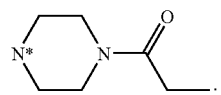

The * denotes where the bond is connected to the N atom of the amine. Preferably, $R_7$ is H, halogen, CN, $(C_1-C_6)$alkyl, O—$(C_1-C_6)$alkyl, $(C_2-C_6)$alkenyl, R' or $(C_1-C_6)$alkylene-$(C_3-C_8)$cycloalkyl. More preferred, $R_7$ is H, halogen, CN, $(C_1-C_4)$alkyl, O—$(C_1-C_4)$alkyl, $(C_2-C_4)$alkenyl, phenyl, cyclopropyl or $(C_5-C_6)$heteroaryl. Most preferably, $R_7$ is H, fluoro, chloro, bromo, methyl, ethyl, methoxy, phenyl, nitrile, cyclopropyl, thienyl or vinyl, most especially preferred $R_7$ is H, fluoro, chloro, methyl or methoxy. More particular preferred $R_7$ is H.

$R_8$ is preferably H, halogen or $(C_1-C_4)$alkyl. More preferred, $R_8$ is H, Cl, F, methyl or ethyl. Most preferred $R_8$ is H.

Preferably, $R_2$ is H, halogen or $(C_1-C_4)$alkyl. Preferably, $R_2$ is H or $(C_1-C_2)$alkyl. More preferred, $R_2$ is H, methyl or ethyl. Most preferred $R_2$ is H. $R_2$ may be bound to any carbon atom of the ring including the position where the linker group L is bound.

Preferably, n is 1, 2 or 3. More preferred, n is 1 or 2. Most preferred n is 1.

Preferably m is 2, 3 or 4. More preferred m is 3.

The linker group L may be bound to the ring in any position via a ring carbon atom. In a preferred embodiment, m is 3 and L is attached to the 4-position of the amino cyclohexane ring

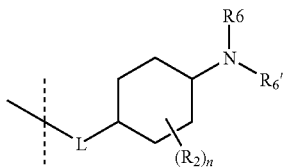

or L is attached to the 3-position of the amino cyclohexane ring

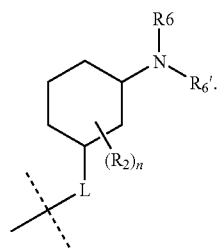

In an especially preferred embodiment, L is attached to the 4-position of the amino cyclohexane ring.

In a further preferred embodiment, L is O-methylene, O-ethylene or preferably O. More preferably, m is 3 and L is O-methylene, O-ethylene or O attached to the 4-position of the amino cyclohexane ring.

In residues $R_1$ to $R_8$ an alkyl or alkylene can optionally be substituted one or more times by halogen. Preferably alkyl or alkylene is substituted one to three times by halogen selected from chloro or bromo but may be substituted by fluoro once or more, e.g. being perfluorinated. Preferably halogen is fluor. More preferred an alkyl or alkylene is not halogenated.

In residues $R_4$, $R_5$, $R_6$, $R_6'$, $R_7$ and $R_8$ alkyl, alkylene or cycloalkyl can optionally be substituted one or more times by a group selected independently from OH, $OCH_3$, COOH, $COOCH_3$, $NH_2$, $NHCH_3$, $N(CH_3)_2$, $CONH_2$, $CONHCH_3$ or $CON(CH_3)_2$.

If substituted, the number of substituents is preferably between 1, 2, 3 or 4, more preferably 1 or 2 with 1 being even more preferred. Preferably $R_4$, $R_5$, $R_7$ and $R_8$ are not substituted. Preferably an alkylene or cycloalkyl is not substituted. More preferably an alkyl, alkylene or cycloalkyl is not substituted.

In preferred embodiments of the present invention one or more or all of the groups contained in the compounds of formula (I) can independently of each other have any of the preferred, more preferred or most preferred definitions of the groups specified above or any one or some of the specific denotations which are comprised by the definitions of the groups and specified above, all combinations of preferred definitions, more preferred or most preferred and/or specific denotations being a subject of the present invention. Also with respect to all preferred embodiments the invention includes the compounds of the formula (I) in all stereoisomeric forms and mixtures of stereoisomeric forms in all ratios, and their pharmaceutically acceptable salts.

The term "*-" in the exemplified substituents vide supra marks the point where the substituent is attached, which means, for example, for a $R_3$ substituent

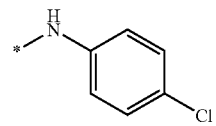 [SMILES: *Nc1ccc(Cl)cc1]

and m is 3 a compound of the formula

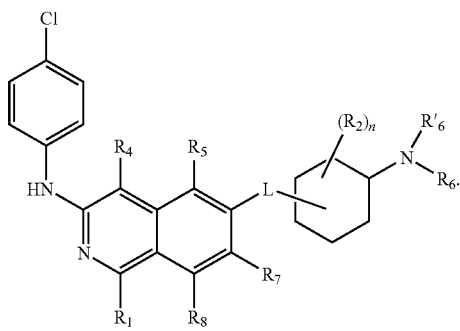

A preferred embodiment is a compound of the formula (I) wherein
$R_1$ is H, $(C_1-C_6)$alkyl, $(C_6-C_{10})$aryl, NH—$(C_1-C_6)$alkyl, NH—$(C_6-C_{10})$aryl, or $N[(C_1-C_6)$alkyl$]_2$;
$R_2$ is hydrogen, halogen, or $(C_1-C_6)$alkyl;
$R_3$ is H, halogen, $(C_1-C_4)$alkylene-R', O—R" or NHR";
$R_4$ is H, halogen or $(C_1-C_6)$alkyl;
$R_5$ is H, $(C_1-C_6)$alkyl, halogen, CN, $(C_2-C_6)$alkenyl, $(C_6-C_{10})$aryl, NH—$(C_6-C_{10})$aryl, $(C_1-C_6)$alkylene-$(C_6-C_{10})$aryl, $(C_5-C_{10})$heterocyclyl or $(C_1-C_6)$alkylene-$(C_5-C_{10})$heterocyclyl;
$R_6$ and $R_6'$ are independently of each other H, R', $(C_1-C_8)$alkyl, $(C_1-C_6)$alkylene-R', $(C_1-C_6)$alkylene-O—$(C_1-C_6)$alkyl, $(C_1-C_6)$alkylene-O—R', $(C_1-C_6)$alkylene-CH[R']$_2$, $(C_1-C_6)$alkylene-C(O)$NH_2$, $(C_1-C_6)$alkylene-C(O)NH—

R', $(C_1-C_6)$alkylene-C(O)N$[(C_1-C_4)$alkyl$]_2$, $(C_1-C_6)$alkylene-C(O)N[R']$_2$, C(O)O—$(C_1-C_6)$alkyl, C(O)$(C_1-C_6)$alkyl, C(O)$(C_3-C_8)$cycloalkyl, C(O)$(C_5-C_{10})$heterocyclyl, C(O)NH—$(C_1-C_6)$alkyl, C(O)N$[(C_1-C_6)$alkyl$]_2$, C(O)—$(C_1-C_6)$alkylene-$(C_3-C_8)$cycloalkyl, C(O)$(C_1-C_6)$alkylene-$(C_5-C_{10})$heterocyclyl, C(O)$(C_1-C_6)$alkylene-$(C_6-C_{10})$aryl, or $R_6$ and $R_6$', together with the N-atom to which they are attached, form a $(C_5-C_6)$heterocyclyl group.

$R_7$ is H, halogen, CN, $(C_1-C_6)$alkyl, O—$(C_1-C_6)$alkyl, $(C_2-C_6)$alkenyl or R';

$R_8$ is H, halogen or $(C_1-C_6)$alkyl;

m is 2, 3 or 4 n is 1, 2 or 3, and

L is O,O-methylene or O-ethylene;

and their pharmaceutically acceptable salts.

A further preferred embodiment is a compound of the formula (I) wherein $R_1$ is H, $(C_1-C_6)$alkyl, $(C_6-C_{10})$aryl, NH—$(C_1-C_6)$alkyl, NH—$(C_6-C_{10})$aryl, or N$[(C_1-C_6)$alkyl$]_2$;

$R_2$ is H or $(C_1-C_4)$alkyl;

$R_3$ is H, halogen or NHR", wherein R" is defined as above;

$R_4$ is H, halogen or $(C_1-C_4)$alkyl;

$R_5$ is H, $(C_1-C_6)$alkyl, halogen, $(C_2-C_4)$alkenyl, $(C_6-C_{10})$aryl, $(C_1-C_6)$alkylene-$(C_6-C_{10})$aryl or $(C_5-C_{10})$heterocyclyl;

$R_6$ and $R_6$' are independently of each other H, $(C_3-C_8)$cycloalkyl, $(C_1-C_8)$alkyl, $(C_1-C_6)$alkylene-O—$(C_1-C_6)$alkyl, $(C_1-C_3)$alkylene-R'; C(O)$(C_1-C_6)$alkyl, C(O)$(C_3-C_8)$cycloalkyl, C(O)$(C_5-C_{10})$heterocyclyl, C(O)$(C_1-C_6)$alkylene-$(C_3-C_8)$cycloalkyl, C(O)$(C_1-C_6)$alkylene-$(C_5-C_{10})$heterocyclyl or C(O)$(C_1-C_6)$alkylene-$(C_6-C_{10})$aryl;

$R_7$ is H, halogen, CN, $(C_1-C_6)$alkyl, O—$(C_1-C_6)$alkyl, $(C_2-C_6)$alkenyl or R';

$R_8$ is H, halogen or $(C_1-C_6)$alkyl;

m is 2, 3 or 4 n is 1, 2 or 3; and

L is O;

and their pharmaceutically acceptable salts.

An especially preferred embodiment is a compound of the formula (I) wherein $R_1$ is H, $(C_1-C_4)$alkyl, NH—$(C_1-C_4)$alkyl, N$[(C_1-C_4)$alkyl$]_2$ or NH-phenyl;

$R_2$ is H, $(C_1-C_4)$alkyl;

$R_3$ is H, NH—$(C_5-C_6)$heteroaryl or NH-phenyl;

$R_4$ is H, halogen or $(C_1-C_4)$alkyl;

$R_5$ is H, $(C_1-C_4)$alkyl, halogen, $(C_2-C_4)$alkenyl, $(C_6-C_{10})$aryl, $(C_1-C_2)$alkyl-$(C_6-C_{10})$aryl or $(C_5-C_6)$heteroaryl;

$R_6$ is H, $(C_3-C_6)$cycloalkyl or $(C_1-C_4)$alkyl;

$R_6$' is H, $(C_3-C_8)$cycloalkyl, $(C_1-C_8)$alkyl, $(C_1-C_3)$alkylene-R', C(O)O—$(C_1-C_6)$alkyl, C(O)$(C_1-C_6)$alkyl, C(O)$(C_3-C_6)$cycloalkyl, C(O)$(C_5-C_6)$heterocyclyl, C(O)$(C_1-C_3)$alkylene-$(C_3-C_6)$cycloalkyl, C(O)$(C_1-C_3)$alkylene-$(C_5-C_6)$heterocyclyl, or C(O)$(C_1-C_3)$alkylene-phenyl;

$R_7$ is H, halogen, CN, $(C_1-C_4)$alkyl, O—$(C_1-C_4)$alkyl, $(C_2-C_4)$alkenyl, phenyl, cyclopropyl, $(C_5-C_6)$heteroaryl;

$R_8$ is H, halogen or $(C_1-C_4)$alkyl;

m is 3 n is 1; and

L is O;

and their pharmaceutically acceptable salts.

In an embodiment the present invention relates to a compound of formula (I) independently selected from the group of 10 trans-[4-(7-Chloro-isoquinolin-6-yloxy)-cyclohexyl]-carbamic acid tert-butyl ester, 11 trans-4-(7-Chloro-isoquinolin-6-yloxy)-cyclohexylamine, 12 [cis-4-(5-Chloro-isoquinolin-6-yloxy)-cyclohexyl]-carbamic acid tert-butyl ester, 13 cis-4-(5-Chloro-isoquinolin-6-yloxy)-cyclohexylamine, 14 cis-4-(4-Chloro-isoquinolin-6-yloxy)-cyclohexylamine, 15 cis-4-(7-Methoxy-isoquinolin-6-yloxy)-cyclohexylamine, 16 cis-4-(Isoquinolin-6-yloxy)-cyclohexylamine, 17 trans-4-(Isoquinolin-6-yloxy)-cyclohexylamine, 18 trans-4-(5-Bromo-isoquinolin-6-yloxy)-cyclohexylamine, 19 cis-4-(5-Bromo-isoquinolin-6-yloxy)-cyclohexylamine, 20 (3-Fluoro-benzyl)-[cis-4-(isoquinolin-6-yloxy)-cyclohexyl]-amine, 21 [cis-4-(Isoquinolin-6-yloxy)-cyclohexyl]-propyl-amine, 22 [cis-4-(Isoquinolin-6-yloxy)-cyclohexyl]-(3,3,3-trifluoro-propyl)-amine, 23 [cis-4-(Isoquinolin-6-yloxy)-cyclohexyl]-pyridin-3-ylmethyl-amine, 24 Cyclopropyl-methyl-cis-[4-(isoquinolin-6-yloxy)-cyclohexyl]-amine, 25 Isobutyl-cis-[4-(isoquinolin-6-yloxy)-cyclohexyl]-amine, 26 Isopropyl-cis-[4-(isoquinolin-6-yloxy)-cyclohexyl]-amine, 28 Cyclopropyl-[4-(isoquinolin-6-yloxy)-cyclohexyl]-amine, 29 [4-(Isoquinolin-6-yloxy)-cyclohexyl]-dimethyl-amine, 30 Ethyl-[4-(isoquinolin-6-yloxy)-cyclohexyl]-pyridin-4-ylmethyl-amine, 31 Benzyl-[4-(isoquinolin-6-yloxy)-cyclohexyl]-methyl-amine, 32 [4-(Isoquinolin-6-yloxy)-cyclohexyl]-(4-phenoxy-benzyl)-amine, 33 [4-(Isoquinolin-6-yloxy)-cyclohexyl]-[5-(4-methoxy-phenyl)-isoxazol-3-ylmethyl]-amine, 34 N-(4-{[4-(Isoquinolin-6-yloxy)-cyclohexylamino]-methyl}-phenyl)-acetamide, 35 [4-(Isoquinolin-6-yloxy)-cyclohexyl]-(4-methoxy-benzyl)-amine, 36 (4-Chloro-benzyl)-[4-(isoquinolin-6-yloxy)-cyclohexyl]-amine, 37 (2,3-Dimethoxy-benzyl)-[4-(isoquinolin-6-yloxy)-cyclohexyl]-amine, 38 5-(4-{[4-(Isoquinolin-6-yloxy)-cyclohexylamino]-methyl}-phenyl)-5-methyl-imidazolidine-2,4-dione, 39 (3,5-Dimethoxy-benzyl)-[4-(isoquinolin-6-yloxy)-cyclohexyl]amine, 40 3-{[4-(Isoquinolin-6-yloxy)-cyclohexylamino]-methyl}-benzonitrile, 41 [4-(Isoquinolin-6-yloxy)-cyclohexyl]-(4-methanesulfonyl-benzyl)-amine, 42 [2-(1H-Indol-3-yl)-ethyl]-[4-(isoquinolin-6-yloxy)-cyclohexyl]methyl-amine, 43 2-{[4-(Isoquinolin-6-yloxy)-cyclohexyl]-methylamino}-N,N-dimethyl-acetamide, 44 4-[4-(Isoquinolin-6-yloxy)-cyclohexyl]piperazine-1-carboxylic acid ethyl ester, 45 Isobutyl-[4-(isoquinolin-6-yloxy)-cyclohexyl]methyl-amine, 46 [4-(Isoquinolin-6-yloxy)-cyclohexyl]-methyl-pyridin-4-ylmethyl-amine, 47 Ethyl-[4-(isoquinolin-6-yloxy)-cyclohexyl]-(2-methoxy-ethyl)-amine, 48 4-{[4-(Isoquinolin-6-yloxy)-cyclohexylamino]-methyl}-benzonitrile, 49 6-(4-Morpholin-4-yl-cyclohexyloxy)-isoquinoline, 50 4-{[4-(Isoquinolin-6-yloxy)-cyclohexylamino]-methyl}-benzoic acid methyl ester,
51 (4-tert-Butyl-benzyl)-[4-(isoquinolin-6-yloxy)-cyclohexyl]-amine,
52 [1-(4-Fluoro-phenyl)-1H-pyrazol-4-ylmethyl]-[4-(isoquinolin-6-yloxy)-cyclohexyl]-methyl-amine,
53 [4-(Isoquinolin-6-yloxy)-cyclohexyl]-(5-methyl-3-phenyl-isoxazol-4-ylmethyl)-amine,
54 [4-(Isoquinolin-6-yloxy)-cyclohexyl]-naphthalen-1-ylmethyl-amine,
55 [4-(Isoquinolin-6-yloxy)-cyclohexyl]-(2-phenyl-oxazol-4-ylmethyl)-amine,
56 (2,3-Dihydro-benzofuran-5-ylmethyl)-[4-(isoquinolin-6-yloxy)-cyclohexyl]-amine,
57 [4-(Isoquinolin-6-yloxy)-cyclohexyl]-(5-methyl-isoxazol-3-ylmethyl)-amine,
58 [4-(Isoquinolin-6-yloxy)-cyclohexyl]-(2-thiophen-2-yl-thiazol-4-ylmethyl)-amine,
59 (3,5-Dimethyl-benzyl)-[4-(isoquinolin-6-yloxy)-cyclohexyl]-amine,
60 Biphenyl-2-ylmethyl-[4-(isoquinolin-6-yloxy)-cyclohexyl]-amine,
61 [4-(Isoquinolin-6-yloxy)-cyclohexyl]-(4-pyrazol-1-yl-benzyl)-amine,
62 [4-(Isoquinolin-6-yloxy)-cyclohexyl]-(4-methoxy-phenyl)-amine,
63 Cyclopropyl-[trans-4-(isoquinolin-6-yloxy)-cyclohexyl]-amine,
64 Cyclopropyl-[cis-4-(isoquinolin-6-yloxy)-cyclohexyl]-amine,
65 [trans-4-(Isoquinolin-6-yloxy)-cyclohexyl]-(4-phenoxy-benzyl)-amine,
66 [cis-4-(Isoquinolin-6-yloxy)-cyclohexyl]-(4-phenoxy-benzyl)-amine,
67 Benzyl-[trans-4-(isoquinolin-6-yloxy)-cyclohexyl]-methyl-amine,
68 Benzyl-[cis-4-(isoquinolin-6-yloxy)-cyclohexyl]-methyl-amine,
69 [trans-4-(Isoquinolin-6-yloxy)-cyclohexyl]-dimethyl-amine,
70 [cis-4-(Isoquinolin-6-yloxy)-cyclohexyl]-dimethyl-amine,
71 N-(4-{[trans-4-(Isoquinolin-6-yloxy)-cyclohexylamino]-methyl}-phenyl)-acetamide,
72 N-(4-{[cis-4-(Isoquinolin-6-yloxy)-cyclohexylamino]-methyl}-phenyl)-acetamide,
74 2-Chloro-5-{cis-[4-(5-chloro-isoquinolin-6-yloxy)-cyclohexylamino]-methyl}-N-dimethylaminomethylene-benzenesulfonamide,
75 2-Chloro-5-{[4-(5-chloro-isoquinolin-6-yloxy)-cyclohexylamino]-methyl}-benzenesulfonamide,
76 Cyclopropylmethyl-[trans-4-(isoquinolin-6-yloxy)-cyclohexyl]-amine,
77 Bis-cyclopropylmethyl-[trans-4-(isoquinolin-6-yloxy)-cyclohexyl]-amine,
80 [4-(5-Chloro-isoquinolin-6-yloxy)-cyclohexyl]-cyclohexyl-amine,
81 [4-(5-Chloro-isoquinolin-6-yloxy)-cyclohexyl]-cyclopropyl-amine,
82 [4-(5-Chloro-isoquinolin-6-yloxy)-cyclohexyl]-cyclobutyl-amine,
83 [4-(5-Chloro-isoquinolin-6-yloxy)-cyclohexyl]-cyclopentyl-amine,
84 [4-(5-Chloro-isoquinolin-6-yloxy)-cyclohexyl]-isopropyl-amine,
85 [cis-4-(5-Bromo-isoquinolin-6-yloxy)-cyclohexyl]-carbamic acid tert-butyl ester,
86 cis-4-(5-Ethyl-isoquinolin-6-yloxy)-cyclohexylamine,
87 cis-4-(5-Thiophen-3-yl-isoquinolin-6-yloxy)-cyclohexylamine,
88 cis-4-(5-Methyl-isoquinolin-6-yloxy)-cyclohexylamine,
89 cis-4-(5-Pyridin-3-yl-isoquinolin-6-yloxy)-cyclohexylamine,
90 cis-4-(5-Vinyl-isoquinolin-6-yloxy)-cyclohexylamine,
91 cis-4-(5-Thiophen-2-yl-isoquinolin-6-yloxy)-cyclohexylamine,
92 cis-4-(5-Phenyl-isoquinolin-6-yloxy)-cyclohexylamine,
93 cis-4-(5-Pyridin-2-yl-isoquinolin-6-yloxy)-cyclohexylamine,
94 cis-4-(5-Pyridin-4-yl-isoquinolin-6-yloxy)-cyclohexylamine,
96 trans-4-(5,7-Dichloro-isoquinolin-6-yloxy)-cyclohexylamine,
97 [cis-4-(7-Chloro-isoquinolin-6-yloxy)-cyclohexyl]-carbamic acid tert-butyl ester,
98 cis-4-(7-Chloro-isoquinolin-6-yloxy)-cyclohexylamine,
102 cis-4-(5,7-Difluoro-isoquinolin-6-yloxy)-cyclohexylamine,
103 [cis-4-(7-Chloro-isoquinolin-6-yloxy)-cyclohexyl]-propyl-amine,
104 Butyl-[cis-4-(7-chloro-isoquinolin-6-yloxy)-cyclohexyl]-amine,
105 [cis-4-(7-Chloro-isoquinolin-6-yloxy)-cyclohexyl]-isopropyl-amine,
106 [cis-4-(7-Chloro-isoquinolin-6-yloxy)-cyclohexyl]-(1-ethyl-propyl)-amine,
107 [cis-4-(7-Chloro-isoquinolin-6-yloxy)-cyclohexyl]-isobutyl-amine,
108 [cis-4-(7-Chloro-isoquinolin-6-yloxy)-cyclohexyl]-cyclopropylmethyl-amine,
109 [cis-4-(7-Chloro-isoquinolin-6-yloxy)-cyclohexyl]-(3-methyl-butyl)-amine,
110 [cis-4-(7-Chloro-isoquinolin-6-yloxy)-cyclohexyl]-cyclohexylmethyl-amine,
111 [cis-4-(7-Chloro-isoquinolin-6-yloxy)-cyclohexyl]-cyclohexyl-amine,
112 (4-Chloro-benzyl)-[cis-4-(7-chloro-isoquinolin-6-yloxy)-cyclohexyl]-amine,
113 (3-Chloro-benzyl)-[cis-4-(7-chloro-isoquinolin-6-yloxy)-cyclohexyl]-amine,
114 [cis-4-(7-Chloro-isoquinolin-6-yloxy)-cyclohexyl]-(2,4-dichloro-benzyl)-amine,
115 [cis-4-(7-Chloro-isoquinolin-6-yloxy)-cyclohexyl]-4-(4-trifluoromethyl-benzyl)-amine,
116 [cis-4-(7-Chloro-isoquinolin-6-yloxy)-cyclohexyl]-pyridin-4-ylmethyl-amine,
117 [cis-4-(7-Chloro-isoquinolin-6-yloxy)-cyclohexyl]-ethyl-amine,
118 [trans-4-(7-Chloro-isoquinolin-6-yloxy)-cyclohexyl]-propyl-amine,
119 Butyl-[trans-4-(7-chloro-isoquinolin-6-yloxy)-cyclohexyl]-amine,
120 [trans-4-(7-Chloro-isoquinolin-6-yloxy)-cyclohexyl]-isopropyl-amine,
121 [trans-4-(7-Chloro-isoquinolin-6-yloxy)-cyclohexyl]-(3-methyl-butyl)-amine,
122 [trans-4-(7-Chloro-isoquinolin-6-yloxy)-cyclohexyl]-cyclohexylmethyl-amine,
123 Benzyl-[trans-4-(7-chloro-isoquinolin-6-yloxy)-cyclohexyl]-amine,
124 [trans-4-(7-Chloro-isoquinolin-6-yloxy)-cyclohexyl]-(4-methyl-benzyl)-amine,
125 [trans-4-(7-Chloro-isoquinolin-6-yloxy)-cyclohexyl]-pyridin-3-ylmethyl-amine, 126 [trans-4-(7-Chloro-isoquinolin-6-yloxy)-cyclohexyl]-(4-methanesulfonyl-benzyl)-amine,
127 [trans-4-(7-Chloro-isoquinolin-6-yloxy)-cyclohexyl]-naphthalen-1-ylmethyl-amine,
128 [trans-4-(7-Chloro-isoquinolin-6-yloxy)-cyclohexyl]-(tetrahydro-furan-3-ylmethyl)-amine,
129 [trans-4-(7-Chloro-isoquinolin-6-yloxy)-cyclohexyl]-cyclohexyl-amine,
130 [trans-4-(7-Chloro-isoquinolin-6-yloxy)-cyclohexyl]-cyclopropylmethyl-amine,
131 [trans-4-(7-Chloro-isoquinolin-6-yloxy)-cyclohexyl]-isobutyl-amine,
132 (4-Chloro-benzyl)-[trans-4-(7-chloro-isoquinolin-6-yloxy)-cyclohexyl]-amine,
133 (3-Chloro-benzyl)-[trans-4-(7-chloro-isoquinolin-6-yloxy)-cyclohexyl]-amine,
134 [trans-4-(7-Chloro-isoquinolin-6-yloxy)-cyclohexyl]-(2,4-dichloro-benzyl)-amine,
135 [trans-4-(7-Chloro-isoquinolin-6-yloxy)-cyclohexyl]-(3,5-dichloro-benzyl)-amine,
136 (2-Chloro-benzyl)-[trans-4-(7-chloro-isoquinolin-6-yloxy)-cyclohexyl]-amine,
137 3-{[trans-4-(7-Chloro-isoquinolin-6-yloxy)-cyclohexylamino]-methyl}-N-[1-dimethylamino-meth-(E)-ylidene]-4-methoxy-benzenesulfonamide,
138 [trans-4-(7-Chloro-isoquinolin-6-yloxy)-cyclohexyl]-4-(4-trifluoromethanesulfonyl-benzyl)-amine,
139 [trans-4-(7-Chloro-isoquinolin-6-yloxy)-cyclohexyl]-4-(4-trifluoromethyl-benzyl)-amine,
145 [6-(cis-4-Amino-cyclohexyloxy)-isoquinolin-3-yl]-(3-methoxy-phenyl)-amine,
146 [6-(cis-4-Amino-cyclohexyloxy)-isoquinolin-3-yl]-(4-methoxy-phenyl)-amine,
147 [6-(cis-4-Amino-cyclohexyloxy)-isoquinolin-3-yl]-(3-chloro-phenyl)-amine,
148 [6-(cis-4-Amino-cyclohexyloxy)-isoquinolin-3-yl]-(4-chloro-phenyl)-amine,
149 [6-(cis-4-Amino-cyclohexyloxy)-isoquinolin-3-yl]-(3,4,5-trimethoxy-phenyl)-amine,
150 [6-(cis-4-Amino-cyclohexyloxy)-isoquinolin-3-yl]-pyrazin-2-yl-amine, and
156 cis-4-(4-Ethyl-isoquinolin-6-yloxy)-cyclohexylamine, or pharmaceutically acceptable salt thereof.

As in any embodiment of the invention, in the preceding embodiments which contain preferred, more preferred, most preferred or exemplary definitions of compounds according to the invention, one or more or all of the groups can have any of its preferred, more preferred, most preferred definitions specified above or any one or some of the specific denotations which are comprised by its definitions and are specified above.

Isoquinoline substitution pattern is numbered according to IUPAC rules:

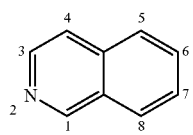

All references to "compound(s) of formula (I)" hereinafter refer to compound(s) of the formula (I) as described above, and their pharmaceutically acceptable salts, and/or to their stereoisomeric forms, polymorphs and solvates. Physiologically functional derivatives as described herein are also included.

Pharmaceutically acceptable salts of compounds of the formula (I) mean both their organic and inorganic salts as described in Remington's Pharmaceutical Sciences (17th edition, page 1418 (1985)). Because of the physical and chemical stability and the solubility, preference is given for acidic groups inter alia to sodium, potassium, calcium and ammonium salts; preference is given for basic groups inter alia to salts of maleic acid, fumaric acid, succinic acid, malic acid, tartaric acid, methylsulfonic acid, hydrochloric acid, sulfuric acid, phosphoric acid or of carboxylic acids or sulfonic acids, for example as hydrochlorides, hydrobromides, phosphates, sulfates, methanesulfonates, acetates, lactates, maleates, fumarates, malates, gluconates, and salts of amino acids, of natural bases or carboxylic acids. The preparation of pharmaceutically acceptable salts from compounds of the formula (I) which are capable of salt formation, including their stereoisomeric forms, takes place in a manner known per se. The compounds of the formula (I) form stable alkali metal, alkaline earth metal or optionally substituted ammonium salts with basic reagents such as hydroxides, carbonates, bicarbonates, alcoholates and ammonia or organic bases, for example trimethyl- or triethylamine, ethanolamine, diethanolamine or triethanolamine, trometamol or else basic amino acids, for example lysine, ornithine or arginine. Where the compounds of the formula (I) have basic groups, stable acid addition salts can also be prepared with strong acids. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula (I) of the invention, for example an N-oxide, which on administration to a mammal such as, for example, a human is able to form (directly or indirectly) a compound of the formula (I) or an active metabolite thereof.

Physiologically functional derivatives include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not.

The invention relates to compounds of the formula (I) in the form of their stereoisomeric forms, which include racemates, racemic mixtures, pure enantiomers and diastereomers and mixtures thereof.

The compounds of the invention may also exist in various polymorphous forms, for example as amorphous and crystalline polymorphous forms. All polymorphous forms of the compounds of the invention belong within the framework of the invention and are a further aspect of the invention.

If radicals or substituents may occur more than once in the compounds of the formula (I), they may all, independently of one another, have the stated meaning and be identical or different.

The present invention therefore also relates to the compounds of the formula (I) and/or their pharmaceutically acceptable salts and/or their prodrugs for use as pharmaceuticals (or medicaments), to the use of the compounds of the formula (I) and/or their pharmaceutically acceptable salts and/or their prodrugs for the production of pharmaceuticals for the treatment and/or prevention of diseases associated with Rho-kinase and/or Rho-kinase mediated phosphorylation of myosin light chain phosphatase, i.e. for the treatment and/or prevention of hypertension, pulmonary hypertension, ocular hypertension, retinopathy, and glaucoma, peripheral circulatory disorder, peripheral arterial occlusive disease (PAOD), coronary heart disease, angina pectoris, heart hypertrophy, heart failure, ischemic diseases, ischemic organ failure (end organ damage), fibroid lung, fibroid liver, liver failure, nephropathy, including hypertension-induced, non-hypertension-induced, and diabetic nephropathies, renal failure, fibroid kidney, renal glomerulosclerosis, organ hypertrophy, asthma, chronic obstructive pulmonary disease (COPD), adult respiratory distress syndrome, thrombotic disorders, stroke, cerebral vasospasm, cerebral ischemia, pain, e.g. neuropathic pain, neuronal degeneration, spinal cord injury, Alzheimer's disease, premature birth, erectile dysfunction, endocrine dysfunctions, arteriosclerosis, prostatic hypertrophy, diabetes and complications of diabetes, metabolic syndrome, blood vessel restenosis, atherosclerosis, inflammation, autoimmune diseases, AIDS, osteopathy such as osteoporosis, infection of digestive tracts with bacteria, sepsis, cancer development and progression, e.g. cancers of the breast, colon, prostate, ovaries, brain and lung and their metastases.

The present invention furthermore relates to pharmaceutical preparations (or pharmaceutical compositions) which contain an effective amount of at least one compound of the formula (I) and/or its pharmaceutically acceptable salts and a pharmaceutically acceptable carrier, i.e. one or more pharmaceutically acceptable carrier substances (or vehicles) and/or additives (or excipients). The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carrier substances and/or additives being used in addition to the compound(s) of the formula (I) and/or its (their) pharmaceutically acceptable salts and/or its (their) prodrugs. For the production of pills, tablets, coated tablets and hard gelatin capsules it is possible to use, for example, lactose, corn starch or derivatives thereof, talc, stearic acid or its salts, etc. Carrier substances for soft gelatin capsules and suppositories are, for example, fats, waxes, semisolid and liquid polyols, natural or hardened oils, etc. Suitable carrier substances for the production of solutions, for example injection solutions, or of emulsions or syrups are, for example, water, saline, alcohols, glycerol, polyols, sucrose, invert sugar, glucose, vegetable oils, etc. Suitable carrier substances for microcapsules, implants or rods are, for example, copolymers of glycolic acid and lactic acid. The pharmaceutical preparations normally contain about 0.5 to about 90% by weight of the compounds of the formula (I) and/or their pharmaceutically acceptable salts and/or their prodrugs. The amount of the active ingredient of the formula (I) and/or its pharmaceutically acceptable salts and/or its prodrugs in the pharmaceutical preparations normally is from about 0.5 to about 1000 mg, preferably from about 1 to about 500 mg.

In addition to the active ingredients of the formula (I) and/or their pharmaceutically acceptable salts and to carrier substances, the pharmaceutical preparations can contain one or more additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula (I) and/or their pharmaceutically acceptable salts. In case a pharmaceutical preparation contains two or more compounds of the formula (I) the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formula (I) allows a great deal of control over the biological and physico-chemical properties of the compounds and thus allows the selection of such desired compounds. Furthermore, in addition to at least one compound of the formula (I) and/or its pharmaceutically acceptable salts, the pharmaceutical preparations can also contain one or more other therapeutically or prophylactically active ingredients.

When using the compounds of the formula (I) the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from about 0.01 to about 100 mg/kg, preferably from about 0.1 to about 50 mg/kg, in particular from about 0.1 to about 10 mg/kg, (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

Furthermore, the compounds of the formula (I) can be used as synthesis intermediates for the preparation of other compounds, in particular of other pharmaceutical active ingredients, which are obtainable from the compounds of the formula I, for example by introduction of substituents or modification of functional groups.

In general, protective groups that may still be present in the products obtained in the coupling reaction are then removed by standard procedures. For example, tert-butyl protecting groups, in particular a tert-butoxycarbonyl group which is a protection form of an amino group, can be deprotected, i.e. converted into the amino group, by treatment with trifluoroacetic acid. As already explained, after the coupling reaction also functional groups can be generated from suitable precursor groups. In addition, a conversion into a pharmaceutically acceptable salt or a prodrug of a compound of the formulae (I) can then be carried out by known processes.

In general, a reaction mixture containing a final compound of the formula (I) or (I') or an intermediate is worked up and, if desired, the product is then purified by customary processes known to those skilled in the art. For example, a synthesized compound can be purified using well known methods such as crystallization, chromatography or reverse phase-high performance liquid chromatography (RP-HPLC) or other methods of separation based, for example, on the size, charge or hydrophobicity of the compound. Similarly, well known methods such as amino acid sequence analysis, NMR, IR and mass spectrometry (MS) can be used for characterizing a compound of the invention.

Isoquinolines can by synthesized via a variety of methods. The following general schemes illustrate some of the possible ways to access isoquinolines, but do not limit the present invention.

Scheme 1:

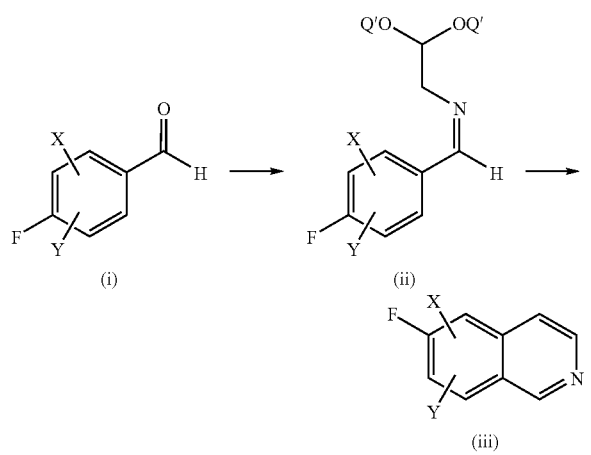

A suitably substituted aldehyde, for example substituted by X or Y being independently from each other hydrogen, alkyl, alkoxy or halide attached in a suitable position, can be reacted with a suitable compound such as for example an acetal of aminoacetaldehyde for example in a solvent like THF, chloroform or toluene under acid catalysis by toluene sulfonic acid or another appropriate acid to give imine (ii) wherein Q' can be for instance methyl or ethyl, which in turn can be cyclized by different methods to the isoquinoline (iii). For example this can be done by Lewis acid catalysis by suitable Lewis acids like titanium tetrachloride, ferrous halides, aluminium halides etc. at temperatures ranging from ambient to 100° C. or by reducing the imine to the corresponding amine by action of a suitable reducing agent like sodium borohydride, converting the amine into an amide or sulphonamide by reaction with a suitable acid chloride and subsequent cyclization to the isoquinoline by action of an appropriate lewis acid.

Scheme 2:

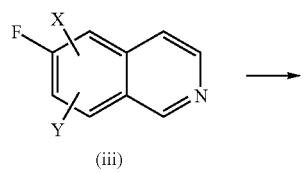

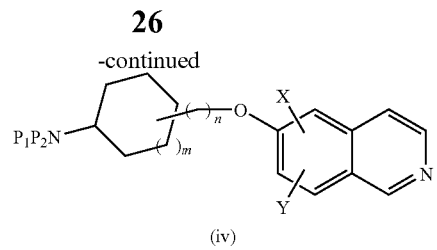

The above obtained 6-fluoro-isoquinolines (iii) can be reacted with suitable $P_1/P_2$ substituted amino alcohols wherein $P_1/P_2$ are independently from each other for example hydrogen, alkyl or a protecting group like for example Boc or phthaloyl in the presence of base such as DBU, cesium carbonate or sodium hydride to give the corresponding alkoxy substituted derivatives (iv). The products like (iv) obtained via this method can then either be liberated or, if a suitable amino functionality is present, be reacted with suitable aldehydes or ketones in the presence of a reducing agent like sodium triacetoxy borohydride, sodium borohydride or sodium cyanoborohydride in a suitable solvent and in the presence of a water withdrawing agent like molecular sieves or a suitable ortho ester. This amino group may have to be liberated in an initial step like for example acidic removal of Boc-groups.

Isoquinoline derivatives like (iv) can be obtained as free bases or as various salts like for example hydrochlorides, hydrobromides, phosphates, trifluoroacetates, sulfates or fumarates. The salts obtained can be converted into the corresponding free base by either subjecting them to ion exchange chromatography or for example by alkaline aqueous treatment and subsequent extraction with suitable organic solvents like for example methyl tert. butyl ether, chloroform, ethyl acetate or isopropanol/dichloromethane mixtures and subsequent evaporation to dryness.

The general methods for the preparation of isoquinoline derivatives as described above can be readily adapted to the preparation of the compounds of the formula (I). In the following examples the preparation of the compounds of the present invention is outlined in more detail.

Accordingly, the following examples are part of and intended to illustrate but not to limit the present invention.

It is understood that modifications that do not substantially affect the activity of the various embodiments of this invention are included within the invention disclosed herein.

LCMS Methods

| Method #1 | |
|---|---|
| Column: | YMC J'sphere 33 × 2 4 μm |
| Gradient: | (ACN + 0.05% TFA):(H$_2$O + 0.05% TFA) |
| | 5:95 (0 min) to 95:5 (2.5 min) to 95:5 (3.0 min) |
| Flow: | 1 ml/min |

| Method #2 | |
|---|---|
| Column: | YMC J'sphere 33 × 2 4 μm |
| Gradient: | (ACN + 0.05% TFA):(H$_2$O + 0.05% TFA) |
| | 5:95 (0 min) to 95:5 (3.4 min) to 95:5 (4.4 min) |
| Flow: | 1 ml/min |

| Method #3 | |
|---|---|
| Column: | YMC J'sphere 33 × 2 4 μm |
| Gradient: | (ACN + 0.08% FA:H₂O + 0.1% FA) |
| | 5:95 (0 min) to 95:5 (2.5 min) to 95:5 (3 min) |
| Flow: | 1 ml/min |

| Method #4: | |
|---|---|
| Column: | YMC Jsphere ODS H80 20 × 2 4 μM |
| Gradient: | ACN:H₂O + 0.05% TFA |
| | 4:96 (0 min) to 95:5 (2.0 min) to 95:5 (2.4 min) |
| Flow: | 1 ml/min |

5-Chloroisoquinoline-6-ol (1)

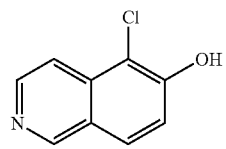 [SMILES: Oc1ccc2cnccc2c1Br]

0.61 mL (1.02 g, 7.6 mmol) of sulfuryl chloride were added to a solution of 1.0 g (6.9 mmol) of 6-hydroxy-isoquinoline in 30 mL of dichloromethane. Three drops diethyl ether were added and the reaction was stirred at room temperature for 5 h. The solvents were removed by distillation and the remainder was treated with aqueous NaHCO₃ solution. The precipitate was filtered, washed with water and dried to give 1.1 g (89%) of 1 as a green-yellow solid.

¹H-NMR (d₆-DMSO): δ=11.37 (1H, s), 9.18 (1H, s), 8.50 (1H, d, J=6 Hz), 8.00 (1H, d, J=8.8 Hz), 7.83 (1H, J=6 Hz), 7.44 (1H, d, J=8.7 Hz).

MS: m/z=180 (MH⁺).

5-Bromoisoquinoline-6-ol (2)

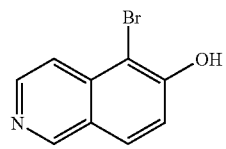

7.9 mL (19.18 g, 120 mmol) of bromine were added dropwise to a suspension of 17.42 g (120 mmol) of 6-hydroxy isoquinoline in 250 mL of chloroform at room temperature. After stirring for 2 h, ethyl acetate was added. The precipitate was filtered, washed with ethyl acetate and dried. Aqueous NaHCO₃ solution was added carefully. The precipitate was filtered and washed with NaHCO₃ solution until the filtrate had a pH of 8. Drying gave 23.78 g (88%) of 2 as an off-white solid.

¹H-NMR (d₆-DMSO): δ=11.30 (1H, s), 9.13 (1H, s), 8.48 (1H, d, J=5.9 Hz), 8.02 (1H, d, J=8.8 Hz), 7.78 (1H, J=5.9 Hz), 7.40 (1H, d, J=8.8 Hz).

MS: m/z=224 (MH⁺).

(2,2-Dimethoxy-ethyl)-(4-fluoro-benzyl)-amine (3)

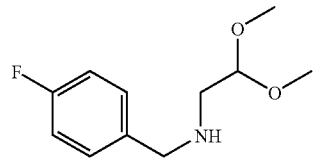

12.4 g of 4-Fluorobenzaldehyde were dissolved in 100 ml of toluene and reacted with 10.5 g 2-aminoacetaldehyde dimethylacetal and 1.90 g (10 mmol) p-toluenesulfonic acid monohydrate for two hours at a Dean Stark apparatus. The solution was allowed to cool down, extracted with saturated sodium bicarbonate, water and brine, dried over magnesium sulfate and evaporated to dryness. The crude product was dissolved in 100 ml of ethanol. 1.89 g of sodium borohydride were added portionwise. Stirring was continued overnight. For workup, acetic acid was added until no gas evolution could be observed. Then the solution was evaporated to dryness, taken up in dichloromethane and washed twice with water. The organic layer was extracted with brine, dried over magnesium sulfate and evaporated to dryness. The obtained crude product (20 g) was used without purification. R$_t$=0.86 min (Method #1). Detected mass: 182.1 (M–OMe⁻), 214.2 (M+H⁺).

N-(2,2-Dimethoxy-ethyl)-N-(4-fluoro-benzyl)-4-methyl-benzene-sulfonamide (4)

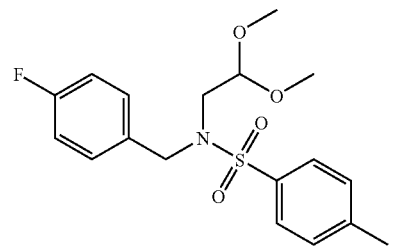 [SMILES: COC(CN(Cc1ccc(F)cc1)S(=O)(=O)c1ccc(C)cc1)OC]

20 g (2,2-Dimethoxy-ethyl)-(4-fluoro-benzyl)-amine (3) were dissolved in 120 ml of dichloromethane. 20 ml of pyridine were added. At 0° C. a solution of 23.8 g p-toluene sulfonic acid chloride in dichloromethane was added dropwise. The reaction was allowed to warm to room temperature and stirring was continued until conversion was completed. For workup, the reaction mixture was extracted twice with 2M hydrochloric acid, twice with sodium bicarbonate and once with brine. The organic layer was dried over magnesium sulfate, evaporated to dryness and the obtained crude product was purified by silica gel chromatography to yield 22.95 g of 4 as an orange oil. R$_t$=1.71 min (Method #4). Detected mass: 336.1 (M–OMe⁻).

6-Fluoro-isoquinoline (5)

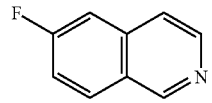

41.6 g AlCl₃ were suspended in 400 ml of dichloroethane. At room temperature, a solution of 22.95 g of N-(2,2-dimethoxy-ethyl)-N-(4-fluoro-benzyl)-4-methyl-benzenesulfonamide (4) in 150 ml of dichloroethane was added. Stirring was continued at room temperature overnight, the solution was poured on ice, the organic layer was separated, the aqueous phase was extracted twice with dichloromethane and the combined organic layers were then extracted twice with sodium bicarbonate solution. The organic layer was dried over magnesium sulfate, evaporated to dryness and the obtained crude product (8.75 g) was purified by silica gel chromatography to yield 2.74 g of 5. $R_t$=0.30 min (Method #4). Detected mass: 148.1 (M+H⁺).

7-Chloro-6-fluoro-isoquinoline (6)

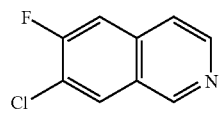 [SMILES: Fc1cc2ccncc2cc1Cl]

Starting from 3-chloro-4-fluoro-benzaldehyde, the title compound was prepared by the same reaction sequence as 6-fluoro-isoquinoline (5). $R_t$=0.77 min (Method #2). Detected mass: 182.1/184.1 (M+H⁺).

7-Methoxy-6-fluoro-isoquinoline (7)

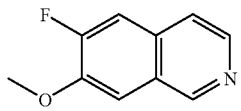

Starting from 3-methoxy-4-fluoro-benzaldehyde, the title compound was prepared by the same reaction sequence as 6-fluoro-isoquinoline (5). $R_t$=0.70 min (Method #4). Detected mass: 178.1 (M+H⁺).

5-Chloro-6-fluoro-isoquinoline (8)

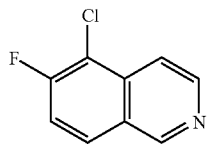

7.0 g (38.1 mmol) 6-Fluoroisoquinoline (5) were dissolved in 60 ml concentrated sulfuric acid. At 0° C. 10.18 g N-chlorosuccinimide were added. After 1 h another 5.2 g of N-chlorosuccinimide were added and the solution was warmed to 50° C. Two more portions of 5.2 g N-chlorosuccinimide were added successively and stirring was continued at 50° C. until the reaction was complete. The reaction mixture was cooled to room temperature, poured on ice and adjusted to pH 10 by addition of sodium hydroxide. The precipitate was filtered off, taken up in dichloromethane and washed with aqueous sodium hydroxide. The organic layer was dried over magnesium sulfate, evaporated and the crude product was purified by preparative HPLC to yield 4.04 g of the desired product as trifluoroacetate. $R_t$=0.97 min (Method #2). Detected mass: 182.0/184.0 (M+H⁺).

4-Chloro-6-fluoro-isoquinoline (9)

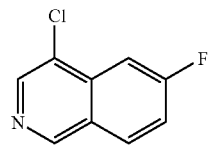 [SMILES: Fc1ccc2cncc(Cl)c2c1]

A solution of 1.5 g 6-fluoro-isoquinoline (5) in 4.5 ml sulfuryl chloride was heated to 60° C. in a microwave reactor (CEM Discovery) for 8 h. After cooling to room temperature the mixture was poured on ice and extracted three times with CHCl₃. After drying over Na₂SO₄ the solvent was distilled off and the crude product was purified by flash chromatography to yield 930 mg of 9. $R_t$=1.37 min (Method #1). Detected mass: 182.0 (M+H⁺).

trans-[4-(7-Chloro-isoquinolin-6-yloxy)-cyclohexyl]-carbamic acid tert-butyl ester (10)

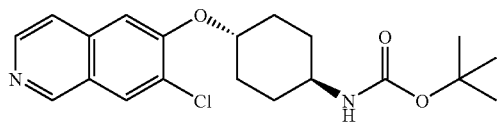 [SMILES: CC(C)(C)OC(=O)N[C@H]1CC[C@H](Oc2cc3ccncc3cc2Cl)CC1]

450 mg (0.21 mmol) trans-(4-Hydroxy-cyclohexyl)-carbamic acid tert-butyl ester were dissolved in 25 ml N,N-dimethyl acetamide. Under an argon atmosphere, 101 mg (4.2 mmol) sodium hydride were added and the mixture was stirred at room temperature. After 30 minutes, 250 mg (0.14 mmol) 7-chloro-6-fluoro-isoquinoline (6) were added and the solution was heated to 80° C. After 4 h, the solvent was removed under reduced pressure. The residue was taken up in H₂O and extracted three times with ethyl acetate. The combined organic layers were dried over MgSO₄ and evaporated. The crude product was purified by preparative HPLC, which delivered 18 mg of the title compound. $R_t$=1.38 min (Method #1). Detected mass: 377.2/379.3 (M+H⁺).

trans-4-(7-Chloro-isoquinolin-6-yloxy)-cyclohexylamine (11)

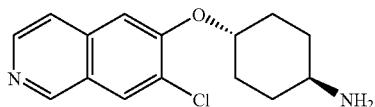

18 mg (0.05 mmol) trans-[4-(5-Chloro-isoquinolin-6-yloxy)-cyclohexyl]-carbamic acid tert-butyl ester (10) were stirred in 2 M HCl at room temperature. After 2 days, the solvent was removed i. vac. and the residue was purified by preparative HPLC. 8 mg of the title compound could be obtained as trifluoro acetate. $R_t$=0.69 min (Method #1). Detected mass: 277.2/279.2 (M+H$^+$).

cis-[4-(5-Chloro-isoquinolin-6-yloxy)-cyclohexyl]-carbamic acid tert-butyl ester (12)

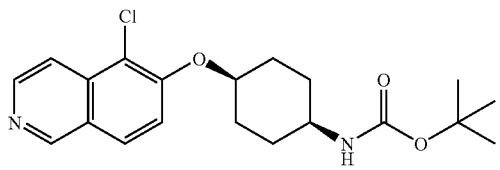 [SMILES: CC(C)(C)OC(=O)N[C@H]1CC[C@@H](Oc2ccc3cnccc3c2Cl)CC1]

Starting from 5-chloro-6-fluoro-isoquinoline (8) and cis-(4-hydroxy-cyclohexyl)-carbamic acid tert-butyl ester the title compound was prepared by the method described for trans-[4-(5-chloro-isoquinolin-6-yloxy)-cyclohexyl]carbamic acid tert-butyl ester (10), whereas DMF was used as solvent. $R_t$=1.14 min (Method #4). Detected mass: 377.2/379.2 (M+H$^+$).

cis-4-(5-Chloro-isoquinolin-6-yloxy)-cyclohexylamine (13)

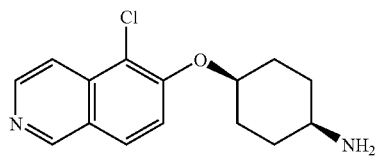 [SMILES: N[C@H]1CC[C@@H](Oc2ccc3cnccc3c2Cl)CC1]

50 mg (0.13 mmol) cis-[4-(5-Chloro-isoquinolin-6-yloxy)-cyclohexyl]carbamic acid tert-butyl ester (12) were dissolved in ethanol/2N HCl (1:1) and stirred at room temperature until complete conversion could be detected (LCMS). Evaporation of the solvent furnished 36 mg of the title compound as hydrochloride. $R_t$=0.71 min (Method #1). Detected mass: 277.2/279.2 (M+H$^+$).

cis-4-(4-Chloro-isoquinolin-6-yloxy)-cyclohexylamine (14)

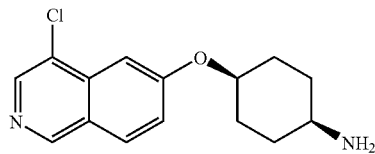 [SMILES: N[C@H]1CC[C@@H](Oc2ccc3cncc(Cl)c3c2)CC1]

Starting from 4-chloro-6-fluoro-isoquinoline (9) and cis-(4-hydroxy-cyclohexyl)-carbamic acid tert-butyl ester the title compound was prepared as hydrochloride by the method described for trans-[4-(5-chloro-isoquinolin-6-yloxy)-cyclohexyl]-carbamic acid tert-butyl ester (10) followed by deprotection using 4M hydrochloric acid in isopropanol. $R_t$=0.79 min (Method #1). Detected mass: 277.1/279.1 (M+H$^+$).

cis-4-(7-methoxy-isoquinolin-6-yloxy)-cyclohexylamine (15)

Starting from 7-methoxy-6-fluoro-isoquinoline (7) and cis-(4-hydroxy-cyclohexyl)-carbamic acid tert-butyl ester the title compound was prepared as trifluoroacetate by the method described for trans-[4-(5-chloro-isoquinolin-6-yloxy)-cyclohexyl]-carbamic acid tert-butyl ester (10) followed by deprotection using 4M hydrochloric acid in isopropanol and purification via preparative HPLC. $R_t$=0.62 min (Method #2). Detected mass: 273.19 (M+H$^+$).

General procedure for the reaction of N-boc-protected minoalcohols with 6-Hydroxy Isoquinolines (Mitsunobu-Reaction):

To 500 mg (1.5 mmol) of triphenylphosphine (bound to polystyrene, 3 mmol/g) and 10 ml of dichloromethane were added 0.195 mL (1.2 mmol) of diethylazodicarboxylate (or alternatively diisopropylazodicarboxylate). The reaction mixture was allowed to shake for 10 min. and then 0.14 mL of triethylamine, 145 mg of the 6-hydroxyisoquinoline derivative (reagent 1) and 1 mmol of the desired, boc-protected aminoalcohol (reagent 2) was added. The reaction was shaken at room temperature until no further conversion could be observed by LCMS. For workup, the solution was filtered, the residue was washed with dichloromethane and the organic layer was washed twice with 1N sodium hydroxide, twice with water and once with brine, dried over magnesium sulfate and evaporated. The crude product was purified by preparative HPLC to yield the boc protected coupled product.

General Procedure for Removal of the Boc-Group:

The starting material was dissolved in 2M hydrochloric acid and stirred overnight. To compounds with poor aqueous solubility, methanol or dioxane was added until a homogenous solution was obtained. Alternatively, 4M hydrochloric acid in isopropanol was used to deprotect the compound. The reaction mixture was lyophilised and the deprotected product was obtained as the corresponding hydrochloride of the free amine.

The following examples were prepared according to this protocol (Table 1):

TABLE 1

| Example # | Product | Reagent 1 | Reagent 2 | LCMS Method # | $R_t$ [min] | Mass [M + H]+ | Chemial Name |
|---|---|---|---|---|---|---|---|
| 16 | (structure) | 6-hydroxy-isoquinoline | trans-(4-Hydroxy-cyclohexyl)-carbamic acid tert-butyl ester | 1 | 0.60 | 243.14 | cis-4-(Isoquinolin-6-yloxy)-cyclohexylamine |

TABLE 1-continued

| Example # | Product | Reagent 1 | Reagent 2 | LCMS Method # | R$_t$ [min] | Mass [M + H]+ | Chemical Name |
|---|---|---|---|---|---|---|---|
| 17 | (isoquinoline with O-cyclohexyl-NH₂, trans) | 6-hydroxy-isoquinoline | cis-(4-Hydroxy-cyclohexyl)-carbamic acid tert-butyl ester | 1 | 0.72 | 243.23 | trans-4-(Isoquinolin-6-yloxy)-cyclohexylamine |
| 13 | (5-Cl-isoquinoline with O-cyclohexyl-NH₂, cis) HCl | 1 | trans-(4-Hydroxy-cyclohexyl)-carbamic acid tert-butyl ester | 1 | 0.72 | 277.10 | cis-4-(5-Chloro-isoquinolin-6-yloxy)-cyclohexylamine |
| 18 | (5-Br-isoquinoline with O-cyclohexyl-NH₂, trans) | 2 | cis-(4-Hydroxy-cyclohexyl)-carbamic acid tert-butyl ester | 1 | 0.80 | 321.05/ 323.16 | trans-4-(5-Bromo-isoquinolin-6-yloxy)-cyclohexylamine |
| 19 | (5-Br-isoquinoline with O-cyclohexyl-NH₂, cis) | 2 | trans-(4-Hydroxy-cyclohexyl)-carbamic acid tert-butyl ester | 1 | 0.75 | 321.16/ 323.16 | cis-4-(5-Bromo-isoquinolin-6-yloxy)-cyclohexylamine |

The examples 16 and 17 were also synthesized using a similar method as described for the synthesis of 12 and 13. The respective starting materials are 6-fluoro isoquinoline (5) and either cis or trans 4-amino-cyclohexanol hydrochloride.

(3-Fluoro-benzyl)-[cis-4-(isoquinolin-6-yloxy)-cyclohexyl]-amine (20)

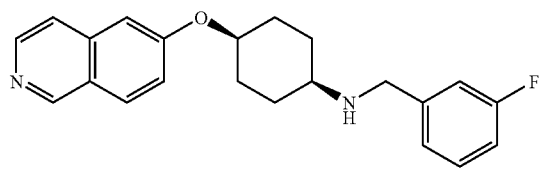 [SMILES: Fc1cccc(CN[C@H]2CC[C@@H](Oc3ccc4cnccc4c3)CC2)c1]

100 mg (0.36 mmol) cis-4-(Isoquinolin-6-yloxy)-cyclohexylamine (16) were dissolved in 15 ml dichloromethane. At room temperature 53.6 mg (0.43 mmol) 3-fluoro benzaldehyde, 29.5 mg (0.36 mmol) sodium acetate, 10.8 mg (0.18 mmol) acetic acid and freshly dried molecular sieves were added and the reaction mixture was stirred at room temperature. After 1 h 91.2 mg (0.43 mmol) sodium triacetoxy borohydride were added and stirring was continued. After 3 h additional 2 equivalents of sodium triacetoxy borohydride were added and the reaction was stirred until complete conversion could be detected. For working up, acetic acid was added to destroy excess boron hydride reagent and the mixture was filtered. The filtrate was dissolved in dichloromethane and washed twice with saturated sodium bicarbonate solution. The organic layer was separated, dried over MgSO$_4$ and evaporated. Final purification by preparative HPLC delivered the title compound as trifluoro acetate, which was dissolved in 1 N HCl. Lyophilization furnished the corresponding HCl-salt. After a second lyophilization from H$_2$O, 28.6 mg of the desired compound could be obtained as hydrochloride. R$_t$=0.96 min (Method #1). Detected mass: 351.3 (M+H⁺).

Starting from cis-4-(Isoquinolin-6-yloxy)-cyclohexylamine and corresponding aldehydes, the following compounds were prepared by the protocol, described for 20:

TABLE 2

| Example # | Aldehyde | Product | Chemical name | R$_t$ [min] | LCMS Method # | Detected mass; [M + H⁺] |
|---|---|---|---|---|---|---|
| 21 | propanal (CH₃CH₂CHO) | cis-[4-(Isoquinolin-6-yloxy)-cyclohexyl]-N-propyl-amine · ClH | cis-[4-(Isoquinolin-6-yloxy)-cyclohexyl]-propyl-amine | 0.76 | 1 | 285.3 |

TABLE 2-continued

| Ex-am-ple # | Aldehyde | Product | Chemical name | $R_t$ [min] | LCMS Method # | Detected mass; [M + H+] |
|---|---|---|---|---|---|---|
| 22 | F₃C-CH₂-CHO · ClH | (structure) | cis-[4-(Isoquinolin-6-yloxy)-cyclohexyl]-(3,3,3-trifluoro-propyl)-amine | 0.86 | 1 | 339.3 |
| 23 | pyridine-3-carbaldehyde | (structure) · TFA | cis-[4-(Isoquinolin-6-yloxy)-cyclohexyl]-pyridin-3-ylmethyl-amine | 0.67 | 1 | 334.2 |
| 24 | cyclopropane-CHO | (structure) · TFA | Cyclopropylmethyl-cis-[4-(isoquinolin-6-yloxy)-cyclohexyl]-amine | 0.81 | 1 | 297.2 |
| 25 | isobutyraldehyde | (structure) · TFA | Isobutyl-cis-[4-(isoquinolin-6-yloxy)-cyclohexyl]-amine | 0.84 | 1 | 299.2 |
| 26 | acetone | (structure) · TFA | Isopropyl-cis-[4-(isoquinolin-6-yloxy)-cyclohexyl]-amine | 0.80 | 1 | 285.2 |

4-(Isoquinolin-6-yloxy)-cyclohexanone (27)

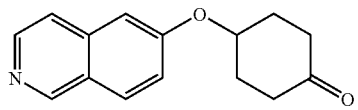 [SMILES: O=C1CCC(Oc2ccc3cnccc3c2)CC1]

A suspension of 9 g triphenylphosphine (bound to polystyrene, Argonaut, 1.6 mmol/g, 14.4 mmol) and 1.57 mL (1.74 g, 10 mmol) diethyl azocarboxylate in 100 mL dichloromethane was stirred for 10 min under argon atmosphere. Then 1.45 g (10 mmol) 6-hydroxy-isoquinoline and 1.58 g (10 mmol) 1,4-dioxa-spiro[4.5]decan-8-ol were added. After 40 min 1.39 mL (1 g, 10 mmol) triethyl amine was added and the reaction was allowed to shake for 16 h at room temperature. After filtration the organic layer was extracted with 1N NaOH, dried over Na₂SO₄, filtered and concentrated in vacuo.

The crude material (2.2 g) was dissolved in 200 mL acetone and 10 mL water. 1.5 g (7.9 mmol) of para-toluene sulfonic acid were added and the reaction was heated to reflux temperature for 6 h. Then the solvents were distilled off. The remainder was dissolved in dichloromethane and was extracted with aqueous Na₂CO₃ solution. After drying over Na₂SO₄, filtration and removal of the solvents the crude product was purified by flash chromatography to yield 1.19 g of 27 as a white solid.

$^1$H-NMR (d$_6$-DMSO): δ=9.16 (1H, s), 8.41 (1H, d, J=5.8 Hz), 8.05 (1H, d, J=8.9 Hz), 7.70 (1H, d, J=5.8 Hz), 7.51 (1H, d, J=2.5 Hz), 7.36 (1H, dd, J=8.9 und 2.5 Hz), 5.04 (1H, m), 2.44 (4H, m), 2.22 (2H, m), 2.11 (2H, m).

MS: m/z=242 (MH$^+$).

General procedure for preparation of 4-(isoquinolin-6-yloxy)-cyclohexylamines

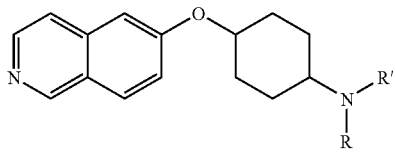

1.2 eq amine and 2.5 eq MP-triacetoxyborohydride (Argonaut, 2 mmol/g) were added to a solution of 60 mg (0.25 mmol, 1 eq.) 4-(isoquinolin-6-yloxy)-cyclohexanone (27) in 2 mL dry THF and allowed to shake for 16 h at room temperature. Upon completion the polymer was removed by filtration and washed with THF. Removal of the solvent gave the crude product which was purified by preparative HPLC if necessary. The title compounds were obtained as a mixture of cis and trans isomers.

The following examples were synthesized according to this procedure:

TABLE 3

| Example | Product | Amine | LCMS Method | retention time | detected mass [M + H]+ | Chemical Name |
|---|---|---|---|---|---|---|
| 28 | | | 1 | 0.80 0.82 | 283.25 283.25 | Cyclopropyl-[4-(isoquinolin-6-yloxy)-cyclohexyl]-amine |
| 29 | | | 2 | 0.59 | 271.22 | [4-(Isoquinolin-6-yloxy)-cyclohexyl]-dimethyl-amine |
| 30 | | | 2 | 0.68 | 269.20 | Ethyl-[4-(isoquinolin-6-yloxy)-cyclohexyl]-pyridin-4-ylmethyl-amine |

TABLE 3-continued

| Example | Product | Amine | LCMS Method | retention time | detected mass [M + H]+ | Chemical Name |
|---|---|---|---|---|---|---|
| 31 | | | 1 | 0.90 / 0.93 | 347.22 / 347.22 | benzyl-[4-(isoquinolin-6-yloxy)-cyclohexyl]-methyl-amine |
| 32 | | | 1 | 1.21 / 1.23 | 425.20 / 425.21 | [4-(Isoquinolin-6-yloxy)-cyclohexyl]-(4-phenoxy-benzyl)-amine |
| 33 | | | 1 | 1.07 / 1.10 | 430.26 / 430.26 | [4-(Isoquinolin-6-yloxy)-cyclohexyl]-[5-(4-methoxy-phenyl)-isoxazol-3-ylmethyl]-amine |

TABLE 3-continued

| Example | Product | Amine | LCMS Method | retention time | detected mass [M + H]+ | Chemical Name |
|---|---|---|---|---|---|---|
| 34 | | | 2 | 0.87 | 390.19 | N-(4-{[4-(Isoquinolin-6-yloxy)-cyclohexylamino]-methyl}-phenyl)-acetamide |
| 35 | | | 1 | 0.97 0.99 | 363.22 363.22 | (4-(Isoquinolin-6-yloxy)-cyclohexyl]-(4-methoxy-benzyl)-amine |
| 36 | | | 1 | 1.02 | 367.20 | (4-Chloro-benzyl)-[4-(isoquinolin-6-yloxy)-cyclohexyl]-amine |

TABLE 3-continued

| Example | Product | Amine | LCMS Method | retention time | detected mass [M + H]+ | Chemical Name |
|---|---|---|---|---|---|---|
| 37 | | | 1 | 1.03<br>1.05 | 393.26<br>393.26 | (2,3-Dimethoxy-benzyl)-[4-(isoquinolin-6-yloxy)-cyclohexyl]-amine |
| 38 | | | 1 | 0.87<br>0.89 | 445.28<br>445.28 | 5-(4-{[4-(isoquinolin-6-yloxy)-cyclohexylamino]-methyl}-phenyl)-5-methyl-imidazolidine-2,4-dione |
| 39 | | | 1 | 0.95<br>0.98 | 393.24<br>393.24 | (3,5-Dimethoxy-benzyl)-[4-(isoquinolin-6-yloxy)-cyclohexyl]-amine |

TABLE 3-continued

| Example | Product | Amine | LCMS Method | retention time | detected mass [M + H]+ | Chemical Name |
|---|---|---|---|---|---|---|
| 40 | | | 1 | 0.90<br>0.92 | 358.21<br>358.21 | 3-{[4-(Isoquinolin-6-yloxy)-cyclohexylamino]-methyl}-benzonitrile |
| 41 | | | 1 | 0.90<br>0.92 | 411.23<br>411.23 | [4-(Isoquinolin-6-yloxy)-cyclohexyl]-(4-methanesulfonyl-benzyl)-amine |
| 42 | | | 1 | 1.05<br>1.06 | 400.30<br>400.30 | [2-(1H-Indol-3-yl)-ethyl]-[4-(isoquinolin-6-yloxy)-cyclohexyl]-methyl-amine |

TABLE 3-continued
| Example | Product | Amine | LCMS Method | retention time | detected mass [M + H]+ | Chemical Name |
|---|---|---|---|---|---|---|
| 43 | 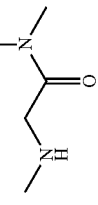 |  | 1 | 0.76 | 342.28 | 2-{[4-(Isoquinolin-6-yloxy)-cyclohexyl]-methyl-amino}-N,N-dimethyl-acetamide |
| 44 | 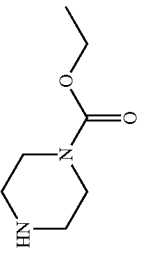 | 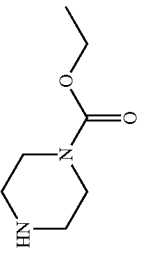 | 1 | 0.86 | 384.29 | 4-[4-(Isoquinolin-6-yloxy)-cyclohexyl]-piperazine-1-carboxylic acid ethyl ester |

TABLE 3-continued
| Example | Product | Amine | LCMS Method | retention time | detected mass [M + H]+ | Chemical Name |
|---|---|---|---|---|---|---|
| 45 | 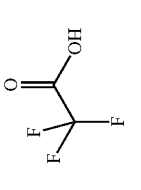 | 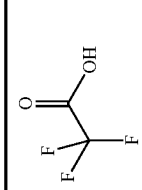 | 2 | 0.76 | 313.24 | Isobutyl-[4-(isoquinolin-6-yloxy)-cyclohexyl]-methyl-amine |
| 46 | 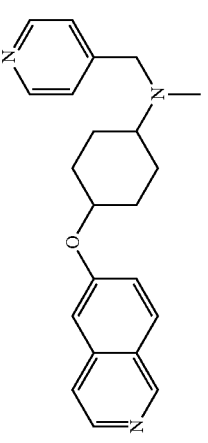 | 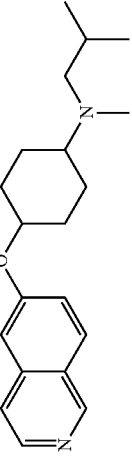 | 2 | 0.61 | 348.23 | [4-(Isoquinolin-6-yloxy)-cyclohexyl]-methyl-pyridin-4-ylmethyl-amine |

TABLE 3-continued

| Example | Product | Amine | LCMS Method | retention time | detected mass [M + H]+ | Chemical Name |
|---|---|---|---|---|---|---|
| 47 | | | 2 | 0.59 0.75 | 329.24 329.24 | Ethyl-[4-(isoquinolin-6-yloxy)-cyclohexyl]-(2-methoxy-ethyl)-amine |
| 48 | | | 2 | 0.90 | 358.21 | 4-{[4-(Isoquinolin-6-yloxy)-cyclohexylamino]-methyl}-benzonitrile |

TABLE 3-continued
| Example | Product | Amine | LCMS Method | retention time | detected mass [M + H]+ | Chemical Name |
|---|---|---|---|---|---|---|
| 49 | 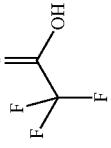 | 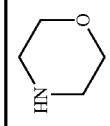 | 2 | 0.65 | 313.21 | 6-(4-Morpholin-4-yl-cyclohexyloxy)-isoquinoline |
| 50 | 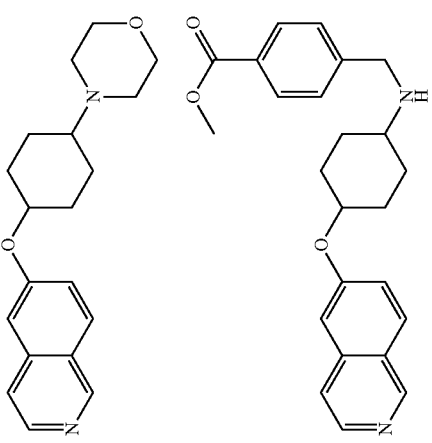 | 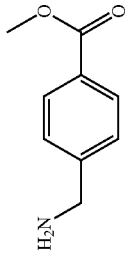 | 1 | 0.98 1.00 | 391.22 391.22 | 4-{[4-(Isoquinolin-6-yloxy)-cyclohexylamino]-methyl}-benzoic acid methyl ester |

TABLE 3-continued

| Example | Product | Amine | LCMS Method | retention time | detected mass [M + H]+ | Chemical Name |
|---|---|---|---|---|---|---|
| 51 | | | 1 | 1.21, 1.22 | 389.31, 389.31 | (4-tert-Butyl-benzyl)-[4-(isoquinolin-6-yloxy)-cyclohexyl]-amine |
| 52 | | | 2 | 1.10 | 431.25 | [1-(4-Fluoro-phenyl)-1H-pyrazol-4-ylmethyl]-[4-(isoquinolin-6-yloxy)-cyclohexyl]-methyl-amine |
| 53 | | | 2 | 1.07 | 414.18 | [4-(Isoquinolin-6-yloxy)-cyclohexyl]-(5-methyl-3-phenyl-isoxazol-4-ylmethyl)-amine |

TABLE 3-continued

| Example | Product | Amine | LCMS Method | retention time | detected mass [M + H]+ | Chemical Name |
|---|---|---|---|---|---|---|
| 54 | | | 1 | 1.08 1.09 | 383.25 383.25 | [4-(Isoquinolin-6-yloxy)-cyclohexyl]-naphthalen-1-ylmethyl-amine |
| 55 | | | 1 | 1.14 1.15 | 416.25 416.25 | [4-(Isoquinolin-6-yloxy)-cyclohexyl]-(2-phenyl-oxazol-4-ylmethyl)-amine |
| 56 | | | 1 | 0.97 1.00 | 375.28 375.28 | (2,3-Dihydro-benzofuran-5-ylmethyl)-[4-(isoquinolin-6-yloxy)-cyclohexyl]-amine |

TABLE 3-continued

| Example | Product | Amine | LCMS Method | retention time | detected mass [M + H]+ | Chemical Name |
|---|---|---|---|---|---|---|
| 57 | | | 1 | 0.84 / 0.86 | 338.23 / 338.23 | [4-(Isoquinolin-6-yloxy)-cyclohexyl]-(5-methyl-isoxazol-3-ylmethyl)-amine |
| 58 | | | 1 | 1.09 / 1.12 | 422.20 / 422.20 | [4-(Isoquinolin-6-yloxy)-cyclohexyl]-(2-thiophen-2-yl-thiazol-4-ylmethyl)-amine |
| 59 | | | 1 | 1.12 / 1.15 | 361.25 / 361.25 | (3,5-Dimethyl-benzyl)-[4-(isoquinolin-6-yloxy)-cyclohexyl]-amine |

TABLE 3-continued

| Example | Product | Amine | LCMS Method | retention time | detected mass [M + H]+ | Chemical Name |
|---|---|---|---|---|---|---|
| 60 | | | 2 | 1.22 | 409.19 | Biphenyl-2-ylmethyl-[4-(isoquinolin-6-yloxy)-cyclohexyl]-amine |
| 61 | | | 1 | 0.91 0.94 | 399.26 399.26 | [4-(Isoquinolin-6-yloxy)-cyclohexyl]-(4-pyrazol-1-yl-benzyl)-amine |
| 62 | | | 1 | 0.80 0.84 | 349.18 349.19 | [4-(Isoquinolin-6-yloxy)-cyclohexyl]-(4-methoxy-phenyl)-amine |

'The cis/trans mixtures were separated into the stereoisomers by preparative HPLC on a chiral column (Chiralpak AD/H-39). The following compounds were isolated this way as trifluoroacetates:

TABLE 4

| Example # | Product | Chemical Name | LCMS Method # | retention time | detected mass [M + H]$^+$ |
|---|---|---|---|---|---|
| 63 | | trans-Cyclopropyl-[4-(isoquinolin-6-yloxy)-cyclohexyl]-amine | 1 | 0.79 | 283.36 |
| 64 | | cis-Cyclopropyl-[4-(isoquinolin-6-yloxy)-cyclohexyl]-amine | 1 | 0.76 | 283.33 |
| 65 | | trans-[4-(Isoquinolin-6-yloxy)-cyclohexyl]-(4-phenoxy-benzyl)-amine | 1 | 1.23 | 425.26 |
| 66 | | cis-[4-(Isoquinolin-6-yloxy)-cyclohexyl]-(4-phenoxy-benzyl)-amine | 1 | 1.20 | 425.25 |
| 67 | | trans-Benzyl[4-(isoquinolin-6-yloxy)-cyclohexyl]-methyl-amine | 1 | 0.97 | 347.26 |
| 68 | | cis-Benzyl-[4-(isoquinolin-6-yloxy)-cyclohexyl]-methyl-amine | 1 | 0.99 | 347.25 |
| 69 | | trans-[4-(Isoquinolin-6-yloxy)-cyclohexyl]-dimethyl-amine | 2 | 0.61 | 271.16 |

TABLE 4-continued

| Example # | Product | Chemical Name | LCMS Method # | retention time | detected mass [M + H]+ |
|---|---|---|---|---|---|
| 70 | | cis-[4-(Isoquinolin-6-yloxy)-cyclohexyl]-dimethyl-amine | 2 | 0.58 | 271.16 |
| 71 | | trans-N-(4-{[4-(Isoquinolin-6-yloxy)-cyclohexylamino]-methyl}-phenyl)-acetamide | 1 | 0.82 | 390.33 |
| 72 | | cis-N-(4-{[4-(Isoquinolin-6-yloxy)-cyclohexylamino]-methyl}-phenyl)-acetamide | 1 | 0.93 | 390.36 |

The relative stereochemistry of 70 was confirmed by this alternative synthesis:

[4-(Isoquinolin-6-yloxy)-cyclohexyl]-dimethyl-amine (70)

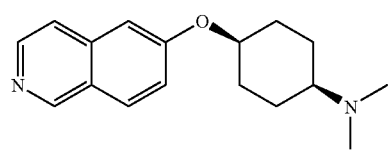 [SMILES: CN(C)[C@H]1CC[C@@H](Oc2ccc3cnccc3c2)CC1]

435 mg para-formaldehyde (5.2 mmol, 2.2 eq.) were added to a solution of 660 mg 16 (2.4 mmol) in 5.4 g (50 eq.) formic acid. The mixture was heated to reflux for two hours. Another 0.25 equivalents of para formaldehyde were added and the mixture was heated again for 2 hours to reflux temperature. After cooling the solvent was removed in vacuo. 5 ml 2 N aqueous NaOH and $CH_3Cl$/i-Propanol 3:1 were added. The mixture was filtered through a PTS-cartridge. After washing the combined fractions were evaporated and the crude product was purified by preparative HPLC chromatography.

The product was dissolved in 10 mL isopropanol. 5-6 N HCl in isopropanol was added and the solvents were removed in vacuo to yield 200 mg of the title compound as a hydrochloride.

2-Chloro-N-dimethylaminomethylene-5-formyl-benzenesulfonamide (73)

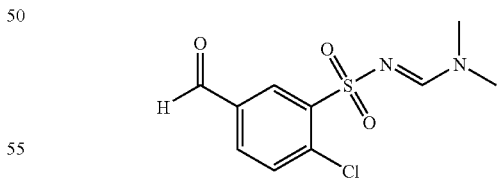

5.0 g (22.8 mmol) 2-Chloro-5-formyl-benzenesulfonamide were dissolved in 50 ml dichloromethane. 4.08 g (34.3 mmol) dimethylformamide dimethylacetal were added and the mixture was refluxed for 2 h. After cooling to room temperature, the solution was washed twice with $H_2O$, dried over magnesium sulfate and evaporated. 5.16 g of the crude product were obtained and used in the next step without further purification. $R_t$=1.14 min (Method #1). Detected mass: 275.1/277.1 (M+H+).

2-Chloro-5-{cis-[4-(5-chloro-isoquinolin-6-yloxy)-cyclohexylamino]-methyl}-N-dimethylaminomethylene-benzenesulfonamide (74)

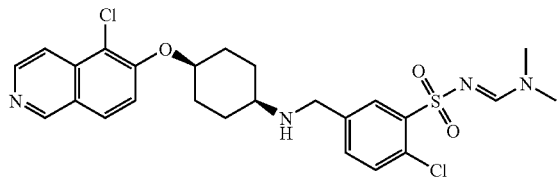 [SMILES: CN(C)/C=N/S(=O)(=O)c1cc(CN[C@H]2CC[C@@H](Oc3ccc4cnccc4c3Cl)CC2)ccc1Cl]

34 mg (0.11 mmol) cis-4-(5-Chloro-isoquinolin-6-yloxy)-cyclohexylamine (13) were dissolved in 5 ml MeOH and 22 mg (0.22 mmol) triethylamine were added. After the reaction was stirred 30 min, 65 mg (1.1 mmol) acetic acid, 60 mg (0.22 mmol) 2-chloro-N-dimethylaminomethylene-5-formyl-benzenesulfonamide (73) and freshly dried molecular sieves were added and the mixture was stirred for 30 minutes at room temperature. A solution of 20.5 mg (0.33 mmol) sodium cyanoborohydride in 1 ml methanol was added and the mixture was allowed to stand at room temperature overnight. The solvent was removed i. vac. The residue was dissolved in dichloromethane, washed with 1N NaOH and brine, dried over MgSO$_4$ and evaporated. 53 mg of the title compound were isolated as crude product and used without further purification. R$_t$=0.87 min (Method #4). Detected mass: 535.2/537.1 (M+H$^+$).

2-Chloro-5-{[4-(5-chloro-isoquinolin-6-yloxy)-cyclohexylamino]-methyl}-benzenesulfonamide (75)

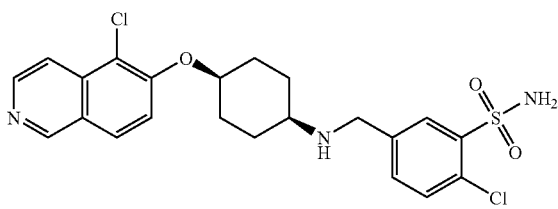 [SMILES: NS(=O)(=O)c1cc(CN[C@H]2CC[C@@H](Oc3ccc4cnccc4c3Cl)CC2)ccc1Cl]

53 mg 2-Chloro-5-{cis-[4-(5-chloro-isoquinolin-6-yloxy)-cyclohexylamino]-methyl}-N-dimethylaminomethylene-benzenesulfonamide (74) were dissolved in 5 ml ethanol. 2 ml 2N NaOH were added and the mixture was heated to 65° C. After 5 h, the solvent was removed i. vac., the residue was dissolved in H$_2$O and neutralized by adding 1 N HCl. The precipitate was filtered and dried, to yield 23 mg of the title compound as hydrochloride. R$_t$=0.89 min (Method #1). Detected mass: 480.2/484.2 (M+H$^+$).

Cyclopropylmethyl-[trans-4-(isoquinolin-6-yloxy)-cyclohexyl]-amine (76)

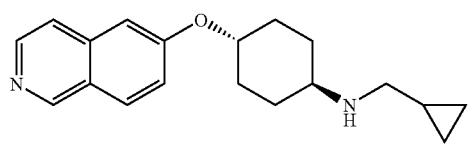 [SMILES: c1cc2cc(O[C@H]3CC[C@H](NCC4CC4)CC3)ccc2cn1]

A suspension of 69.7 mg (0.25 mmol) trans-4-(isoquinolin-6-yloxy)-cyclohexylamine (17), 52.7 µL triethyl amine (1.25 mmol, 5 eq.) and 21 mg cyclopropanecarbaldehyde (0.3 mmol, 1.2 eq.) in 3 mL trimethylorthoformate was stirred at room temperature for 1 h. Then a solution of 321.6 mg sodium triacetoxy borohydride (1.25 mmol, 5 eq) and 72 µL acetic acid (75.1 mg, 1.25 eq) in 2 mL DMF was added. The reduction was complete after 10 min. Then the solvents were removed in vacuo and the product was isolated via preparative HPLC to yield 41 mg of the title compound as trifluoroacetate. R$_t$=0.89 min (Method #1). Detected mass: 297.3 (M+H$^+$).

Bis-cyclopropylmethyl-[trans-4-(isoquinolin-6-yloxy)-cyclohexyl]amine (77)

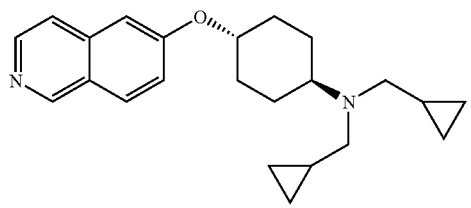 [SMILES: c1cc2cc(O[C@H]3CC[C@H](N(CC4CC4)CC4CC4)CC3)ccc2cn1]

The title compound as trifluoroacetate was isolated as side product in the reaction described for cyclopropylmethyl-[trans-4-(isoquinolin-6-yloxy)-cyclohexyl]-amine (76). R$_t$=0.97 min (Method #1). Detected mass: 351.2 (M+H$^+$).

5-Chloro-6-(1,4-dioxa-spiro[4.5]dec-8-yloxy)-isoquinoline (78)

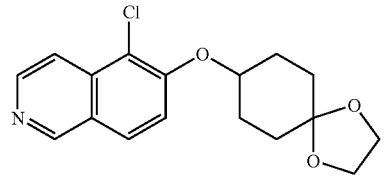 [SMILES: Clc1c(OC2CCC3(CC2)OCCO3)ccc2cnccc12]

887 mg (5.61 mmol) 1,4-Dioxa-spiro[4.5]decan-8-ol were dissolved in 50 ml DMF and 224 mg (5.61 mmol) sodium hydride (60%) were added. After stirring for 30 minutes at room temperature, a solution of 815 mg (4.49 mmol) 5-chloro-6-fluoro-isoquinoline (8) in 10 ml DMF was added and the mixture was heated to 100° C. After 4 h one additional equivalent of 1,4-dioxa-spiro[4.5]decan-8-ol and sodium hydride were added and stirring was continued at 100° C. After 1.5 h complete conversion could be detected. For working up, the solvent was removed under reduced pressure, the residue was taken up in H$_2$O and extracted three times with ethyl acetate. The combined organic layers were dried over MgSO$_4$ and evaporated. The obtained orange oil (2.17 g) was stirred in diisopropyl ether and the insoluble white precipitate was filtered off. After drying of the precipitate, 549 mg of the title compound could be isolated. $R_t$=1.15 min (Method #1). Detected mass: 320.1/322.1 (M+H$^+$).

4-(5-Chloro-isoquinolin-6-yloxy)-cyclohexanone (79)

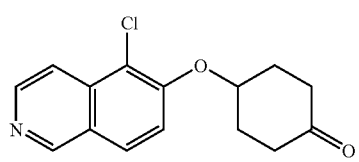 [SMILES: O=C1CCC(Oc2ccc3cnccc3c2Cl)CC1]

549 mg (1.72 mmol) 5-Chloro-6-(1,4-dioxa-spiro[4.5]dec-8-yloxy)-isoquinoline (78) were dissolved in 20 ml THF/H$_2$O (3:1). 1 ml TFA was added and the mixture was stirred at room temperature. After 1 h, 2 ml TFA were added and the temperature was increased to 50° C. After 5 d at 50° C., 2 ml TFA were added. After one additional day, 2 ml TFA were added and the temperature was increased to 100° C. After 5 h, the reaction was allowed to cool down to room temperature and the mixture was diluted with dichloromethane and H$_2$O, Solid NaHCO$_3$ was added for neutralization. The phases were separated and the aqueous phase was extracted with dichloromethane. The combined organic layers were dried over MgSO$_4$ and evaporated. After final purification by preparative HPLC, 533 mg of the title compound as trifluoroacetate were obtained. $R_t$=0.88 min (Method #4). Detected mass: 276.2/278.2 (M+H$^+$).

[4-(5-Chloro-isoquinolin-6-yloxy)-cyclohexyl]-cyclohexyl-amine (80)

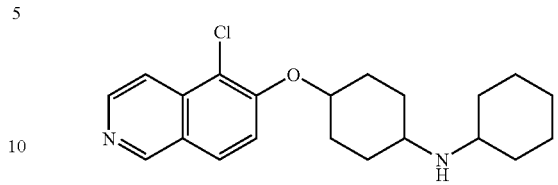

100 mg (0.36 mmol) 4-(5-Chloro-isoquinolin-6-yloxy)-cyclohexanone (79) were dissolved in 10 ml methanol. After adding 73 mg (0.73 mmol) triethyl amine, 108 mg (1.09 mmol) cyclohexylamine, 218 mg (3.63 mmol) acetic acid and freshly dried molecular sieves, the reaction was stirred at room temperature. After 30 minutes, a solution of 68 mg (1.09 mmol) sodium cyanoborohydride in 2 ml methanol was added and the reaction was kept at room temperature until complete conversion was achieved. For working up, the reaction mixture was filtered and the filtrate was brought to alkaline pH by adding solid NaHCO$_3$. After evaporation of the solvent, the residue was taken up in H$_2$O and extracted three times with dichloromethane. The combined organic layers were dried over MgSO$_4$ and evaporated. Final purification by preparative HPLC gave 69 mg of the desired product as trifluoroacetate, which was dissolved in 2 N HCl and lyophilized, to yield 45 mg of the corresponding HCl-salt. $R_t$=1.08/1.15 min (Method #1). Detected mass: 359.3/361.3 (M+H$^+$).

Following the protocol described for [4-(5-Chloro-isoquinolin-6-yloxy)-cyclohexyl]-cyclohexyl-amine (80), the following compounds as cis/trans-mixtures were synthesized as hydrochlorides, starting from 4-(5-chloro-isoquinolin-6-yloxy)-cyclohexanone (79):

TABLE 5

| Example # | Amine | Product | Chemical name | $R_t$ [min] | LCMS Method # | Detected mass; [M + H$^+$] |
|---|---|---|---|---|---|---|
| 81 | ![NH2-cyclopropyl] | ![structure] | [4-(5-Chloro-isoquinolin-6-yloxy)-cyclohexyl]-cyclopropyl-amine | 0.92/0.99 | 1 | 317.3/319.3 |
| 82 | ![NH2-cyclobutyl] | ![structure] | [4-(5-Chloro-isoquinolin-6-yloxy)-cyclohexyl]-cyclobutyl-amine | 0.93/1.01 | 1 | 331.3/333.3 |
| 83 | ![NH2-cyclopentyl] | ![structure] | [4-(5-Chloro-isoquinolin-6-yloxy)-cyclohexyl]-cyclopentyl-amine | 0.91/1.01 | 1 | 345.3/347.3 |

TABLE 5-continued

| Example # | Amine | Product | Chemical name | $R_t$ [min] | LCMS Method # | Detected mass; [M + H+] |
|---|---|---|---|---|---|---|
| 84 | 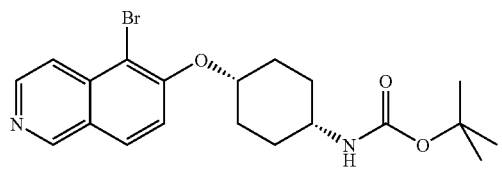 [SMILES: CC(C)(C)OC(=O)N[C@H]1CC[C@@H](Oc2ccc3cnccc3c2Br)CC1] | | [4-(5-Chloro-isoquinolin-6-yloxy)-cyclohexyl]-isopropyl-amine | 0.83/0.93 | 1 | 319.3/321.3 | cis-[4-(5-Bromo-isoquinolin-6-yloxy)-cyclohexyl]-carbamic acid tert-butyl ester (85)

4.33 mL (5.75 g, 33 mmol) of diethyl azo dicarboxylate were added to 18 g (68.75 mmol) of triphenylphosphine in 500 mL of dichloromethane at 0° C. and stirred for 15 min. 6.16 g (27.5 mmol) 5-bromo-isoquinolin-6-ol (2), 5.92 g (27.5 mmol) (trans-4-hydroxy-cyclohexyl)-carbamic acid tert-butyl ester and 3.81 mL (33 mmol) triethyl amine were added. The mixture was stirred for 4 days. The precipitate was removed by filtration, washed with dichloromethane and the solvents were distilled off. The crude product was purified by flash chromatography using ethyl acetate/n-heptane as eluent to give 2.77 g (24%) of 85. $R_t$=1.37 min (Method #1). Detected mass: 421.1/423.1 (M+H+).

General procedure for Suzuki-coupling with cis-[4-(5-bromo-isoquinolin-6-yloxy)-cyclohexyl]-carbamic acid tert-butyl ester (85)

2M Aqueous Na$_2$CO$_3$ solution (0.2 ml, 0.4 mmol, 2 eq.) was added to a solution of 81 mg (0.2 mmol, 1 eq.) of cis-[4-(5-bromo-isoquinolin-6-yloxy)-cyclohexyl]-carbamic acid tert-butyl ester (85) and 1.5 eq. (0.3 mmol) of the corresponding boronic acid in 3 mL of DME. Argon was bubbled through the reaction mixture for 10 min. Then, 23 mg (0.1 eq.) Pd(PPh$_3$)$_4$ were added and the reaction was stirred at 95° C. overnight under argon atmosphere. After cooling 2 mL of water and 10 mL of ethyl acetate were added. The organic layer was separated, dried and the solvent was distilled off. The remainder was subjected to preparative HPLC.

The Boc group was removed by dissolving the intermediate in isopropanol and addition of 5-6 N HCl in isopropanol. The precipitate was isolated by filtration.

In some reactions no hydrochloride precipitated or the purity of the precipitate was unsatisfactory. In these cases the solvent was distilled off and the remainder was purified by preparative HPLC.

The following examples were synthesized using this method (Table 6):

TABLE 6

| Example # | Product | Chemical Name | Boronic acid | LCMS Method # | retention time | detected mass [M + H]+ |
|---|---|---|---|---|---|---|
| 86 | | cis-4-(5-Ethyl-isoquinolin-6-yloxy)-cyclohexylamine | | 1 | 0.80 | 271.28 |
| 87 | | cis-4-(5-Thiophen-3-yl-isoquinolin-6-yloxy)-cyclohexylamine | | 1 | 0.87 | 325.20 |

TABLE 6-continued

| Example # | Product | Chemical Name | Boronic acid | LCMS Method # | retention time | detected mass [M + H]+ |
|---|---|---|---|---|---|---|
| 88 | | cis-4-(5-Methyl-isoquinolin-6-yloxy)-cyclohexylamine HCl | B(OH)$_2$ (methyl) | 1 | 0.80 | 257.24 |

General procedure for Coupling with cis-[4-(5-bromo-isoquinolin-6-yloxy)-cyclohexyl]-carbamic acid tert-butyl ester (85)

Under argon atmosphere 1.2 eq. of the stannane and 0.1 eq. of Pd(PPh$_3$)$_4$ were added to a solution of with cis-[4-(5-bromo-isoquinolin-6-yloxy)-cyclohexyl]-carbamic acid tert-butyl ester (85) in 4 ml of toluene. The reaction was heated to 100° C. in a microwave reactor (CEM Discovery) for 1 h.

After cooling to room temperature water and ethyl acetate were added. The mixture was filtered through a Celite cartridge, washed with ethyl acetate and concentrated. The crude Boc protected product was purified by preparative HPLC.

The Boc group was removed by dissolving the intermediate in isopropanol and addition of 5-6 N HCl in isopropanol. The precipitate was isolated by filtration.

The following examples were synthesized using this method (Table 7):

TABLE 7

| Example # | Product | Chemical Name | Stannane | LCMS Method # | retention time | detected mass [M + H]+ |
|---|---|---|---|---|---|---|
| 89 | | cis-4-(5-Pyridin-3-yl-isoquinolin-6-yloxy)-cyclohexylamine HCl | | 1 | 0.62 | 320.22 |
| 90 | | cis-4-(5-Vinyl-isoquinolin-6-yloxy)-cyclohexylamine HCl | | 1 | 0.76 | 269.20 |
| 91 | | cis-4-(5-Thiophen-2-yl-isoquinolin-6-yloxy)-cyclohexylamine HCl | | 2 | 0.83 | 325.15 |

TABLE 7-continued

| Example # | Product | Chemical Name | Stannane | LCMS Method # | retention time | detected mass [M + H]+ |
|---|---|---|---|---|---|---|
| 92 | | cis-4-(5-Phenyl-isoquinolin-6-yloxy)-cyclohexylamine | | 1 | 0.87 | 319.17 |
| 93 | | cis-4-(5-Pyridin-2-yl-isoquinolin-6-yloxy)-cyclohexylamine | | 2 | 0.51 | 320.22 |
| 94 | | cis-4-(5-Pyridin-4-yl-isoquinolin-6-yloxy)-cyclohexylamine | | 1 | 0.67 | 320.22 |

5,7-Dichloro-6-fluoro-isoquinoline (95)

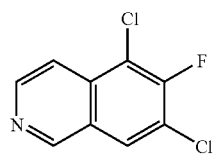 [SMILES: Fc1c(Cl)cc2cnccc2c1Cl]

5 g (23.1 mmol) 7-Chloro-6-fluoro-isoquinoline (6) were dissolved in 90 ml conc. sulfuric acid. At room temperature 7.34 g (55 mmol) N-chlorosuccinimide were added. The solution was heated to 50° C. and another 3.67 g (27.5 mmol) N-chlorosuccinimide were added. After standing overnight at room temperature, the reaction was again heated to 50° C. and another 18.35 g (137.5 mmol) N-chlorosuccinimide were added during the next 8 h. For working up, the reaction mixture was poured on ice. The aqueous solution was adjusted to alkaline pH with sodium hydroxide. The precipitate was filtered off and extracted three times with dichloromethane. The dichloromethane phases were dried with magnesium sulfate and evaporated to yield 1.09 g of the title compound, which was used without further purification.

trans-4-(5,7-Dichloro-isoquinolin-6-yloxy)-cyclohexylamine (96)

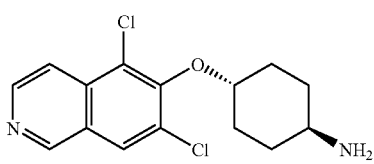 [SMILES: N[C@H]1CC[C@H](Oc2c(Cl)cc3cnccc3c2Cl)CC1]

Starting with 5,7-dichloro-6-fluoro-isoquinoline (95) and trans-(4-hydroxy-cyclohexyl)-carbamic acid tert-butyl ester, the title compound was synthesized following the protocol described for trans-[4-(5-chloro-isoquinolin-6-yloxy)-cyclohexyl]-carbamic acid tert-butyl ester (10). Purification of the obtained Boc-protected crude product by preparative HPLC, followed by treatment with trifluoroacetic acid gave the title compound as trifluoroacetate, which was dissolved in 2 M HCl. Evaporation of the solvent gave the desired product as HCl-salt. $R_t$=0.94 min (Method #1). Detected mass: 311.2/313.2 (M+H$^+$).

cis-[4-(7-Chloro-isoquinolin-6-yloxy)-cyclohexyl]-carbamic acid tert-butyl ester (97)

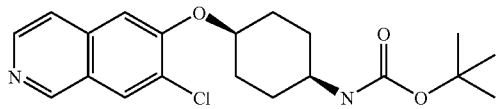 [SMILES: CC(C)(C)OC(=O)N[C@H]1CC[C@@H](Oc2cc3ccncc3cc2Cl)CC1]

Starting with 7-chloro-6-fluoro-isoquinoline (6) and cis-(4-hydroxy-cyclohexyl)-carbamic acid tert-butyl ester, the title compound was prepared by the protocol described for trans-[4-(5-chloro-isoquinolin-6-yloxy)-cyclohexyl]-carbamic acid tert-butyl ester (10). $R_t$=1.07 min (Method #4). Detected mass: 377.2/379.2 (M+H$^+$).

cis-4-(7-Chloro-isoquinolin-6-yloxy)-cyclohexylamine (98)

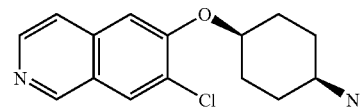 [SMILES: N[C@H]1CC[C@@H](Oc2cc3ccncc3cc2Cl)CC1]

cis-[4-(7-Chloro-isoquinolin-6-yloxy)-cyclohexyl]-carbamic acid tert-butyl ester (97) was deprotected following the method described for trans-4-(7-chloro-isoquinolin-6-yloxy)-cyclohexylamine (11) in methanol/2N HCl (1:1). After complete conversion, the solution was brought to alkaline pH by adding sodium hydroxide. The aqueous solution was extracted three times with dichloromethane. The combined organic layers were dried over MgSO$_4$ and evaporated. The crude product was purified by silicagel chromatography (CH$_2$Cl$_2$/MeOH 1:1→MeOH, 1% NH$_3$) followed by preparative HPLC, after which the desired product was isolated as trifluoroacetate. $R_t$=0.69 min (Method #1): Detected mass: 277.1 (M+H$^+$).

(2,2-Dimethoxy-ethyl)-(3,4,5-trifluoro-benzyl)-amine (99)

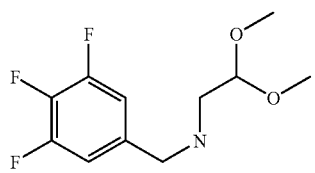 [SMILES: COC(CNCc1cc(F)c(F)c(F)c1)OC]

Starting from 3,4,5-trifluorobenzaldehyde, the title compound was prepared following the method described for 2,2-dimethoxy-ethyl)-(4-fluoro-benzyl)-amine (3). $R_t$=0.79 min (Method #4). Detected mass: 250.1 (M+H$^+$).

N-(2,2-Dimethoxy-ethyl)-4-methyl-N-(3,4,5-trifluoro-benzyl)-benzene-sulfonamide (100)

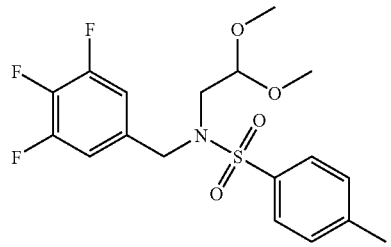 [SMILES: COC(CN(Cc1cc(F)c(F)c(F)c1)S(=O)(=O)c1ccc(C)cc1)OC]

Starting from (2,2-Dimethoxy-ethyl)-(3,4,5-trifluoro-benzyl)-amine (99), the title compound was prepared following the method described for N-(2,2-dimethoxy-ethyl)-N-(4-fluoro-benzyl)-4-methyl-benzene-sulfonamide (4). $R_t$=1.76 min (Method #4). Detected mass: 372.1 (M+H$^+$).

5,6,7-Trifluoro-isoquinoline (101)

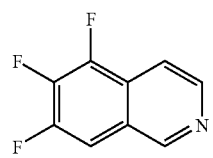

Cyclisation of N-(2,2-dimethoxy-ethyl)-4-methyl-N-(3,4,5-trifluoro-benzyl)-benzene-sulfonamide (100) by the method described for 6-fluoro-isoquinoline (5) gave the desired isoquinoline, which was isolated as trifluoro acetate after final purification by prep. HPLC. $R_t$=1.15 min (Method #1). Detected mass: 184.0 (M+H$^+$).

cis-4-(5,7-Difluoro-isoquinolin-6-yloxy)-cyclohexylamine (102)

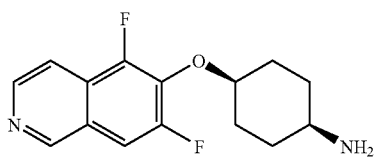 [SMILES: N[C@H]1CC[C@@H](Oc2c(F)cc3cnccc3c2F)CC1]

Starting from 5,6,7-trifluoro-isoquinoline (101) and cis-(4-hydroxy-cyclohexyl)-carbamic acid tert-butyl ester, the Boc-protected intermediate was prepared by the method described for trans-[4-(5-chloro-isoquinolin-6-yloxy)-cyclohexyl]-carbamic acid tert-butyl ester (10). Deprotection using standard procedures (see 11 or 13) gave the title compound, which was isolated as trifluoro acetate after prep. HPLC. Subsequent treatment of the obtained trifluoro acetate with 2N HCl, followed by lyophilisation gave the corresponding HCl-salt. $R_t$=0.86 min (Method #1). Detected mass: 279.1 (M+H$^+$).

General Procedure for the Reductive Amination Reaction:

0.25 mmol of the amine building block (hydrochloride) was weighted into the reaction tube. 3 ml trimethyl orthoformiate was added, then 0.25 mmol of the carbonyl compound (in 0.2 ml THF or solid), followed by 1.5 mmol (2.5 mmol in case of dihydrochlorides) Et$_3$N. The mixture was stirred for 1 h at room temperature, then cooled to −10° C. 1.5 ml of a freshly prepared solution of NaHB(OAc)$_3$ (1.25 mmol) in DMF was added, followed by 1.225 mmol acetic acid. The mixture was stirred for 30 min in the cold, then allowed to reach room temperature. Stirring was continued over night at room temperature. 0.5 ml water was added and the solvents were evaporated. The residue was dissolved in DMF, filtered over syringe filters, and purified by prep. HPLC. The purified products were dissolved in 1 ml HCl in isopropanol (5-6M), left at room temperature overnight, diluted with 2 ml water and freeze-dried to yield the hydrochlorides. In some cases, the obtained products had to be purified a second time by prep. HPLC. In these cases, the final products were isolated as trifluoroacetates (Table 8).

TABLE 8

| Example | Carbonyl-compound | Amine building block | Product | Chemical Name | [M + H⁺]/ [g/mol] | R<sub>t</sub>/ [min] | LCMS Met. |
|---|---|---|---|---|---|---|---|
| 103 | propanal | cis-4-(7-chloro-isoquinolin-6-yloxy)-cyclohexylamine | | cis-[4-(7-Chloro-isoquinolin-6-yloxy)-cyclohexyl]-propyl-amine | 319.1 | 0.82 | 1 |
| 104 | butanal | cis-4-(7-chloro-isoquinolin-6-yloxy)-cyclohexylamine | | cis-Butyl-[4-(7-chloro-isoquinolin-6-yloxy)-cyclohexyl]-amine | 333.2 | 0.96 | 1 |
| 105 | acetone | cis-4-(7-chloro-isoquinolin-6-yloxy)-cyclohexylamine | | cis-[4-(7-Chloro-isoquinolin-6-yloxy)-cyclohexyl]-isopropyl-amine | 319.1 | 0.92 | 1 |
| 106 | 3-pentanone | cis-4-(7-chloro-isoquinolin-6-yloxy)-cyclohexylamine | | cis-[4-(7-Chloro-isoquinolin-6-yloxy)-cyclohexyl]-(1-ethyl-propyl)-amine | 347.2 | 0.88 | 2 |
| 107 | isobutyraldehyde | cis-4-(7-chloro-isoquinolin-6-yloxy)-cyclohexylamine | | cis-[4-(7-Chloro-isoquinolin-6-yloxy)-cyclohexyl]-isobutyl-amine | 333.1 | 0.87 | 1 |
| 108 | cyclopropanecarbaldehyde | cis-4-(7-chloro-isoquinolin-6-yloxy)-cyclohexylamine | | cis-[4-(7-Chloro-isoquinolin-6-yloxy)-cyclohexyl]-cyclopropylmethyl-amine | 331.1 | 0.93 | 1 |

TABLE 8-continued

| Example | Carbonyl-compound | Amine building block | Product | Chemical Name | [M+H⁺]/ [g/mol] | $R_t$/ [min] | LCMS Met. |
|---|---|---|---|---|---|---|---|
| 109 | 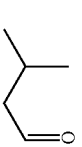 | 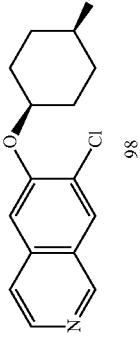 | 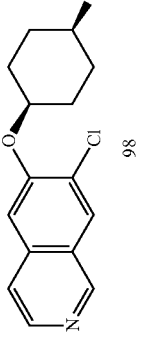 | cis-[4-(7-Chloro-isoquinolin-6-yloxy)-cyclohexyl]-(3-methyl-butyl)-amine | 347.2 | 1.04 | 1 |
| 110 | 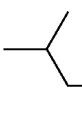 | 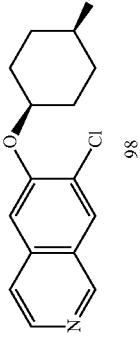 | 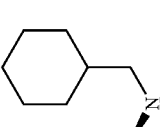 | cis-[4-(7-Chloro-isoquinolin-6-yloxy)-cyclohexyl]-cyclohexylmethyl-amine | 373.2 | 1.06 | 1 |
| 111 | 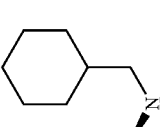 | 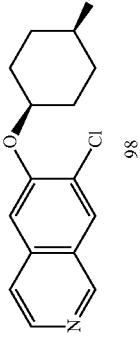 | 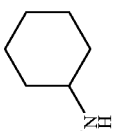 | cis-[4-(7-Chloro-isoquinolin-6-yloxy)-cyclohexyl]-cyclohexyl-amine | 359.2 | 1.02 | 1 |
| 112 | 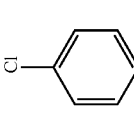 | 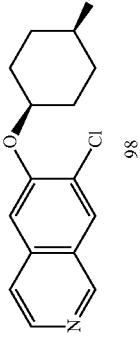 | 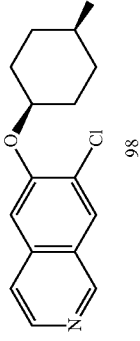 | cis-(4-Chloro-benzyl)-[4-(7-chloro-isoquinolin-6-yloxy)-cyclohexyl]-amine | 401.1 | 1.05 | 1 |

TABLE 8-continued

| Example | Carbonyl-compound | Amine building block | Product | Chemical Name | [M+H⁺]/ [g/mol] | R_f [min] | LCMS Met. |
|---|---|---|---|---|---|---|---|
| 113 | 3-chlorobenzaldehyde | 7-chloroisoquinolin-6-yloxy cyclohexylamine (98) | cis product structure | cis-(3-Chlorobenzyl)-[4-(7-chloro-isoquinolin-6-yloxy)-cyclohexyl]-amine | 401.1 | 1.13 | 1 |
| 114 | 2,4-dichlorobenzaldehyde | 7-chloroisoquinolin-6-yloxy cyclohexylamine (98) | cis product structure | cis-[4-(7-Chloro-isoquinolin-6-yloxy)-cyclohexyl]-(2,4-dichloro-benzyl)-amine | 435.1 | 1.14 | 2 |
| 115 | 4-(trifluoromethyl)benzaldehyde | 7-chloroisoquinolin-6-yloxy cyclohexylamine (98) | cis product structure | cis-[4-(7-Chloro-isoquinolin-6-yloxy)-cyclohexyl]-4-(4-trifluoromethyl-benzyl)-amine | 435.1 | 1.10 | 2 |
| 116 | isonicotinaldehyde | 7-chloroisoquinolin-6-yloxy cyclohexylamine (98) | cis product structure | cis-[4-(7-Chloro-isoquinolin-6-yloxy)-cyclohexyl]-pyridin-4-ylmethyl-amine | 368.0 | 0.84 | 1 |

TABLE 8-continued

| Example | Carbonyl-compound | Amine building block | Product | Chemical Name | [M+H+]/ [g/mol] | Rt/ [min] | LCMS Met. |
|---|---|---|---|---|---|---|---|
| 117 | acetaldehyde | 98 | | cis-[4-(7-Chloro-isoquinolin-6-yloxy)-cyclohexyl]-ethyl-amine | 305.2 | 0.77 | 1 |
| 118 | propanal | 11 | | trans-[4-(7-Chloro-isoquinolin-6-yloxy)-cyclohexyl]-propyl-amine | 319.2 | 0.90 | 1 |
| 119 | butanal | 11 | | trans-Butyl[4-(7-chloro-isoquinolin-6-yloxy)-cyclohexyl]-amine | 333.2 | 0.95 | 1 |
| 120 | acetone | 11 | | trans-[4-(7-Chloro-isoquinolin-6-yloxy)-cyclohexyl]-isopropyl-amine | 319.2 | 0.96 | 1 |
| 121 | 3-methylbutanal | 11 | | trans-[4-(7-Chloro-isoquinolin-6-yloxy)-cyclohexyl]-(3-methyl-butyl)-amine | 347.2 | 1.09 | 1 |

TABLE 8-continued

| Example | Carbonyl-compound | Amine building block | Product | Chemical Name | [M+H⁺]/ [g/mol] | R$_t$/ [min] | LCMS Met. |
|---|---|---|---|---|---|---|---|
| 122 | cyclohexanecarbaldehyde | 11 | (structure) ClH | trans-[4-(7-Chloro-isoquinolin-6-yloxy)-cyclohexyl]-cyclohexylmethyl-amine | 373.2 | 1.12 | 1 |
| 123 | benzaldehyde | 11 | (structure) ClH | trans-Benzyl-[4-(7-chloro-isoquinolin-6-yloxy)-cyclohexyl]-amine | 367.2 | 1.07 | 1 |
| 124 | 4-methylbenzaldehyde | 11 | (structure) ClH | trans-[4-(7-Chloro-isoquinolin-6-yloxy)-cyclohexyl]-(4-methyl-benzyl)-amine | 381.2 | 1.13 | 1 |
| 125 | pyridine-3-carbaldehyde | 11 | (structure) ClH | trans-[4-(7-Chloro-isoquinolin-6-yloxy)-cyclohexyl]-pyridin-3-ylmethyl-amine | 368.2 | 0.78 | 1 |

TABLE 8-continued

| Example | Carbonyl-compound | Amine building block | Product | Chemical Name | [M+H⁺]/ [g/mol] | R<sub>t</sub>/ [min] | LCMS Met. |
|---|---|---|---|---|---|---|---|
| 126 | 4-methylsulfonyl-benzaldehyde | 11 | (structure) ClH | trans-[4-(7-Chloro-isoquinolin-6-yloxy)-cyclohexyl]-pyridin-3-ylmethyl-(4-methanesulfonyl-benzyl)-amine | 445.2 | 1.00 | 1 |
| 127 | naphthalene-1-carbaldehyde | 11 | (structure) ClH | trans-[4-(7-Chloro-isoquinolin-6-yloxy)-cyclohexyl]-naphthalen-1-ylmethyl-amine | 417.2 | 1.20 | 1 |
| 128 | tetrahydrofuran-3-carbaldehyde | 11 | (structure) ClH | trans-[4-(7-Chloro-isoquinolin-6-yloxy)-cyclohexyl]-(tetrahydro-furan-3-ylmethyl)-amine | 361.2 | 0.87 | 1 |
| 129 | cyclohexanone | 11 | (structure) ClH | trans-[4-(7-Chloro-isoquinolin-6-yloxy)-cyclohexyl]-cyclohexyl-amine | 359.2 | 1.05 | 1 |

TABLE 8-continued

| Example | Carbonyl-compound | Amine building block | Product | Chemical Name | [M+H⁺]/ [g/mol] | R_t/ [min] | LCMS Met. |
|---|---|---|---|---|---|---|---|
| 130 | cyclopropanecarbaldehyde | 11 | (structure) ClH | trans-[4-(7-Chloro-isoquinolin-6-yloxy)-cyclohexyl]-cyclopropylmethyl-amine | 331.2 | 0.92 | 1 |
| 131 | isobutyraldehyde | 11 | (structure) ClH | trans-[4-(7-Chloro-isoquinolin-6-yloxy)-cyclohexyl]-isobutyl-amine | 333.2 | 0.99 | 1 |
| 132 | 4-chlorobenzaldehyde | 11 | (structure) TFA | trans-(4-Chloro-benzyl)-[4-(7-chloro-isoquinolin-6-yloxy)-cyclohexyl]-amine | 401.2 | 1.12 | 1 |
| 133 | 3-chlorobenzaldehyde | 11 | (structure) TFA | trans-(3-Chloro-benzyl)-[4-(7-chloro-isoquinolin-6-yloxy)-cyclohexyl]-amine | 401.1 | 1.15 | 1 |

TABLE 8-continued

| Example | Carbonyl-compound | Amine building block | Product | Chemical Name | [M+H⁺]/ [g/mol] | R_f/ [min] | LCMS Met. |
|---|---|---|---|---|---|---|---|
| 134 | 2,4-dichlorobenzaldehyde | 11 | (structure) | trans-[4-(7-Chloro-isoquinolin-6-yloxy)-cyclohexyl]-(2,4-dichloro-benzyl)-amine | 435.1 | 1.21 | 1 |
| 135 | 3,5-dichlorobenzaldehyde | 11 | (structure) | trans-[4-(7-Chloro-isoquinolin-6-yloxy)-cyclohexyl]-(3,5-dichloro-benzyl)-amine | 435.1 | 1.19 | 1 |
| 136 | 2-chlorobenzaldehyde | 11 | (structure) | trans-(2-Chloro-benzyl)-[4-(7-chloro-isoquinolin-6-yloxy)-cyclohexyl]-amine | 401.1 | 1.08 | 1 |

TABLE 8-continued

| Example | Carbonyl-compound | Amine building block | Product | Chemical Name | [M+H⁺]/ [g/mol] | $R_t$/ [min] | LCMS Met. |
|---|---|---|---|---|---|---|---|
| 137 | 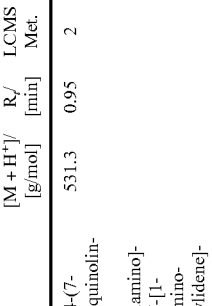 | 11 | 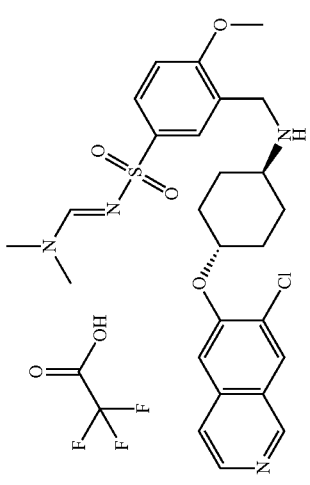 | trans-3-{[4-(7-Chloro-isoquinolin-6-yloxy)-cyclohexylamino]-methyl}-N-[1-dimethylamino-meth-(E)-ylidene]-4-methoxy-benzenesulfonamide | 531.3 | 0.95 | 2 |
| 138 | 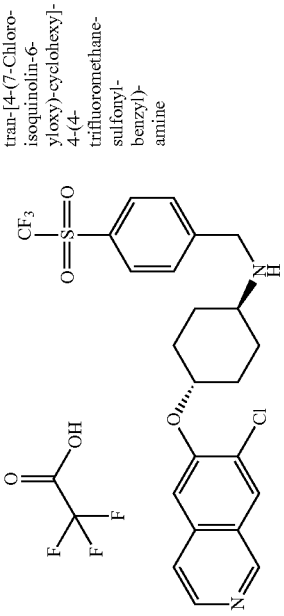 | 11 | 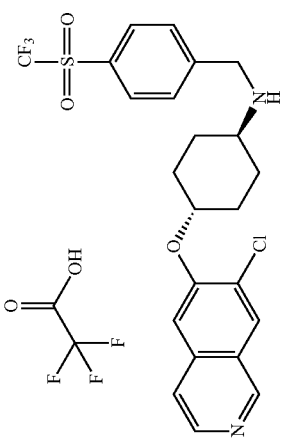 | tran-[4-(7-Chloro-isoquinolin-6-yloxy)-cyclohexyl]-4-(4-trifluoromethane-sulfonyl-benzyl)-amine | 499.2 | 1.22 | 2 |
| 139 | 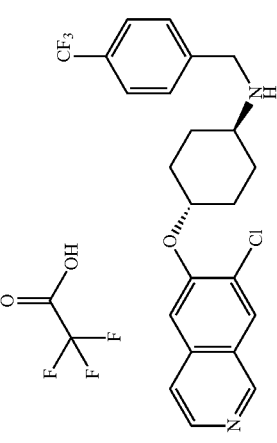 | 11 | 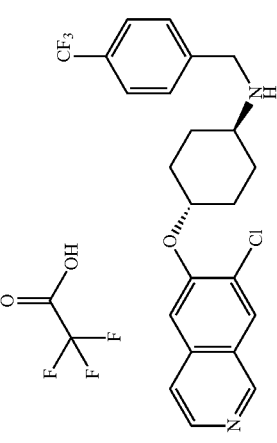 | trans-[4-(7-Chloro-isoquinolin-6-yloxy)-cyclohexyl]-4-(4-trifluoromethyl-benzyl)-amine | 435.2 | 1.19 | 2 |

Synthesis of Intermediate 144

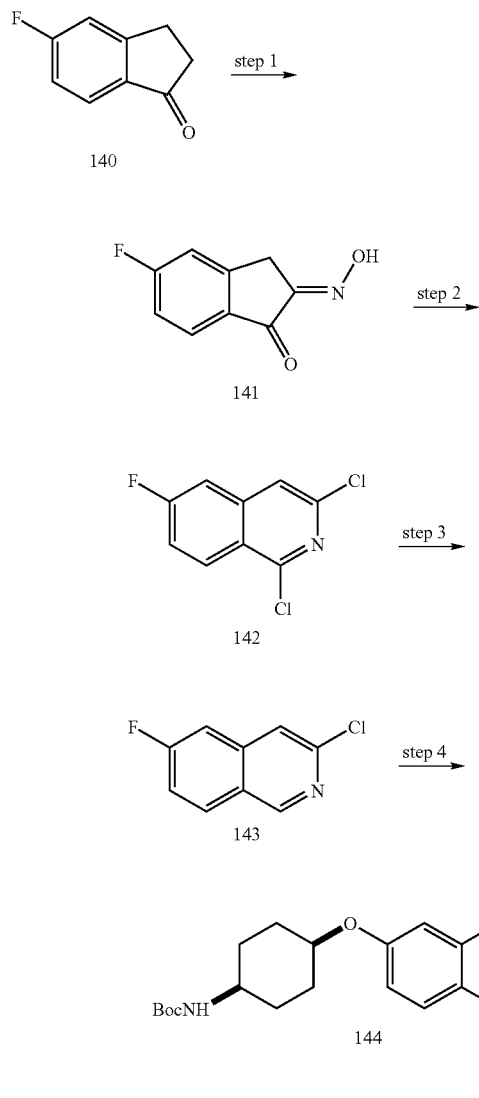

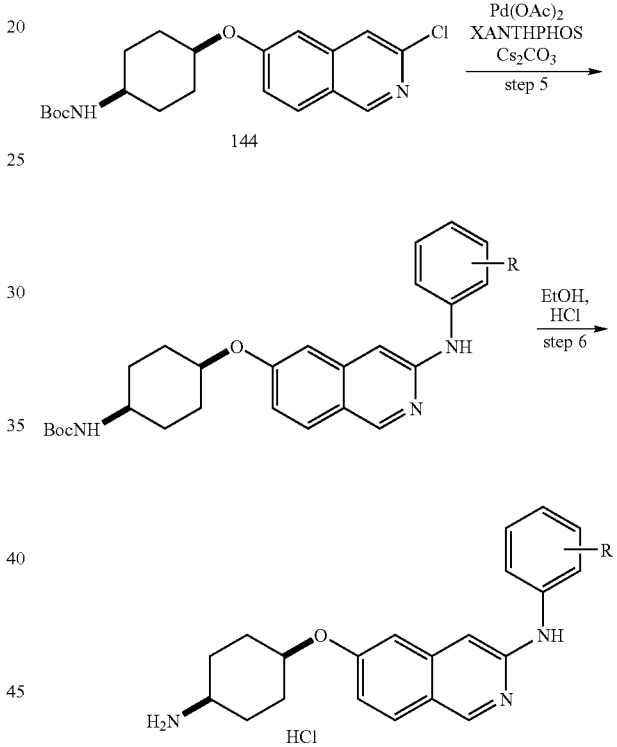

Step 1:

188 g of 5-Fluoro-indanone-1 (140) were dissolved in 1.8 l of diethyl ether, 50 ml of EtOH saturated with HCl were added at 0° C. and 1.1 l of a 15% ethyl nitrite solution in ether was added over 1 hour.

The solution was allowed to stir for an additional 3 hours to reach room temperature, then the solvent was removed partially and the precipitated product was collected by filtration.

Step 2

129 g of the product from Step 1 was added to a mixture of 170 g of $PCl_5$ in 2 l of $POCl_3$. Then gaseous HCl was added at 0° C. until saturation of the solution was reached. The remaining mixture was heated to 60° C. for 6 h, the solvent partially removed in vacuo and the residue was hydrolyzed on a crushed ice/water mixture. The precipitated product was isolated by filtration.

Step 3

155 g of crude product from Step 2 were added to a mixture of 740 ml HOAc and 330 ml HI (57%) containing 53 g of red phosphorous. After heating to reflux for 4 hours, the solution was treated with concentrated NaOH (until pH=8) and the precipitated product was isolated by filtration.

Step 4:

16.5 g of (cis-4-hydroxy-cyclohexyl)-carbamic acid tert-butyl ester were dissolved in 210 ml of diglyme and treated with 4.1 g 50% NaH under nitrogen. The resulting mixture was stirred for 1 h at room temperature, then 14.8 g of the product from Step 3 were added. The mixture was allowed to stir for 1 day at room temperature, then 100 ml of toluene were added and the resulting mixture was washed with water 3 times. The organic phases were collected and the solvent was removed in vacuo.

General Procedure for Derivatization of the 3-Position of 144

Step 5:

100 mg of compound 144 and 1.1 equivalents of the corresponding aniline were dissolved in 5 ml of dioxane, 350 mg of $Cs_2CO_3$, 20 mg of $Pd(OAc)_2$ and 60 mg of XANTHPHOS are added and the resulting mixture was heated to reflux under nitrogen until the starting material was consumed. (reaction was monitored by LCMS) The solvent was removed in vacuo and the residue was subjected to chromatography on a HPLC system.

Step 6:

The products of Step 5 are dissolved in 5 ml of ethanol saturated with gaseous HCl. After stirring for 5 h the desired product is isolated as its hydrochloride by removal of the solvent in vacuo.

The following examples were synthesized as hydrochlorides following this general procedure (Table 9):

TABLE 9

| No. | Compound | Chemical Name | RT [min] | Method # | Detected Mass [MH⁺] |
|---|---|---|---|---|---|
| 145 | 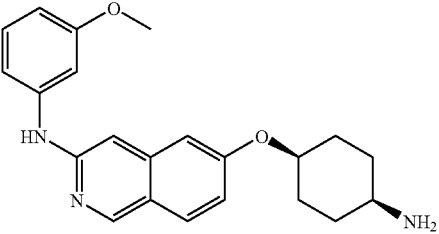 [SMILES: COc1cccc(Nc2cc3cc(O[C@H]4CC[C@@H](N)CC4)ccc3cn2)c1] | cis-[6-(4-Amino-cyclohexyloxy)-isoquinolin-3-yl]-(3-methoxy-phenyl)-amine | 1.07 | 1 | 364.23 |
| 146 | 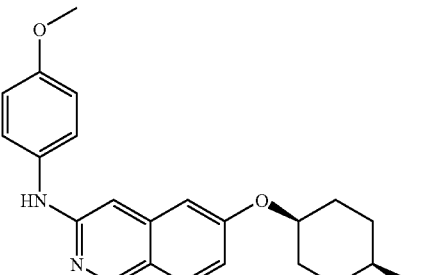 | cis-[6-(4-Amino-cyclohexyloxy)-isoquinolin-3-yl]-(4-methoxy-phenyl)-amine | 1.06 | 1 | 364.21 |
| 147 | 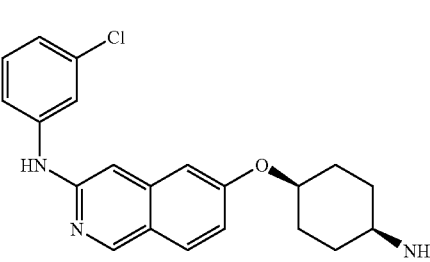 | cis-[6-(4-Amino-cyclohexyloxy)-isoquinolin-3-yl]-(3-chloro-phenyl)-amine | 1.15 | 1 | 368.15 |
| 148 | 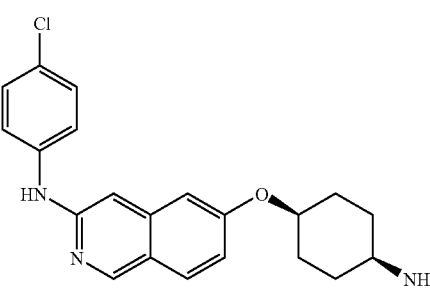 | cis-[6-(4-Amino-cyclohexyloxy)-isoquinolin-3-yl]-(4-chloro-phenyl)-amine | 1.16 | 1 | 368.15 |
| 149 | 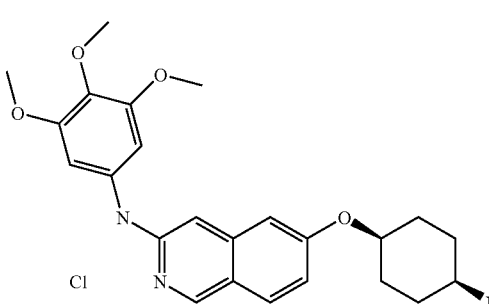 | cis-[6-(4-Amino-cyclohexyloxy)-isoquinolin-3-yl]-(3,4,5-trimethoxy-phenyl)-amine | 1.05 | 1 | 424.46 |

TABLE 9-continued

| No. | Compound | Chemical Name | RT [min] | Method # | Detected Mass [MH+] |
|---|---|---|---|---|---|
| 150 | 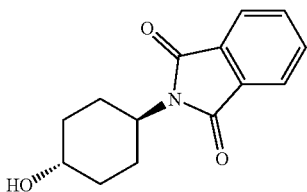 | cis-[6-(4-Amino-cyclohexyloxy)-isoquinolin-3-yl]-pyrazin-2-yl-amine | 0.95 | 1 | 336.12 | trans-2-(4-Hydroxy-cyclohexyl)-isoindole-1,3-dione (151)

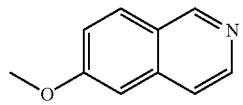

5 g of trans-4-cyclohexanolamine hydrochloride, 4.88 g of phthalic anhydride and 7.8 mL of tributyl amine were mixed and heated to 150° C. for 10 h. The mixture was cooled to room temperature, the solid was dissolved in dichloromethane and extracted with 1N HCl, evaporated to dryness and filtered over silica to yield 7.9 g of 151 as a colorless solid. $R_t$=1.28 min (Method #1). Detected mass: 228.0 (M–H$_2$O+H$^+$).

6-Methoxy-isoquinoline (152)

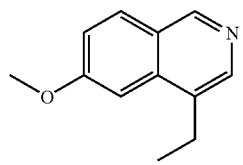

6-methoxy-isoquinoline (152) could be prepared by a similar reaction sequence as described for the synthesis of 6-fluoro-isoquinoline (5), starting from 4-methoxy benzaldehyde. $R_t$=0.65 min (Method #2). Detected mass: 160.1 (M+H$^+$).

4-Ethyl-6-methoxy-isoquinoline (153)

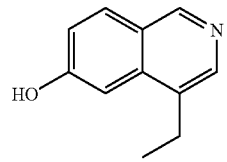

6 g of 6-Methoxy-isoquinoline (152) were dissolved in dry THF. Under argon a 1M solution of potassium triethylborane (37.7 mL) was added dropwise. The solution was stirred for five hours, then iodoethane (3.3 mL) was added dropwise. The solution was stirred overnight, cooled to 0° C. and 96 mL of 1N NaOH and 36 mL of 35% sodium peroxide were added. After gas evolution stopped, water and dichloromethane were added, the aqueous layer was extracted three times with dichloromethane the organic layer was dried over sodium sulfate and the solvent was removed in vacuo.

The residue was purified by silica gel chromatography to yield 1.96 g of product 153.

$R_t$=0.95 min (Method #1). Detected mass: 188.1 (M+H$^+$)

4-Ethyl-isoquinolin-6-ol (154)

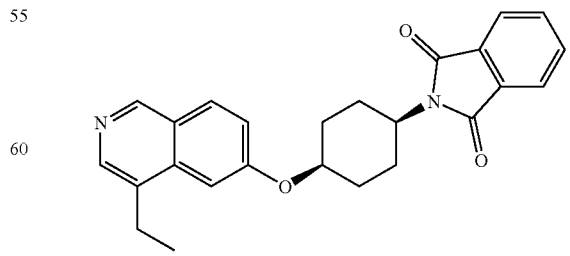

1.69 g of 4-Ethyl-6-methoxy-isoquinoline (153) were dissolved in dichloroethane and stirred with 1.7 mL of boron tribromide at room temperature for 3 hours and one additional hour at 40° C. The solution was poured on ice water, pH was adjusted to 9 by addition of sodium hydroxide and the solution was extracted with dichloromethane:isopropanol 3:1. The organic layer was evaporated to dryness and the product was purified by silica gel chromatography to yield 980 mg of 154. Detected Mess: 173.9 (M+H$^+$) (ESI)

2-[cis-4-(4-Ethyl-isoquinolin-6-yloxy)-cyclohexyl]-isoindole-1,3-dione (155)

157 mg of 4-Ethyl-isoquinolin-6-ol (154), 319 mg of trans-2-(4-Hydroxy-cyclohexyl)-isoindole-1,3-dione (151) and 923 mg of diphenyl-[4-[1H,1H,2H,2H-perfluorodecyl]phenyl]phosphine were suspended in 1 mL of THF. The solution was cooled to 0° C. and 1.1 g of Bis-(1H,2H,2H,3H,3H-perfluorononyl)-azodicarboxylate, dissolved in 1 mL of THF was added dropwise. The solution was warmed to room temperature and stirred overnight, filtered over a fluoroflash cartridge and the residue was purified by HPLC. Upon evaporation of the solvent, the product was isolated as the TFA salt. 180 mg with $R_t$=1.51 min (Method #1). Detected mass: 401.3 (M+H$^+$).

cis-4-(4-Ethyl-isoquinolin-6-yloxy)-cyclohexylamine (156)

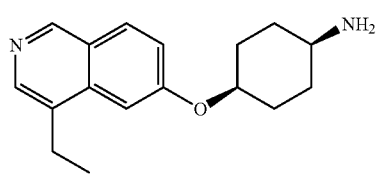 [SMILES: CCc1cncc2ccc(O[C@H]3CC[C@@H](N)CC3)cc12]

170 mg of 2-[cis-4-(4-Ethyl-isoquinolin-6-yloxy)-cyclohexyl]-isoindole-1,3-dione (155) were dissolved in 1 mL of methanol. 3.6 mL of 2M methylamine in methanol were added and the solution was stirred overnight. Another 0.5 mL of the methylamine solution was added and stirring was continued for another night.

The solution was evaporated, taken up in 1M HCl and extracted with ethyl acetate.

The aqueous layer was lyophilized and purified by HPLC, the resulting product was converted into its HCl salt by taking it up in 0.1M HCl and subsequent lyophilisation. The reaction yielded 71 mg of cis-4-(4-Ethyl-isoquinolin-6-yloxy)-cyclohexylamine as its hydrochloride (156). $R_t$=0.79 min (Method #1). Detected mass: 271.2 (M+H$^+$).

Determination of Rho Kinase Inhibition

To measure Rho-kinase inhibition, $IC_{50}$ values were determined according to the following protocol:

Buffer: 25 mM Tris pH7.5; 0.02% BSA; 5% Glycerol; 0.008% Triton X100; 2% DMSO, 1 mM DTT; 1 mM MgCl$_2$; 0.5 µCi/well γ$^{33}$P ATP Enzyme: ROCKII or ROKα) (Upstate, Catalog #14-451 Lot # 24880U) 0.1 ng/µl Final concentration of ATP in reaction mixture 40 µM Biotinylated substrate, diluted to 0.25 µM with buffer described above (without ATP)
1. 10 µl Tris buffer (±Inhibitor)
2. Add 30 µL of enzyme solution
3. Start the reaction with 30 µL of mix substrate/ATP/ATP33
4. Incubate for 20 min at room temperature
5. Stop reaction with 30 µL of 50 mM EDTA
6. Transfer 50 µL of stopped solution to Streptavidin Flash Plate plus, Perkin Elmer, SMP 103A
7. Incubate for 30 min at RT
8. Wash 4 times with 300 µl of PBS/0.1% Tween 20
9. Radioactivity in the well was determined

| No. | IC50 |
|---|---|
| 13 | +++++ |
| 14 | +++++ |
| 19 | +++++ |

-continued

| No. | IC50 |
|---|---|
| 23 | +++++ |
| 26 | +++++ |
| 38 | +++++ |
| 44 | ++++ |
| 45 | ++++ |
| 52 | ++++ |
| 54 | ++++ |
| 58 | ++++ |
| 64 | +++++ |
| 72 | +++++ |
| 74 | +++++ |
| 80 | +++++ |
| 87 | +++++ |
| 90 | +++++ |
| 96 | +++++ |
| 147 | ++++ |
| 149 | +++++ |
| 150 | ++++ |
| 156 | +++++ |

The given activity is denoted as the negative decadal logarithm of the $IC_{50}$ ($pIC_{50}$) as follows:

| | |
|---|---|
| +: | $pIC_{50} \leq 3.0$ |
| ++: | $3.0 \leq pIC_{50} < 4.0$ |
| +++ | $4.0 \leq pIC_{50} < 5.0$ |
| ++++: | $5.0 \leq pIC_{50} < 6.0$ |
| +++++ | $6.0 \leq pIC_{50}$ |

The invention claimed is:
1. A compound of the formula (I)

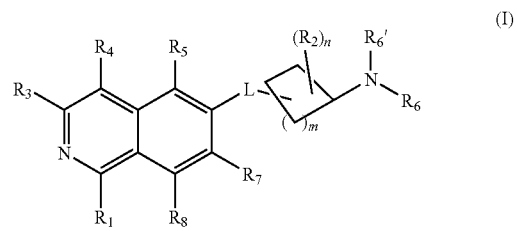

wherein
$R_1$ is
H,
N[(C$_1$-C$_6$)alkyl]$_2$;
$R_2$ is H, halogen or (C$_1$-C$_6$)alkyl;
$R_3$ is
H,
halogen,
(C$_1$-C$_6$)alkyl,
OH,
O—R",
NH$_2$,
NHR",
NR"R" or
NH—C(O)—R";
$R_4$ is
H,
halogen,
hydroxy,
CN,
(C$_1$-C$_6$)alkyl,
$R_5$ is H,
halogen,
CN,
NO$_2$,
(C$_1$-C$_6$)alkyl,
(C$_2$-C$_6$)alkenyl,
CH(OH)—(C$_1$-C$_6$)alkyl,
NH$_2$,
NH—SO$_2$H,
NH—SO$_2$—(C$_1$-C$_6$)alkyl,
NH—C(O)—(C$_1$-C$_6$)alkyl,
C(O)N[(C$_1$-C$_6$)alkyl]$_2$,
C(O)OH, or
C(O)O—(C$_1$-C$_6$)alkyl;
R$_6$ is H, (C$_1$-C$_6$)alkyl or (C$_1$-C$_6$)alkylene-(C$_3$-C$_8$)cycloalkyl;
R$_6$' is
H,
R',
(C$_1$-C$_8$)alkyl,
(C$_1$-C$_6$)alkylene-R',
(C$_1$-C$_6$)alkylene-O—(C$_1$-C$_6$)alkyl,
(C$_1$-C$_6$)alkylene-O—R',
(C$_1$-C$_6$)alkylene-CH[R']$_2$,
(C$_1$-C$_6$)alkylene-C(O)—R',
(C$_1$-C$_6$)alkylene-C(O)NH$_2$,
(C$_1$-C$_6$)alkylene-C(O)NH—R',
(C$_1$-C$_6$)alkylene-C(O)NH—(C$_1$-C$_6$)alkyl,
(C$_1$-C$_6$)alkylene-C(O)N[(C$_1$-C$_6$)alkyl]$_2$,
(C$_1$-C$_6$)alkylene-C(O)N[R']$_2$;
(C$_1$-C$_6$)alkylene-C(O)O—(C$_1$-C$_6$)alkyl,
C(O)O—(C$_1$-C$_6$)alkyl,
C(O)OR',
C(O)R',
C(O)NH—(C$_1$-C$_6$)alkyl,
C(O)NHR',
C(O)N[(C$_1$-C$_6$)alkyl]R'
C(O)N[(C$_1$-C$_6$)alkyl]$_2$,
C(O)—(C$_1$-C$_6$)alkylene-R',
C(O)O(C$_1$-C$_6$)alkylene-R', or
R$_6$ and R$_6$', together with the N-atom to which they are attached, form a (C$_5$-C$_{10}$) heterocyclyl group;
R$_7$ is
H,
halogen,
CN,
NO$_2$,
(C$_1$-C$_6$)alkyl,
O—(C$_1$-C$_6$)alkyl,
(C$_2$-C$_6$)alkenyl,
CH(OH)—(C$_1$-C$_6$)alkyl,
NH$_2$,
NH—SO$_2$H,
NH—SO$_2$—(C$_1$-C$_6$)alkyl,
SO$_2$—NH$_2$,
NH—C(O)—(C$_1$-C$_6$)alkyl,
C(O)N[(C$_1$-C$_6$)alkyl]$_2$,
C(O)OH, or
C(O)O—(C$_1$-C$_6$)alkyl;
R$_8$ is H, halogen or (C$_1$-C$_6$)alkyl;
n is 1, 2, 3 or 4;
m is 3; and
L is O or O—(C$_1$-C$_6$)alkylene;
R' is
(C$_3$-C$_8$)cycloalkyl,
(C$_5$-C$_{10}$)heterocyclyl,
(C$_6$-C$_{10}$)aryl; and
R" is
(C$_5$-C$_{10}$)heterocyclyl,
(C$_6$-C$_{10}$)aryl,
(C$_1$-C$_6$)alkyl,
(C$_1$-C$_6$)alkylene-O—(C$_1$-C$_6$)alkyl,
or
(C$_1$-C$_6$)alkylene-NR$_x$R$_y$; and
R$_x$ and R$_y$ are independently of each other
(C$_1$-C$_6$)alkyl,
(C$_1$-C$_4$)alkylene-NH(C$_1$-C$_6$)alkyl, or
(C$_1$-C$_4$)alkylene-N[(C$_1$-C$_6$)alkyl]$_2$,
wherein in residues R$_4$, R$_5$, R$_6$, R$_6$', R$_7$ and R$_8$ as alkyl, alkylene or cycloalkyl can optionally be substituted one or more times by OH, OCH$_3$, COOH, COOCH$_3$, NH$_2$, NHCH$_3$, N(CH$_3$)$_2$, CONH$_2$, CONHCH$_3$ or CON(CH$_3$)$_2$;
wherein in residues R$_1$ to R$_8$ as alkyl or alkylene can optionally be substituted one or more times by halogen;
wherein in residues R3, R6 and R6' as (C$_6$-C$_{10}$)aryl and (C$_5$-C$_{10}$)heterocyclyl are unsubstituted or substituted one or more times by a group independently selected from halogen, OH, NO$_2$, N$_3$, CN, C(O)—(C$_1$-C$_6$)alkyl, C(O)—(C$_6$-C$_{10}$)aryl, COOH, COO(C$_{1-6}$)alkyl, CONH$_2$, CONH(C$_1$-C$_6$)alkyl, CON[(C$_1$-C$_6$)alkyl]$_2$, (C$_3$-C$_8$)cycloalkyl, (C$_1$-C$_6$)alkyl, (C$_1$-C$_6$)alkylene-OH, (C$_1$-C$_6$)alkylene-NH$_2$, (C$_1$-C$_6$)alkylene-NH(C$_1$-C$_6$)alkyl, (C$_1$-C$_6$)alkylene-N[(C$_1$-C$_6$)alkyl]$_2$, (C$_2$-C$_6$)alkenyl, (C$_2$-C$_6$)alkynyl, O—(C$_1$-C$_6$)alkyl, O—C(O)—(C$_1$-C$_6$)alkyl, PO$_3$H$_2$, SO$_3$H, SO$_2$—NH$_2$, SO$_2$NH(C$_1$-C$_6$)alkyl, SO$_2$N[(C$_1$-C$_6$)alkyl]$_2$, S—(C$_1$-C$_6$)alkyl; SO—(C$_1$-C$_6$)alkyl, SO$_2$—(C$_1$-C$_6$)alkyl, SO$_2$—N=CH—N[(C$_1$-C$_6$)alkyl]$_2$, C(NH)(NH$_2$), NH$_2$, NH—(C$_1$-C$_6$)alkyl, N[(C$_1$-C$_6$)alkyl]$_2$, NH—C(O)—(C$_1$-C$_6$)alkyl, NH—C(O)O—(C$_1$-C$_6$)alkyl, NH—SO$_2$—(C$_1$-C$_6$)alkyl, NH—SO$_2$—(C$_6$-C$_{10}$)aryl, NH—SO$_2$—(C$_5$-C$_{10}$)heterocyclyl, N(C$_1$-C$_6$)alkyl-C(O)—(C$_1$-C$_6$)alkyl, N(C$_1$-C$_6$)alkyl-C(O)O—(C$_1$-C$_6$)alkyl, N(C$_1$-C$_6$)alkyl-C(O)—NH—(C$_1$-C$_6$)alkyl], (C$_6$-C$_{10}$)aryl, (C$_1$-C$_6$)alkylene-(C$_6$-C$_{10}$)aryl, O—(C$_6$-C$_{10}$)aryl, O—(C$_1$-C$_6$)alkylene-(C$_6$-C$_{10}$)aryl, (C$_5$-C$_{10}$)heterocyclyl, (C$_1$-C$_6$)alkylene-(C$_5$-C$_{10}$)heterocyclyl, and O—(C$_1$-C$_6$)alkylene-(C$_5$-C$_{10}$)heterocyclyl, wherein the (C$_6$-C$_{10}$)aryl or (C$_5$-C$_{10}$)heterocyclyl in the substituent may be substituted one to three times by a group independently selected from halogen, OH, NO$_2$, CN, O—(C$_1$-C$_6$)alkyl, (C$_1$-C$_6$)alkyl, NH$_2$, NH(C$_1$-C$_6$)alkyl, N[(C$_1$-C$_6$)alkyl]$_2$, SO$_2$CH$_3$, COOH, C(O)O—(C$_1$-C$_6$)alkyl; or wherein (C$_6$-C$_{10}$)aryl is vicinally substituted by a O—(C$_1$-C$_4$)alkylene-O group whereby a 5-8-membered ring is formed together with the carbon atoms the oxygen atoms are attached to; and wherein aryl substituent of (C$_6$-C$_{10}$)aryl and (C$_5$-C$_{10}$)heterocyclyl substituent groups may not be further substituted by an aryl or heterocyclyl containing group; or
pharmaceutically acceptable salt thereof;
with the proviso that the following compounds are excluded: cis-4-(isoquinolin-6-yloxy)-cyclohexylamine and trans-4-(isoquinolin-6-yloxy)-cyclohexylamine.

2. The compound according to claim 1, wherein R$_1$ is H, or N[(C$_1$-C$_6$)alkyl]$_2$.

3. The compound according to claim 2, wherein R$_1$ is H, or N[(C$_1$-C$_4$)alkyl]$_2$.

4. The compound according to claim 3, wherein R$_1$ is H.

5. The compound according to claim 1, wherein R$_3$ is H, halogen, O—R" or NHR".

6. The compound according to claim 5, wherein $R_3$ is H or NHR".

7. The compound according to claim 6, wherein $R_3$ is H; NH—$(C_5$-$C_6)$heterocyclyl, or NH-phenyl.

8. The compound according to claim 7, wherein $R_3$ is H.

9. The compound according to claim 1, wherein $R_8$ is H, halogen or $(C_1$-$C_4)$alkyl.

10. The compound according to claim 9, wherein $R_8$ is H, Cl, F, methyl or ethyl.

11. The compound according to claim 10, wherein $R_8$ is H.

12. The compound according to claim 1, wherein $R_4$ is H, halogen or $(C_1$-$C_6)$alkyl.

13. The compound according to claim 12, wherein $R_4$ is H, halogen or $(C_1$-$C_4)$alkyl.

14. The compound according to claim 13, wherein $R_4$ is H.

15. The compound according to claim 1, wherein $R_5$ is H, halogen, CN, $(C_1$-$C_6)$alkyl, or $(C_2$-$C_6)$alkenyl.

16. The compound according to claim 15, wherein $R_5$ is H, halogen, $(C_1$-$C_6)$alkyl, or $(C_2$-$C_6)$alkenyl.

17. The compound according to claim 16, wherein $R_5$ is H, halogen, methyl, ethyl, or vinyl.

18. The compound according to claim 17, wherein $R_5$ is H, halogen, methyl, or ethyl.

19. The compound according to claim 18, wherein $R_5$ is H.

20. The compound according to claim 1, wherein $R_7$ is H, halogen, CN, $(C_1$-$C_6)$alkyl, O—$(C_1$-$C_6)$alkyl or $(C_2$-$C_6)$alkenyl.

21. The compound according to claim 20, wherein $R_7$ is H, halogen, CN, $(C_1$-$C_4)$alkyl, O—$(C_1$-$C_4)$alkyl or $(C_2$-$C_4)$alkenyl.

22. The compound according to claim 21, wherein $R_7$ is H, fluoro, chloro, bromo, methyl, ethyl, methoxy, CN or vinyl.

23. The compound according to claim 22, wherein $R_7$ is H, fluoro, chloro, bromo, methyl or methoxy.

24. The compound according to claim 23, wherein $R_7$ is H.

25. The compound according to claim 1, wherein $R_2$ is H, halogen or $(C_1$-$C_4)$alkyl.

26. The compound according to claim 25, wherein $R_2$ is H, methyl or ethyl.

27. The compound according to claim 1, wherein n is 1, 2 or 3.

28. The compound according to claim 27, wherein n is 1 or 2.

29. The compound according to claim 28, wherein n is 1.

30. The compound according to claim 1, wherein $R_6$ is H, $(C_1$-$C_6)$alkyl or $(C_1$-$C_6)$alkylene-$(C_3$-$C_8)$cycloalkyl;
$R_6'$ is
H,
$(C_1$-$C_6)$alkyl,
R',
$(C_1$-$C_4)$alkylene-$(C_3$-$C_8)$cycloalkyl,
$(C_1$-$C_4)$alkylene-$(C_5$-$C_{10})$heterocyclyl,
$C_1$-$C_4)$alkylene-$(C_6$-$C_{10})$aryl,
$(C_1$-$C_6)$alkylene-O—$(C_1$-$C_6)$alkyl,
$(C_1$-$C_4)$alkylene-C(O)—$(C_5$-$C_{10})$heterocyclyl,
$(C_1$-$C_4)$alkylene-C(O)—$(C_6$-$C_{10})$aryl,
$(C_1$-$C_6)$alkylene-C(O)N[$(C_1$-$C_6)$alkyl]$_2$,
$(C_1$-$C_6)$alkylene-C(O)NH—$(C_1$-$C_6)$alkyl,
$(C_1$-$C_6)$alkylene-C(O)O—$(C_1$-$C_6)$alkyl,
C(O)O—$(C_1$-$C_6)$alkyl,
C(O)R'
C(O)NH—$(C_1$-$C_6)$alkyl,
C(O)N[$(C_1$-$C_6)$alkyl]$_2$, or
C(O)$(C_1$-$C_6)$alkylene-R',
or $R_6$ and $R_6'$, together with the N-atom to which they are attached, form a $(C_5$-$C_{10})$heterocyclyl group.

31. The compound according to claim 30, wherein
$R_6$ is H, $(C_1$-$C_6)$alkyl or $(C_1$-$C_6)$alkylene-$(C_3$-$C_8)$cycloalkyl;
$R_6'$ is
H,
$(C_1$-$C_6)$alkyl,
$(C_5$-$C_{10})$heterocyclyl,
$(C_3$-$C_8)$cycloalkyl,
$(C_6$-$C_{10})$aryl,
$(C_1$-$C_4)$alkylene-$(C_3$-$C_8)$cycloalkyl,
$(C_1$-$C_4)$alkylene-$(C_5$-$C_{10})$heterocyclyl,
$(C_1$-$C_4)$alkylene-$(C_6$-$C_{10})$aryl,
$(C_1$-$C_6)$alkylene-O—$(C_1$-$C_6)$alkyl,
$(C_1$-$C_6)$alkylene-C(O)N[$(C_1$-$C_6)$alkyl]$_2$,
$(C_1$-$C_6)$alkylene-C(O)NH—$(C_1$-$C_6)$alkyl,
$(C_1$-$C_6)$alkylene-C(O)O—$(C_1$-$C_6)$alkyl,
C(O)O—$(C_1$-$C_6)$alkyl,
C(O)$(C_3$-$C_8)$cycloalkyl,
C(O)NH—$(C_1$-$C_6)$alkyl,
C(O)N[$(C_1$-$C_6)$alkyl]$_2$,
C(O)$(C_1$-$C_6)$alkylene-$(C_3$-$C_8)$cycloalkyl,
C(O)$(C_1$-$C_6)$alkylene-$(C_5$-$C_{10})$heterocyclyl,
C(O)$(C_1$-$C_6)$alkylene-$(C_6$-$C_{10})$aryl,
or $R_6$ and $R_6'$, together with the N-atom to which they are attached form a $(C_5$-$C_{10})$heterocyclyl group.

32. The compound according to claim 31, wherein $R_6$ is H, $(C_1$-$C_6)$alkyl or $(C_1$-$C_4)$alkylene-$(C_3$-$C_6)$cycloalkyl, and $R_6'$ is H,
$(C_1$-$C_6)$alkyl,
$(C_3$-$C_8)$cycloalkyl,
$(C_5$-$C_{10})$heterocyclyl,
$(C_6$-$C_{10})$aryl,
$(C_1$-$C_4)$alkylene-$(C_3$-$C_8)$cycloalkyl,
$(C_1$-$C_4)$alkylene-$(C_5$-$C_{10})$heterocyclyl,
$(C_1$-$C_4)$alkylene-$(C_6$-$C_{10})$aryl,
$(C_1$-$C_6)$alkylene-O—$(C_1$-$C_6)$alkyl,
$(C_1$-$C_6)$alkylene-C(O)NH—$(C_1$-$C_6)$alkyl,
$(C_1$-$C_6)$alkylene-C(O)N[$(C_1$-$C_6)$alkyl]$_2$,
$(C_1$-$C_6)$alkylene-C(O)O—$(C_1$-$C_6)$alkyl,
C(O)O—$(C_1$-$C_6)$alkyl,
C(O)$(C_3$-$C_8)$cycloalkyl,
C(O)NH—$(C_1$-$C_6)$alkyl,
C(O)N[$(C_1$-$C_6)$alkyl]$_2$,
C(O)$(C_1$-$C_6)$alkylene-$(C_3$-$C_8)$cycloalkyl,
C(O)$(C_1$-$C_6)$alkylene-$(C_5$-$C_{10})$heterocyclyl,
C(O)$(C_1$-$C_6)$alkylene-$(C_6$-$C_{10})$aryl, or
$R_6$ and $R_6'$, together with the N-atom to which they are attached, form a $(C_5$-$C_{10})$heterocyclyl group.

33. The compound according to claim 32, wherein
$R_6$ is H or $(C_1$-$C_6)$alkyl and
$R_6'$ is H,
$(C_1$-$C_6)$alkyl,
$(C_3$-$C_8)$cycloalkyl,
$(C_6$-$C_{10})$aryl,
$(C_5$-$C_{10})$heterocyclyl,
$(C_1$-$C_4)$alkylene-$(C_3$-$C_8)$cycloalkyl,
$(C_1$-$C_4)$alkylene-$(C_5$-$C_{10})$heterocyclyl,
$(C_1$-$C_6)$alkylene-$(C_6$-$C_{10})$aryl,
$(C_1$-$C_4)$alkylene-O—$(C_1$-$C_4)$alkyl,
$(C_1$-$C_4)$alkylene-C(O)N[$(C_1$-$C_4)$alkyl]$_2$,
$(C_1$-$C_6)$alkylene-C(O)NH—$(C_1$-$C_6)$alkyl, or
$R_6$ and $R_6'$, together with the N-atom to which they are attached, form a $(C_5$-$C_{10})$heterocyclyl group.

34. The compound according to claim 33, wherein
$R_6$ is H, $(C_1$-$C_6)$alkyl and
$R_6'$ is H;
$(C_1$-$C_6)$alkyl;

($C_3$-$C_8$)cycloalkyl;

($C_1$-$C_4$)alkylene-($C_3$-$C_8$)cycloalkyl;

($C_1$-$C_4$)alkylene-O—($C_1$-$C_4$)alkyl;

($C_1$-$C_4$)alkylene-C(O)N[($C_1$-$C_4$)alkyl]$_2$;

($C_1$-$C_4$)alkylene-($C_5$-$C_{10}$)heterocyclyl wherein heterocyclyl is unsubstituted or substituted one or more times by a group indepedently selected from ($C_1$-$C_4$)alkyl, O—($C_1$-$C_4$)alkyl, halogen, and phenyl, or is substituted once by ($C_5$-$C_6$)heterocyclyl, wherein phenyl or ($C_5$-$C_6$) heterocyclyl in the substituent is unsubstituted or substituted one to three times by a group indepedently selected from halogen, ($C_1$-$C_4$)alkyl or O—($C_1$-$C_4$) alkyl; or ($C_1$-$C_4$)alkylene-($C_6$-$C_{10}$)aryl wherein aryl is unsubstituted or substituted one or more times by a group independently selected from halogen, ($C_1$-$C_4$)alkyl, O—($C_1$-$C_4$)alkyl, CN, SO$_2$—NH$_2$, SO$_2$—($C_1$-$C_4$)alkyl, SO$_2$—N=CH—N[($C_1$-$C_4$)alkyl]$_2$, NH—O—($C_1$-$C_4$) alkyl, and CO—O—($C_1$-$C_4$)alkyl, or is substituted once by unsubstituted phenyl, unsubstituted O-phenyl or unsubstituted ($C_5$-$C_6$)heterocyclyl;

or $R_6$ and $R_6'$, together with the N-atom to which they are attached, form a ($C_5$-$C_6$)heterocyclyl group, which is unsubstituted or substituted one to three times by ($C_1$-$C_4$)alkyl or C(O)O($C_1$-$C_4$)alkyl;

wherein a ($C_1$-$C_4$)alkyl or ($C_1$-$C_6$)alkyl residue is unsubstituted or substituted one to three times by halogen.

35. The compound according to claim 34, wherein $R_6$ is H or ($C_1$-$C_6$)alkyl, and $R_6'$ is H, ($C_1$-$C_6$)alkyl or ($C_3$-$C_8$)cycloalkyl.

36. The compound according to claim 35, wherein $R_6$ is H, and $R_6'$ is H, unsubstituted ($C_1$-$C_6$)alkyl or unsubstituted ($C_3$-$C_8$)cycloalkyl.

37. The compound according to claim 36, wherein $R_6$ and $R_6'$ are H.

38. The compound according to claim 1, wherein m is 3 and L is attached to the 3-position or to the 4-position of the amino cyclohexane ring.

39. The compound according to claim 1, wherein m is 3 and L is attached to the 4-position of the amino cyclohexane ring.

40. The compound according to claim 1, wherein L is O-methylene, O-ethylene or O.

41. The compound according to claim 40, wherein L is O.

42. The compound according to claim 1, wherein $R_1$ is H, or N[($C_1$-$C_6$)alkyl]$_2$;

$R_3$ is H, halogen, O—R" or NHR";

$R_4$ is H, halogen or ($C_1$-$C_6$)alkyl;

$R_5$ is H, ($C_1$-$C_6$)alkyl, halogen, CN, or ($C_2$-$C_6$)alkenyl;

$R_6$ is H, ($C_1$-$C_6$)alkyl or ($C_1$-$C_6$)alkylene-($C_3$-$C_8$)cycloalkyl;

$R_6'$ is H, R', ($C_1$-$C_8$)alkyl, ($C_1$-$C_6$)alkylene-R', ($C_1$-$C_6$) alkylene-O—($C_1$-$C_6$)alkyl, ($C_1$-$C_6$)alkylene-O—R', ($C_1$-$C_6$)alkylene-CH[R']$_2$, ($C_1$-$C_6$)alkylene-C(O)NH$_2$, ($C_1$-$C_6$)alkylene-C(O)NH—R', ($C_1$-$C_6$)alkylene-C(O) N[($C_1$-$C_4$)alkyl]$_2$, ($C_1$-$C_6$)alkylene-C(O)N[R]$_2$, C(O) O—($C_1$-$C_6$)alkyl, C(O)($C_3$-$C_8$)cycloalkyl, C(O)($C_5$-$C_{10}$)heterocyclyl, C(O)NH—($C_1$-$C_6$)alkyl, C(O)N[($C_1$-$C_6$)alkyl]$_2$, C(O)($C_1$-$C_6$)alkylene-($C_3$-$C_8$)cycloalkyl, C(O)($C_1$-$C_6$)alkylene-($C_5$-$C_{10}$)heterocyclyl, C(O)($C_1$-$C_6$)alkylene-($C_6$-$C_{10}$)aryl, or $R_6$ and $R_6'$, together with the N-atom to which they are attached, form a ($C_5$-$C_6$)heterocyclyl group;

$R_7$ is H, halogen, CN, ($C_1$-$C_6$)alkyl, O—($C_1$-$C_6$)alkyl or ($C_2$-$C_6$)alkenyl;

m is 3 n is 1, 2 or 3, and

L is O, O-methylene or O-ethylene.

43. The compound according to claim 1, wherein $R_1$ is H, or N[($C_1$-$C_6$)alkyl]$_2$;

$R_2$ is H or ($C_1$-$C_4$)alkyl;

$R_3$ is H, halogen or NHR";

$R_4$ is H, halogen or ($C_1$-$C_4$)alkyl;

$R_5$ is H, ($C_1$-$C_6$)alkyl, halogen, or ($C_2$-$C_4$)alkenyl;

$R_6$ is H, ($C_1$-$C_6$)alkyl or ($C_1$-$C_6$)alkylene-($C_3$-$C_8$)cycloalkyl;

$R_6'$ is H, ($C_3$-$C_8$)cycloalkyl, ($C_1$-$C_8$)alkyl, ($C_1$-$C_6$)alkylene-O—($C_1$-$C_6$)alkyl, ($C_1$-$C_3$)alkylene-R'; C(O) ($C_3$-$C_8$)cycloalkyl, C(O)($C_5$-$C_6$)heterocyclyl, C(O) ($C_1$-$C_6$)alkylene-($C_3$-$C_8$)cycloalkyl, C(O)($C_1$-$C_6$)alkylene-($C_5$-$C_6$)heterocyclyl or C(O)($C_1$-$C_6$)alkylene-($C_6$-$C_{10}$);

$R_7$ is H, halogen, CN, ($C_1$-$C_6$)alkyl, O—($C_1$-$C_6$)alkyl or ($C_2$-$C_6$)alkenyl;

m is 3 n is 1, 2 or 3; and

L is O.

44. The compound according to claim 1, wherein $R_1$ is H, or N[($C_1$-$C_4$)alkyl]$_2$;

$R_2$ is H or ($C_1$-$C_4$)alkyl;

$R_3$ is H, NH—($C_5$-$C_6$)heteroaryl or NH-phenyl;

$R_4$ is H, halogen or ($C_1$-$C_4$)alkyl;

$R_5$ is H, ($C_1$-$C_4$)alkyl, halogen, or ($C_2$-$C_4$)alkenyl;

$R_6$ is H or ($C_1$-$C_4$)alkyl;

$R_6'$ is H, ($C_3$-$C_8$)cycloalkyl, ($C_1$-$C_8$)alkyl, ($C_1$-$C_3$)alkylene-R'; C(O)O—($C_1$-$C_6$)alkyl, C(O)($C_3$-$C_6$)cycloalkyl, C(O)($C_5$-$C_6$)heterocyclyl, C(O)($C_1$-$C_3$)alkylene-($C_3$-$C_6$)cycloalkyl, C(O)($C_1$-$C_3$)alkylene-($C_5$-$C_6$) heterocyclyl, or C(O)($C_1$-$C_3$)alkylene-phenyl;

$R_7$ is H, halogen, CN, ($C_1$-$C_4$)alkyl, O—($C_1$-$C_4$)alkyl or ($C_2$-$C_4$)alkenyl;

$R_8$ is H, halogen or ($C_1$-$C_4$)alkyl;

m is 3 n is 1; and

L is O.

45. A pharmaceutical composition comprising a pharmaceutically effective amount of at least one compound according to claim 1 and/or a pharmacologically acceptable salt thereof, and physiologically tolerated excipient or carriers, and optionally one or more additives and/or one or more other active compounds.

46. A compound selected from the group consisting of;

trans-[4-(7-Chloro-isoquinolin-6-yloxy)-cyclohexyl]-carbamic acid tert-butyl ester, trans-4-(7-Chloro-isoquinolin-6-yloxy)-cyclohexylamine, [cis-4-(5-Chloro-isoquinolin-6-yloxy)-cyclohexyl]-carbamic acid tert-butyl ester, cis-4-(5-Chloro-isoquinolin-6-yloxy)-cyclohexylamine, cis-4-(4-Chloro-isoquinolin-6-yloxy)-cyclohexylamine, cis-4-(7-Methoxy-isoquinolin-6-yloxy)-cyclohexylamine, trans-4-(5-Bromo-isoquinolin-6-yloxy)-cyclohexylamine, cis-4-(5-Bromo-isoquinolin-6-yloxy)-cyclohexylamine, (3-Fluoro-benzyl)-[cis-4-(isoquinolin-6-yloxy)-cyclohexyl]-amine, [cis-4-(Isoquinolin-6-yloxy)-cyclohexyl]-propyl-amine, [cis-4-(Isoquinolin-6-yloxy)-cyclohexyl]-(3,3,3-trifluoropropyl)-amine, [cis-4-(Isoquinolin-6-yloxy)-cyclohexyl]-pyridin-3-ylmethyl-amine, Cyclopropylmethyl-cis-[4-(isoquinolin-6-yloxy)-cyclo-hexyl] amine, Isobutyl-cis-[4-(isoquinolin-6-yloxy)-cyclohexyl]-amine, Isopropyl-cis-[4-(isoquinolin-6-yloxy)-cyclohexyl]-amine, Cyclopropyl-[4-(isoquinolin-6-yloxy)-cyclohexyl]-amine, [4-(Isoquinolin-6-yloxy)-cyclohexyl]-dimethyl-amine, Ethyl-[4-(isoquinolin-6-yloxy)-cyclohexyl]-pyridin-4-ylmethyl-amine, Benzyl-[4-(isoquinolin-6-yloxy)-cyclohexyl]-methyl-amine, [4-(Isoquinolin-6-yloxy)-cyclohexyl]-(4-phenoxy-benzyl)-amine, [4-(Isoquinolin-6-yloxy)-cyclohexyl]-[5-(4-methoxy-phenyl)-isoxazol-3-ylmethyl]-amine, N-(4-{[4-(Isoquinolin-6-yloxy)-cyclohexylamino]-methyl}-phenyl)-acetamide, [4-(Isoquinolin-6-yloxy)-cyclohexyl]-(4-methoxy-benzyl)-amine, (4-Chloro-benzyl)-[4-(isoquinolin-6-yloxy)-cyclohexyl]-amine, (2,3-Dimethoxy-benzyl)-[4-(isoquinolin-6-yloxy)-cyclohexyl]-amine, 5-(4-{[4-(Isoquinolin-6-yloxy)-cyclohexylamino]-methyl}-phenyl)-5-methyl-imidazolidine-2,4-dione, (3,5-Dimethoxy-benzyl)-[4-(isoquinolin-6-yloxy)-cyclohexyl]-amine, 3-{[4-(Isoquinolin-6-yloxy)-cyclohexylamino]-methyl}-benzonitrile, [4-(Isoquinolin-6-yloxy)-cyclohexyl]-(4-methanesulfonyl-benzyl)-amine, [2-(1H-Indol-3-yl)-ethyl]-[4-(isoquinolin-6-yloxy)-cyclohexyl]-methyl-amin, 2-{[4-(Isoquinolin-6-yloxy)-cyclohexyl]-methyl-amino}-N,N-dimethyl-acetamide, 4-[4-(Isoquinolin-6-yloxy)-cyclohexyl]-piperazine-1-carboxylic acid ethyl ester, Isobutyl-[4-(isoquinolin-6-yloxy)-cyclohexy]methyl-amine, [4-(Isoquinolin-6-yloxy)-cyclohexyl]-methyl-pyridin-4-ylmethyl-amine, Ethyl-[4-(isoquinolin-6-yloxy)-cyclohexyl]-(2-methoxy-ethyl)-amine, 4-{[4-(Isoquinolin-6-yloxy)-cyclohexylamino]-methyl}-benzonitrile, 6-(4-Morpholin-4-yl-cyclohexyloxy)-isoquinoline, 4-{[4-(Isoquinolin-6-yloxy)-cyclohexylamino]methyl}-benzoic acid methyl ester, (4-tert-Butyl-benzyl)-[4-(isoquinolin-6-yloxy)-cyclohexyl]-amine, [1-(4-Fluoro-phenyl)-1H-pyrazol-4-ylmethyl]-[4-(isoquinolin-6-yloxy)-cyclohexyl]-methyl-amine, [4-(Isoquinolin-6-yloxy)-cyclohexyl]-(5-methyl-3-phenyl-isoxazol-4-ylmethyl)-amine, [4-(Isoquinolin-6-yloxy)-cyclohexyl]-naphthalen-1-ylmethyl-amine, [4-(Isoquinolin-6-yloxy)-cyclohexyl]-(2-phenyl-oxazol-4-ylmethyl)-amine, (2,3-Dihydro-benzofuran-5-ylmethyl)-[4-(isoquinolin-6-yloxy)-cyclohexyl]-amine, [4-(Isoquinolin-6-yloxy)-cyclohexyl]-(5-methyl-isoxazol-3-ylmethyl)-amine, [4-(Isoquinolin-6-yloxy)-cyclohexyl]-(2-thiophen-2-yl-thiazol-4-ylmethyl)-amine, (3,5-Dimethyl-benzyl)-[4-(isoquinolin-6-yloxy)-cyclohexyl]-amine, Biphenyl-2-ylmethyl-[4-(isoquinolin-6-yloxy)-cyclohexyl]-amine, [4-(Isoquinolin-6-yloxy)-cyclohexyl]-(4-pyrazol-1-yl-benzyl)-amine, [4-(isoquinolin-6-yloxy)-cyclohexyl]-(4-methoxy-phenyl)-amine, Cyclopropyl-[trans-4-(isoquinolin-6-yloxy)-cyclohexyl]-amine, Cyclopropyl-[cis-4-(isoquinolin-6-yloxy)-cyclohexyl]-amine, [trans-4-(Isoquinolin-6-yloxy)-cyclohexyl]-(4-phenoxy-benzyl)-amine, [cis-4-(Isoquinolin-6-yloxy)-cyclohexyl]-(4-phenoxy-benzyl)-amine, Benzyl-[trans-4-(isoquinolin-6-yloxy)-cyclohexyl]-methyl-amine, Benzyl-[cis-4-(isoquinolin-6-yloxy)-cyclohexyl]-methyl-amine, [trans-4-(Isoquinolin-6-yloxy)-cyclohexyl]-dimethyl-amine, [cis-4-(Isoquinolin-6-yloxy)-cyclohexyl]-dimethyl-amine, N-(4-{[trans-4-(Isoquinolin-6-yloxy)-cyclohexylamino]-methyl}-phenyl)-acetamide, N-(4-{[cis-4-(Isoquinolin-6-yloxy)-cyclohexylamino]-methyl}-phenyl)-acetamide, 2-Chloro-5-{cis[4-(5-chloro-isoquinolin-6-yloxy)-cyclohexylamino]-methyl}-N-dimethylaminomethylene-benzenesulfonamide, 2-Chloro-5-{[-chloro-isoquinolin-6-yloxy)-cyclohexyl amino]-methyl}-benzenesulfonamide, Cyclopropylmethyl-[trans-4-(isoquinolin-6-yloxy)-cyclohexyl]-amine, Bis-cyclopropylmethyl-[trans-4-(isoquinolin-6-yloxy)-cyclohexyl]-amine, [4-(5-Chloro-isoquinolin-6-yloxy)-cyclohexyl]-cyclohexyl-amine, [4-(5-Chloro-isoquinolin-6-yloxy)-cyclohexyl]-cyclopropyl-amine, [4-(5-Chloro-isoquinolin-6-yloxy)-cyclohexyl]-cyclobutyl-amine, [4-(5-Chloro-isoquinolin-6-yloxy)-cyclohexyl]-cyclopentyl-amine, [4-(5-Chloro-isoquinolin-6-yloxy)-cyclohexyl]-isopropyl-amine, [cis-4-(5-Bromo-isoquinolin-6-yloxy)-cyclohexyl]-carbamic acid tert-butyl ester, cis-4-(5-Ethyl-isoquinolin-6-yloxy)-cyclohexylamine, cis-4-(5-Methyl-isoquinolin-6-yloxy)-cyclohexylamine, cis-4-(5-Vinyl-isoquinolin-6-yloxy)-cyclohexylamine, trans-4-(5,7-Dichloro-isoquinolin-6-yloxy)-cyclohexylamine, [cis-4-(7-Chloro-isoquinolin-6-yloxy)-cyclohexyl]-carbamic acid tert-butyl ester, cis-4-(7-Chloro-isoquinolin-6-yloxy)-cyclohexylamine, cis-4-(5,7-Difluoro-isoquinolin-6-yloxy)-cyclohexylamine, [cis-4-(7-Chloro-isoquinolin-6-yloxy)-cyclohexyl]-propyl-amine, Butyl-[cis-4-(7-chloro-isoquinolin-6-yloxy)-cyclohexyl]-amine, [cis-4-(7-Chloro-isoquinolin-6-yloxy)-cyclohexyl]-isopropyl-amine, [cis-4-(7-Chloro-isoquinolin-6-yloxy)-cyclohexyl]-(1-ethyl-propyl)-amine, [cis-4-(7-Chloro-isoquinolin-6-yloxy)-cyclohexyl]-isobutyl-amine, [cis-4-(7-Chloro-isoquinolin-6-yloxy)-cyclohexy]-cyclopropylmethyl-amine, [cis-4-(7-Chloro-isoquinolin-6-yloxy)-cyclohexyl]-(3-methyl-butyl)-amine, [cis-4-(7-Chloro-isoquinolin-6-yloxy)-cyclohexyl]-cyclohexylmethyl-amine, [cis-4-(7-Chloro-isoquinolin-6-yloxy)-cyclohexyl]-cyclohexyl-amine, (4-Chloro-benzyl)-[cis-4-(7-chloro-isoquinolin-6-yloxy)-cyclohexyl]-amine, (3-Chloro-benzyl)-[cis-4-(7-chloro-isoquinolin-6-yloxy)-cyclohexyl]-amine, [cis-4-(7-Chloro-isoquinolin-6-yloxy)-cyclohexyl]-(2,4-dichloro-benzyl)-amine, [cis-4-(7-Chloro-isoquinolin-6-yloxy)-cyclohexy]-4-(4-trifluoromethyl-benzyl)-amine, [cis-4-(7-Chloro-isoquinolin-6-yloxy)-cyclohexy]pyridin-4-ylmethyl-amine, [cis-4-(7-Chloro-isoquinolin-6-yloxy)-cyclohexyl]-ethyl-amine, [trans-4-(7-Chloro-isoquinolin-6-yloxy)-cyclohexyl]-propyl-amine, Butyl-[trans-4-(7-chloro-isoquinolin-6-yloxy)-cyclohexyl]-amine, [trans-4-(7-Chloro-isoquinolin-6-yloxy)-cyclohexyl]-isopropyl-amine, [trans-4-(7-Chloro-isoquinolin-6-yloxy)-cyclohexyl]-(3-methyl-butyl)-amine, [trans-4-(7-Chloro-isoquinolin-6-yloxy)-cyclohexyl]-cyclohexylmethyl-amine, Benzyl-[trans-4-(7-chloro-isoquinolin-6-yloxy)-cyclohexyl]-amine, [trans-4-(7-Chloro-isoquinolin-6-yloxy)-cyclohexyl]-(4-methyl-benzyl)-amine, [trans-4-(7-Chloro-isoquinolin-6-yloxy)-cyclohexyl]-pyridin-3-ylmethyl-amine, [trans-4-(7-Chloro-isoquinolin-6-yloxy)-cyclohexyl]-(4-methanesulfonyl-benzyl)-amine, [trans-4-(7-Chloro-isoquinolin-6-yloxy)-cyclohexyl]-naphthalen-1-ylmethyl-amine, [trans-4-(7-Chloro-isoquinolin-6-yloxy)-cyclohexyl]-(tetrahydro-furan-3-ylmethyl)-amine, [trans-4-(7-Chloro-isoquinolin-6-yloxy)-cyclohexyl]-cyclohexyl-amine, [trans-4-(7-Chloro-isoquinolin-6-yloxy)-cyclohexyl]-cyclopropylmethyl-amine, [trans-4-(7-Chloro-isoquinolin-6-yloxy)-cyclohexyl]-isobutyl-amine, (4-Chloro-benzyl)-[trans-4-(7-chloro-isoquinolin-6-yloxy)-cyclohexyl]-amine, (3-Chloro-benzyl)-[trans-4-(7-chloro-isoquinolin-6-yloxy)-cyclohexyl]-amine, [trans-4-(7-Chloro-isoquinolin-6-yloxy)-cyclohexyl]-(2,4-dichloro-benzyl)-amine, [trans-4-(7-Chloro-isoquinolin-6-yloxy)-cyclohexyl]-(3,5-dichloro-benzyl)-amine, (2-Chloro-benzyl)-[trans-4-(7-chloro-isoquinolin-6-yloxy)-cyclohexyl]-amine, 3-{[trans-4-(7-Chloro-isoquinolin-6-yloxy)-cyclohexylamino]-methyl}-N-[1- dimethylamino-meth-(E)-ylidene]-4-methoxy-benzenesulfonamide, [trans-4-(7-Chloro-isoquinolin-6-yloxy)-cyclohexyl]-4-(4-trifluoromethanesulfonyl-benzyl)-amine, [trans-4-(7-Chloro-isoquinolin-6-yloxy)-cyclohexyl]-4-(4-trifluoromethyl-benzyl)-amine, [6-(cis-4-Amino-cyclohexyloxy)-isoquinolin-3-yl]-(3-methoxy-phenyl)-amine, [6-(cis-4-Amino-cyclohexyloxy)-isoquinolin-3-yl]-(4-methoxy-phenyl)-amine, [6-(cis-4-Amino-cyclohexyloxy)-isoquinolin-3-yl]-(3-chloro-phenyl)-amine, [6-(cis-4-Amino-cyclohexyloxy)-isoquinolin-3-yl]-(4-chloro-phenyl)-amine, [6-(cis-4-Amino-cyclohexyloxy)-isoquinolin-3-yl]-(3,4,5-trimethoxy-phenyl)-amine, [6-(cis-4-Amino-cyclohexyloxy)-isoquinolin-3-yl]-pyrazin-2-yl-amine, and cis-4-(4-Ethyl-isoquinolin-6-yloxy)-cyclohexylamine; or a pharmaceutically acceptable salt thereof.

* * * * *